United States Patent
Hughes et al.

(10) Patent No.: US 7,902,195 B2
(45) Date of Patent: Mar. 8, 2011

(54) PYRIDINE [3,4-B] PYRAZINONES

(75) Inventors: Robert O Hughes, Eureka, MO (US); Andrew Simon Bell, Sandwich (GB); David Graham Brown, Sandwich (GB); Dafydd Owen, Sandwich (GB); Michael John Palmer, Sandwich (GB); Christopher Phillips, Sandwich (GB); David L. Brown, Chesterfield, MO (US); Yvette M. Fobian, Wildwood, MO (US); John N. Freskos, Clayton, MO (US); Steven E. Heasley, St. Charles, MO (US); E. Jon Jacobsen, Chesterfield, MO (US); Todd Maddux, Foristell, MO (US); Brent Mischke, Defiance, MO (US); John M. Molyneaux, St. Louis, MO (US); Joseph B. Moon, University City, MO (US); D. Joseph Rogier, Jr., Chesterfield, MO (US); Michael B. Tollefson, Dardenne Prairie, MO (US); John K. Walker, Weldon Spring, MO (US)

(73) Assignee: Pharmacia & Upjohn Company LLC, Kalamazoo, MI (US)

( * ) Notice: Subject to any disclaimer, the term of this patent is extended or adjusted under 35 U.S.C. 154(b) by 131 days.

(21) Appl. No.: 11/737,966

(22) Filed: Apr. 20, 2007

(65) Prior Publication Data
US 2007/0249615 A1    Oct. 25, 2007

Related U.S. Application Data

(60) Provisional application No. 60/793,971, filed on Apr. 21, 2006.

(51) Int. Cl.
*A61K 31/4985* (2006.01)
(52) U.S. Cl. .......................... 514/249; 544/350
(58) Field of Classification Search .................. 544/350
See application file for complete search history.

(56) References Cited

U.S. PATENT DOCUMENTS

| | | | |
|---|---|---|---|
| 5,283,244 | A | 2/1994 | Sakamoto et al. |
| 5,424,311 | A | 6/1995 | Troughton et al. |
| 6,369,056 | B1 | 4/2002 | Zhang et al. |
| 7,067,658 | B2 | 6/2006 | Dzurdz et al. |
| 2002/0111355 | A1 | 8/2002 | Zhang et al. |
| 2002/0147199 | A1 | 10/2002 | Marx et al. |
| 2004/0082784 | A1 | 4/2004 | Dzurdz et al. |
| 2006/0009457 | A1 | 1/2006 | Hoffmann et al. |
| 2006/0135511 | A1 | 6/2006 | Burgey |
| 2007/0053831 | A1 | 3/2007 | Barrio et al. |
| 2007/0155730 | A1 | 7/2007 | Leit et al. |
| 2007/0249611 | A1 | 10/2007 | Feng et al. |
| 2007/0249615 | A1 | 10/2007 | Hughes et al. |
| 2008/0020985 | A1 | 1/2008 | Cai et al. |

FOREIGN PATENT DOCUMENTS

| | | |
|---|---|---|
| EP | 1 364 950 A1 | 11/2003 |
| FR | 1361652 A | 5/1964 |
| JP | 2000154139 A2 | 6/2000 |
| WO | WO 0276954 A1 | 3/2002 |
| WO | WO 2006/126082 A | 11/2006 |

OTHER PUBLICATIONS

J. N. Ren, et al., The PDE5 Inhibitor Sildenafil Improves Functional Recovery after Middle Cerebral Artery Occlusion in Rats: Mechanism of Action, 582.15, Society for Neuroscience, 36th Annual Meeting 2006.
Hoover, John E., Remington's Pharmaceutical Sciences, Mack Publishing Co., Easton, PA, 1975.
Lieberman, et al., Eds., Pharmaceutical Dosage Forms, Marcel Decker, New York, NY, 1980.
Kibbe, et al., Eds. Handbook of Pharmaceutical Excipients (3rd Ed), American Pharmaceutical Association, Washington, 1999.
Compendium of Organic Synthetic Methods, vol. I-VI/ published by Wiley-Interscience, 1971, 1974, 1977, 1980, 1984, 1988.
Green, T., et al., Protecting Groups in Organic Synthesis, John Wiley & Sons, Inc., Second Edition, Chapter 7, pp. 309-405, 1991.
Miyaura, N., et al., Palladium-Catalyzed Cross-Coupling Reactions of Organoboron Compounds, Chem Rev. 95, pp. 2457-2483, 1995.
Ley, S., et al., Modern Synthetic Methods for Copper-Mediated C9aryl)-O,C(aryl)-N, and C(aryl)-S Bond Formation, Angew. Chem. Int. Ed., 42, pp. 5400-5449, 2003.
Thompson, W. J., et al., Purification and Characterization of High-Affinity Cyclic Adenosine Monophosphate Phosphodiesterase from Dog Kidney, Biochemistry 18(23), p. 5228-5237, 1979.
Ballard, S. A., et al., Effects of Sildenafil on the Relxation of Human Corpus Cavernosum Tissue in Vitro and on the Activities of cyclic Nucleotide Phosphodiesterase Isozymes, J. Urology 159(6), p. 2164-2171, 1998.
DeLean, A., et al., Simultaneous Analysis of Families of Sigmoidal Curves: Application to Bioassay, Radioligand Assay, and physiological Dose-response Curves, Am. J. Physiol. 235(2): E97-E102, 1978.
J. N. Ren, et al., *The PDE5 Inhibitor Sildenafil Improves Functional Recovery after Middle Cerebral Artery Occlusion in Rats: Mechanism of Action*, 582.15,Society for Neuroscience, 36th Annual Meeting 2006.
Green, T., et al., *Protecting Groups in Organic Synthesis*, John Wiley & Sons, Inc., Second Edition, Chapter 7,pp. 309-405, 1991.

(Continued)

*Primary Examiner* — James O Wilson
*Assistant Examiner* — Brian McDowell
(74) *Attorney, Agent, or Firm* — Jennifer A. Kispert; Robert T. Ronau

(57) ABSTRACT

Compounds and pharmaceutically acceptable salts of the compounds are disclosed, wherein the compounds have the structure of Formula I:

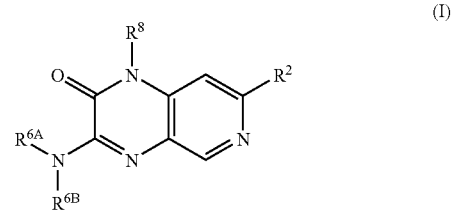

(I)

wherein $R^2$, $R^{6A}$, $R^{6B}$ and $R^8$ are as defined in the specification. Corresponding pharmaceutical compositions, methods of treatment, synthetic methods, and intermediates are also disclosed.

45 Claims, No Drawings

OTHER PUBLICATIONS

Miyaura, N., et al., *Palladium-Catalyzed Cross-Coupling Reactions of Organoboron Compounds*, Chem Rev. 95, pp. 2457-2483, 1995.

Ley, S., et al., *Modern Synthetic Methods for Copper-Mediated C9aryl)-O,C(alyl)-N, and C(aryl)-S Bond Formation*, Angew. Chem. Int. Ed., 42, pp. 5400-5449, 2003.

Thompson, W. J., et al., *Purification and Characterization of High-Affinity Cyclic Adenosine Monophosphate Phosphodiesterase from Dog Kidney*, Biochemistry 18(23), pp. 5228-5237, 1979.

Ballard, S.A., et al., *Effects of Sildenafil on the Relaxation of Human Corpus Cavernosum Tissue in Vitro and on the Activities of Cyclic Nucleotide Phosphodiesterase Isozymes*, J. Urology 159(6), pp. 2164-2171, 1998.

DeLean, A., et al., *Simultaneous Analysis of Families of Sigmoidal Curves: Application to Bioassay, Radioligand Assay, and Physiological Dose-response Curves*, Am. J. Physiol. 235(2): E97-E102, 1978.

PYRIDINE [3,4-B] PYRAZINONES

This application claims the benefit of U.S. Provisional Application No. 60/793,971 filed Apr. 21, 2006.

FIELD OF THE INVENTION

The present invention comprises a class of pyridine[3,4-b] pyrazinone compounds having the structure of Formula I and pharmaceutical compositions comprising a compound of Formula I. The present invention also comprises methods of treating a subject by administering a therapeutically effective amount of a compound of Formula I to the subject. In general, these compounds inhibit, in whole or in part, the enzyme: cyclic guanylate monophosphate-specific phosphodiesterase type 5 (PDE-5).

BACKGROUND OF THE INVENTION

The prevalence of hypertension in developed countries is about 20% of the adult population, rising to about 60-70% of those aged 60 or more. Hypertension is associated with an increased risk of stroke, myocardial infarction, atrial fibrillation, heart failure, peripheral vascular disease and renal impairment. Despite the large number of anti-hypertensive drugs available in various pharmacological categories, additional agents useful for the treatment of hypertension are still needed.

Vascular endothelial cells secrete nitric oxide (NO). This acts on vascular smooth muscle cells and leads to the activation of guanylate cyclase and the accumulation of cyclic guanosine monophosphate (cGMP). The accumulation of cGMP causes the muscles to relax and the blood vessels to dilate, leading to a reduction in blood pressure. The cGMP is inactivated by hydrolysis to guanosine 5'-monophosphate (GMP) by a cGMP-specific phosphodiesterase. One important cGMP-phosphodiesterase has been identified as phosphodiesterase type 5 (PDE5). Inhibitors of PDE5 decrease the rate of hydrolysis of cGMP and so potentiate the actions of nitric oxide.

Improved drug therapies for the treatment of subjects suffering from or susceptible to a cardiovascular condition are desirable. In particular, there still is a need for a new class of PDE-5 inhibitors for treating cGMP-mediated conditions and corresponding drug therapies.

SUMMARY OF THE INVENTION

In one embodiment, the invention comprises compounds having the structure of Formula I:

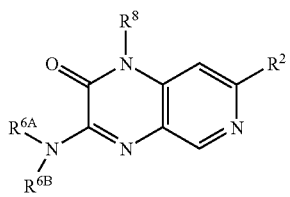

(I)

wherein $R^2$, $R^{6A}$, $R^{6B}$, and $R^8$ are as defined in the detailed description of the invention.

In another embodiment, the invention comprises a pharmaceutical composition comprising a compound having the structure of Formula I.

In another embodiment, the invention comprises methods of treating a condition in a subject by administering a therapeutically effective amount of a compound having the Formula I to the subject. The conditions that can be treated in accordance with the present invention include cardiovascular conditions, metabolic conditions, central nervous system conditions, pulmonary conditions, sexual dysfunction, and renal dysfunction.

In another embodiment, the invention comprises a method for inhibiting PDE-5, and particularly methods for treating a condition (typically a pathological condition) mediated by PDE-5 by administering a compound having a structure of Formula I to the subject.

In another embodiment, the invention comprises methods of making compounds having the structure of Formula I.

In another embodiment, the invention comprises intermediates useful in the synthesis of compounds having the structure of Formula I.

DETAILED DESCRIPTION OF THE INVENTION

This detailed description of embodiments is intended only to acquaint others skilled in the art with Applicants' inventions, its principles, and its practical application so that others skilled in the art may adapt and apply the inventions in their numerous forms, as they may be best suited to the requirements of a particular use. These inventions, therefore, are not limited to the embodiments described in this specification, and may be variously modified.

A. Abbreviations and Definitions

As used in reference to $^1$H NMR, the symbol "δ" refers to a $^1$H NMR chemical shift.

As used in reference to $^1$H NMR, the abbreviation "br" refers to a broad $^1$H NMR signal.

As used in reference to $^1$H NMR, the abbreviation "d" refers to a doublet $^1$H NMR peak.

As used in reference to $^1$H NMR, the abbreviation "dd" refers to a doublet of doublets $^1$H NMR peak.

The abbreviation "HRMS" refers to High Resolution Mass Spectroscopy (electrospray ionisation positive scan).

The abbreviation "m/z" refers to a Mass spectrum peak.

As used in reference to $^1$H NMR, the abbreviation "m" refers to a multiplet $^1$H NMR peak.

As used in reference to $^1$H NMR, the abbreviation "q" refers to a quartet $^1$H NMR peak.

As used in reference to $^1$H NMR, the abbreviation "s" refers to a singlet $^1$H NMR peak.

As used in reference to $^1$H NMR, the abbreviation "t" refers to a triplet $^1$H NMR peak.

The abbreviation "TFA" refers to trifluoroacetic acid.

The term "alkyl" (alone or in combination with other term(s)) refers to a linear or branched-chain saturated hydrocarbyl substitutent (i.e., a substitutent containing only carbon and hydrogen) typically containing from about one to about twenty carbon atoms or; in another embodiment from about one to about twelve carbon atoms; in another embodiment, from about one to about ten carbon atoms; in another embodiment, from about one to about six carbon atoms; and in another embodiment, from about one to about four carbon atoms. Examples of such substituents include methyl, ethyl, propyl (including n-propyl and isopropyl), butyl (including n-butyl, isobutyl, sec-butyl and tert-butyl), pentyl, iso-amyl, hexyl and the like.

The term "alkenyl" (alone or in combination with other term(s)) refers to a linear or branched-chain hydrocarbyl substituent containing one or more double bonds and from about two to about twenty carbon atoms; in another embodiment, from about two to about twelve carbon atoms; in another embodiment, from about two to about six carbon atoms; and in another embodiment, from about two to about four carbon atoms. Examples of alkenyl radicals include ethenyl, allyl, propenyl, butenyl and 3-methylbutenyl.

The terms "alkenyl", and "lower alkenyl", embrace radicals having "cis" and "trans" orientations, or alternatively, "Z" and "E" orientations.

The term "alkynyl" (alone or in combination with other term(s)) refers to linear or branched-chain heterocarbyl substituents containing one or more triple bonds and from about two to about twenty carbon atoms; in another embodiment, from about two to about twelve carbon atoms; in another embodiment, from about two to about six carbon atoms; and in another embodiment, from about two to about four carbon atoms. Examples of alkynyl radicals include 1-propynyl, 2-propynyl, 1-butyne, 2-butynyl and 1-pentynyl.

The term "amino", alone or in combination with another term(s), refers to —NH$_2$ when it is at a terminal position or to —NH— when it is used in combination with another term(s) and is not at a terminal position.

The term "aryl", alone or in combination with another term(s), refers to a carbocyclic aromatic system containing one, two or three rings wherein such rings may be attached together in a pendent manner or may be fused. Examples of aryl moieties include phenyl, naphthyl, tetrahydronaphthyl, indanyl and biphenyl.

The term "carboxy", alone or in combination with another term(s), refers to a radical of the formula —C(O)OH.

The term "cyano", alone or in combination with another term(s), means —CN, which also may be depicted:

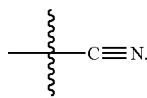

The term "cycloalkyl", alone or in combination with another term(s), refers to saturated carbocyclic radicals having three to about twelve carbon atoms. In another embodiment, cycloalkyl radicals are "lower cycloalkyl" radicals having three to about eight carbon atoms. Examples of such radicals include cyclopropyl, cyclobutyl, cyclopentyl and cyclohexyl.

The term "cycloalkylalkyl", alone or in combination with another term(s), refers to alkyl substituted with cycloalkyl. Examples of such substituents include cyclopropylmethyl, cyclobutylmethyl, cyclopentylmethyl, and cyclohexylmethyl.

The term "cycloalkenyl", alone or in combination with another term(s), refers to a partially unsaturated carbocyclyl substituent. Examples of such substituents include cyclobutenyl, cyclopentenyl, and cyclohexenyl.

The term "halogen" or "halo", alone or in combination with another term(s), refers to means a fluorine radical (which may be depicted as —F), chlorine radical (which may be depicted as —Cl), bromine radical (which may be depicted as —Br), or iodine radical (which may be depicted as —I). In another embodiment, the halogen is a fluorine or chlorine radical. In another embodiment, the halogen is a fluorine radical.

When used in combination with another term(s), the prefix "halo" indicates that the substituent to which the prefix is attached is substituted with one or more independently selected halogen radicals. For example, haloalkyl refers to an alkyl substituent wherein at least one hydrogen radical is replaced with a halogen radical. Where there are more than one hydrogens replaced with halogens, the halogens may be the same or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluoropropyl, dichloropropyl, and heptafluoropropyl. Illustrating further, "haloalkoxy" means an alkoxy substituent wherein at least one hydrogen radical is replaced by a halogen radical. Examples of haloalkoxy substituents include chloromethoxy, 1-bromoethoxy, fluoromethoxy, difluoromethoxy, trifluoromethoxy (also known as "perfluoromethyloxy"), and 2,2,2,-trifluoroethoxy. If a substituent is substituted by more than one halogen radical, those halogen radicals may be identical or different (unless otherwise stated).

A heterocyclyl may be a single ring, which typically contains from 3 to 10 ring atoms, more typically from 3 to 7 ring atoms, and even more typically 5 to 6 ring atoms. Examples of single-ring heterocyclyls include furanyl, dihydrofuranyl, tetrahydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl. A heterocyclyl alternatively may comprise 2 or 3 rings fused together, wherein at least one such ring contains a heteroatom as a ring atom (e.g., nitrogen, oxygen, or sulfur). Examples of 2-fused-ring heterocyclyls include, indolizinyl, pyrindinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl. Other examples of fused-ring heterocyclyls include benzo-fused heterocyclyls, such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxoiyl, benzodioxanyl, benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothionaphthenyl," or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "heteroaryl", alone or in combination with another term(s), refers to a completely unsaturated (i.e., aromatic) heterocyclyl containing from 5 to 14 ring atoms. A heteroaryl may comprise a single ring or 2 or 3 fused rings. In one embodiment, heteroaryl radicals are 5- or 6-membered heteroaryl, containing one or two heteroatoms selected from sulphur, nitrogen and oxygen, selected from thienyl, furanyl, thiazolyl, imidazolyl, pyrazolyl, isoxazolyl, isothiazolyl, pyridyl and pyrazinyl. Examples of heteroaryl substituents include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, and thiazolyl; 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as 1,2-, 1,4-, 2,3- and 2,1-benzopyronyl, quinolinyl, isoquinolinyl, cinnolinyl, quinazolinyl, and 1,4-benzoxazinyl. Other heteroaryls include unsaturated 5 to 6 membered heteromonocyclyl groups containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, isoxazolyl, oxadiazolyl [e.g., 1,2,4-oxadiazolyl, 1,3,4-oxadiazolyl, 1,2,5-oxadiazolyl]; unsaturated condensed heterocyclic groups containing 1 to 2 oxygen atoms and 1 to 3 nitrogen atoms [e.g. benzoxazolyl, benzoxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]; unsaturated condensed heterocyclic groups containing 1 to 2 sulfur atoms and 1 to 3 nitrogen atoms [e.g., benzothiazolyl, benzothiadiazolyl] and the like. The term also embraces radicals where heterocyclic radicals are fused with aryl radicals. Examples of such fused bicyclic radicals include benzofuran, benzothiophene, and the like.

The term "heterocyclylalkyl", alone or in combination with another term(s), refers to alkyl substituted with a heterocyclyl.

The term "hydroxy", alone or in combination with another term(s), refers to —OH.

The term "mercapto" or "thiol" refers to a sulfhydryl substituent, which also may depicted as —SH.

The term "nitro", alone or in combination with another term(s), refers to —NO$_2$.

The term "sulfonyl", alone or in combination with another term(s), refers to —S(O)$_2$—, which also may be depicted as:

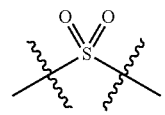

Thus, for example, "alkyl-sulfonyl-alkyl" refers to alkyl-S(O)$_2$-alkyl. Examples of typically preferred alkylsulfonyl substituents include methylsulfonyl, ethylsulfonyl, and propylsulfonyl.

The term "sulfoxyl", alone or in combination with another term(s), refers to —S(O)—, which also may be depicted as:

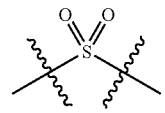

The term "thio" or "thia", alone or in combination with another term(s), refers to a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl.

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. This specification uses the terms "substituent" and "radical" interchangeably.

The term "PDE5-mediated condition" refers to any condition mediated by PDE5. The term "composition" refers to an article of manufacture which results from the mixing or combining of more than one element or ingredient.

The term "hypertensive subject" refers to a subject having hypertension, suffering from the effects of hypertension or susceptible to a hypertensive condition if not treated to prevent or control such hypertension.

The term "pharmaceutically acceptable carrier" refers to a carrier that is compatible with the other ingredients of the composition and is not deleterious to the subject. Such carriers may be pharmaceutically acceptable material, composition or vehicle, such as a liquid or solid filler, diluent, excipient, solvent or encapsulating material, involved in carrying or transporting a chemical agent. The preferred composition depends on the method of administration.

The terms "prevent," "prevention" or "preventing" refer to either preventing the onset of a preclinically evident condition altogether or preventing the onset of a preclinical evident stage of a condition in a subject. Prevention includes, but is not limited to, prophylactic treatment of a subject at risk of developing a condition.

The term "therapeutically effective amount" refers to that amount of drug or pharmaceutical agent that will elicit the biological or medical response of a tissue, system or animal that is being sought by a researcher or clinician.

The term "treatment" (and corresponding terms "treat" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents the occurrence of a condition in a subject. The term "restorative treatment" refers to treatment that halts the progression of, reduces the pathologic manifestations of, or entirely eliminates a condition in a subject.

B. Compounds

The present invention comprises, in part, a novel class of pyridine[3,4-b]pyrazinone compounds. These compounds are useful as inhibitors of PDE5.

Compounds of Formula (I)

As used herein, compounds of the present invention include tautomers of the compounds and pharmaceutically acceptable salts of the compounds and tautomers.

The present invention is directed, in part, to a class of compounds having the structure of Formula I:

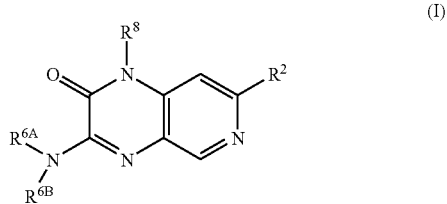

(I)

wherein $R^2$ is selected from the group consisting of aryl and 3 to 10 membered ring heterocycyl wherein said $R^2$ aryl and heterocyclyl substituents may be optionally substituted with one or more substituents independently selected from the group consisting of halogen, cyano, nitro, oxo, alkyl, alkenyl, alkynyl, cycloalkyl, —$OR^{201}$, —$C(O)R^{201}$, —$OC(O)R^{201}$, —$C(O)OR^{201}$, —$NR^{201}R^{202}$, —$N(R^{201})C(O)R^{202}$, —$C(O)NR^{201}R^{202}$, —$C(O)NR^{201}C(O)R^{202}$, —$SR^{201}$, —$S(O)R^{201}$, and —$S(O)_2R^{201}$; wherein said alkyl, alkenyl, and alkynyl and cycloalkyl substituents may be optionally substituted with one or more substituents independently selected from the group consisting of halogen, oxo, —$OR^{203}$, and —$C(O)OR^{203}$;

$R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy, alkoxy, carboxy and —$C(O)NH_2$;

$R^{6A}$ and $R^{6B}$ together with the nitrogen to which they are attached form a partially or fully saturated 3 to 14 membered ring heterocyclyl, wherein the heterocyclyl may be optionally substituted with one or more substituents independently selected from the group consisting of hydrogen, halogen, oxo, alkyl, alkenyl, alkynyl, cyano, —$OR^{601}$, —$C(O)R^{601}$, —$OC(O)R^{601}$, —$C(O)OR^{601}$, —$NR^{601}R^{602}$, —$N(R^{601})C(O)R^{602}$, —$C(O)NR^{601}R^{602}$, —$C(O)NR^{601}C(O)R^{602}$, cycloalkyl, aryl, and heterocyclyl, wherein (a) said alkyl, alkenyl, alkynyl and cycloalkyl substituents may be optionally substituted with one or more substituents independently selected from the group consisting of halogen, cyano, oxo, —$OR^{603}$, —$C(O)R^{603}$, —$C(O)OR^{603}$, —$OC(O)R^{603}$, —$NR^{603}R^{604}$, —$N(R^{603})C(O)R^{604}$, —$C(O)NR^{603}R^{604}$, —$C(O)NR^{603}C(O)R^{604}$, —$SR^{603}$, —$S(O)R^{603}$, —$S(O)_2R^{603}$, —$N(R^{603})S(O)_2R^{604}$, and —$S(O)_2NR^{603}R^{604}$, $C(O)NR^{603}C(O)R^{604}$, —$SR^{603}$, —$S(O)R^{603}$, —$S(O)_2R^{603}$, —$N(R^{603})S(O)_2R^{604}$, and —$S(O)_2NR^{603}R^{604}$, and (b) said aryl and heterocyclyl substituents may be optionally substituted with one or more substituents independently selected from the group consisting of halogen, alkyl, alkenyl, alkynyl, cyano, oxo, —$R^{601}$, —$C(O)R^{601}$, —$C(O)OR^{601}$, —$OC(O)R^{601}$, —$NR^{601}R^{602}$, —$N(R^{601})C(O)R^{602}$, —$C(O)NR^{601}R^{602}$, —$C(O)NR^{601}C(O)R^{602}$, —$SR^{601}$, —$S(O)R^{602}$, —$S(O)_2R^{601}$, —$N(R^{601})S(O)_2R^{602}$, and —$S(O)_2NR^{601}R^{602}$;

$R^{601}$, $R^{602}$, $R^{603}$ and $R^{604}$ are independently selected from the group consisting of hydrogen, alkyl, alkenyl, and alkynyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy, and (b) said $R^{601}$ and $R^{602}$ alkenyl and alkynyl substituents may be optionally substituted with one or more substituents independently selected from the group consisting of halogen, cyano, hydroxy, carboxy, oxo, alkoxy, haloalkoxy, hydroxyalkoxy, and carboxyalkoxy;

$R^8$ is alkyl; wherein said $R^8$ substituent may be optionally substituted with one or more substituents independently selected from the group consisting of halogen, cyano, hydroxy, carboxy, alkenyl, alkynyl, —$OR^{801}$, —$C(O)R^{801}$, —$C(O)OR^{801}$, —$OC(O)R^{801}$, —$NR^{801}R^{802}$, —$N(R^{801})C(O)R^{802}$, —$C(O)NR^{801}R^{802}$, and —$C(O)NR^{801}C(O)R^{802}$, wherein said alkenyl and alkynyl substituents may be optionally substituted with one or more substituents independently selected from the group consisting of halogen, cyano, hydroxy, carboxy, oxo, and alkoxy; and $R^{801}$ and $R^{802}$ are independently selected from the group consisting of hydrogen, alkyl, alkenyl and alkynyl, wherein (a) when said alkyl is methyl, said methyl may be optionally substituted with 1, 2, or 3 fluoro substituents, (b) when said alkyl comprises at least two carbon atoms, said alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy, and (c) said $R^{801}$ and $R^{802}$ alkenyl and alkynyl substituents may be optionally substituted with one or more substituents independently selected from the group consisting of halogen, cyano, hydroxy, carboxy, oxo, alkoxy, haloalkoxy, hydroxyalkoxy, and carboxyalkoxy.

Selected subclasses of compounds of interest that fall within the scope of the compounds of Formula I are shown in Table A, wherein $R^2$, $R^{6A}$, $R^{6B}$ and $R^8$ are as defined for compounds of Formula I and as defined in the various embodiments described throughout this specification. Illustrative embodiments of these subclasses of compounds are described later in the specification.

TABLE A
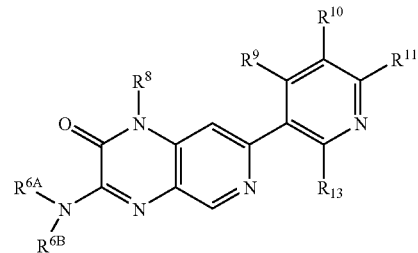

TABLE A-continued
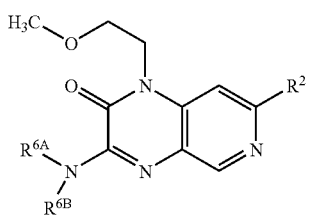
(I-13)
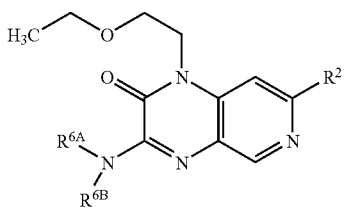
(I-14)
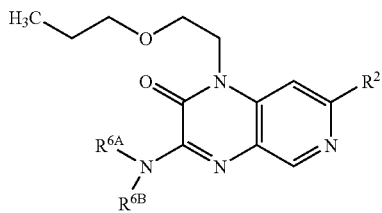
(I-15)
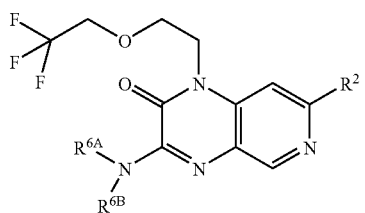
(I-16)
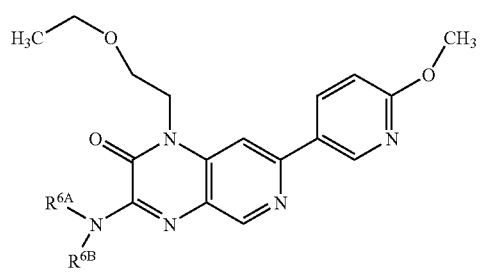
(I-17)
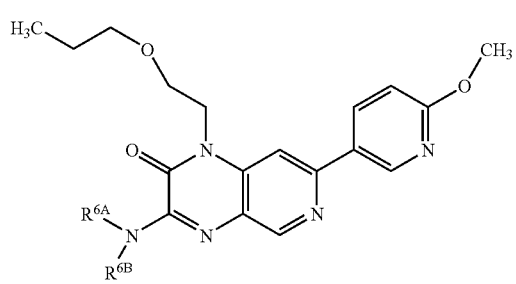
(I-18)
TABLE A-continued
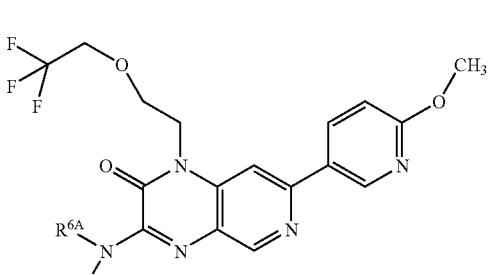
(I-19)
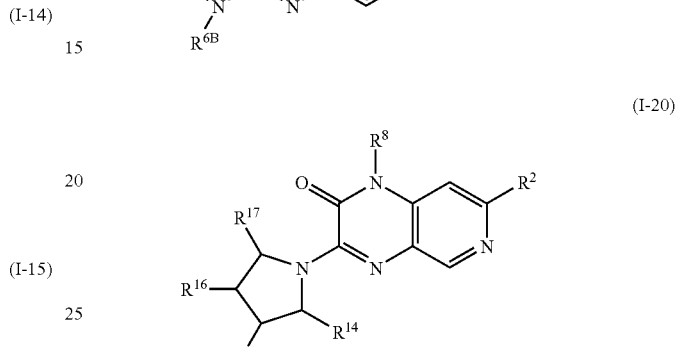
(I-20)
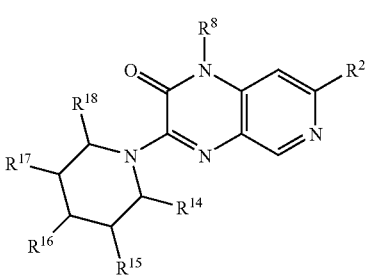
(I-21)
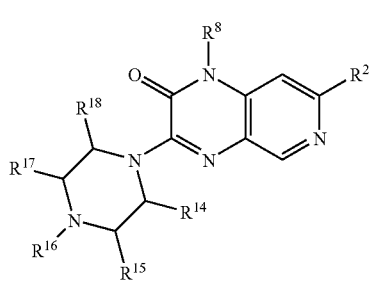
(I-22)
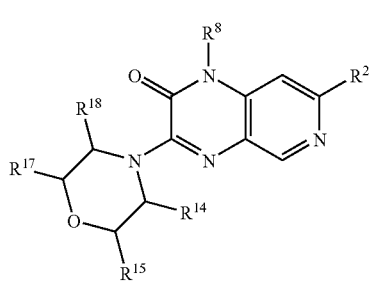
(I-23)

TABLE A-continued
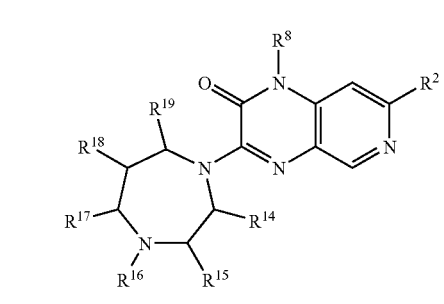
(I-24)
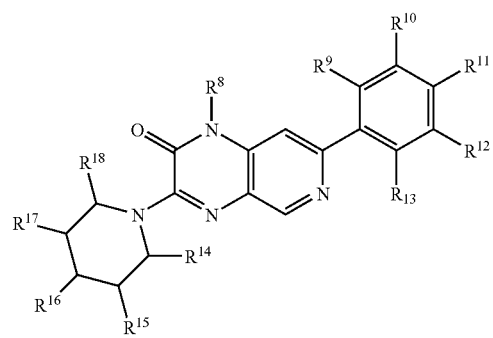
(I-25)
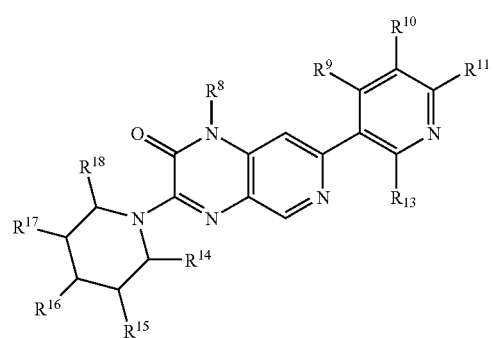
(I-26)
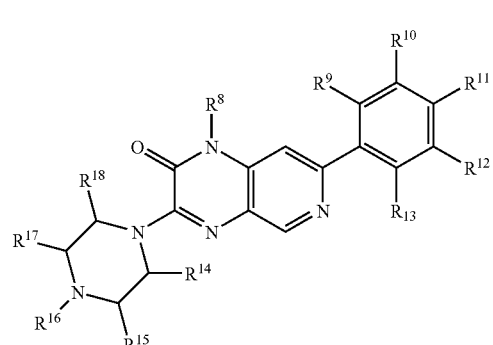
(I-27)
TABLE A-continued
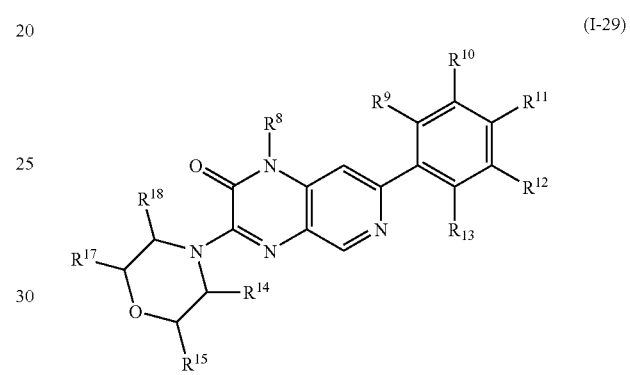
(I-28)
(I-29)
(I-30)
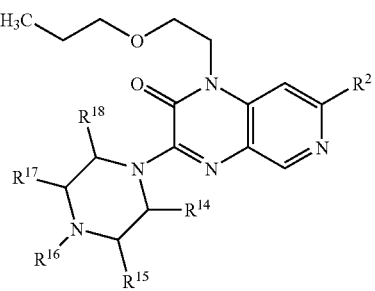
(I-31)

TABLE A-continued

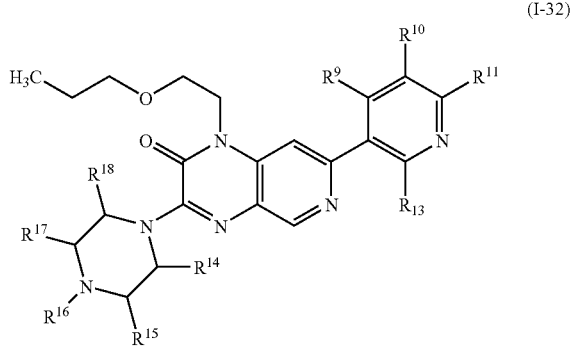

(I-32)

wherein $R^9$, $R^{10}$, $R^{11}$, $R^{12}$, $R^{13}$ are selected from the group consisting of hydrogen, halogen, $C_1$ to $C_4$ alkyl, $-OR^{201}$, and $-NR^{201}R^{202}$; wherein (a) when the alkyl is methyl, the methyl may be optionally substituted with 1, 2, or 3 halogen substituents, (b) when the alkyl comprises at least two carbon atoms, the alkyl may be optionally substituted with one or more substituents selected from the group consisting of halogen, oxo, $C_1$ to $C_2$ alkoxy and hydroxy; and wherein $R^{201}$ and $R^{202}$ are independently selected from the group consisting of hydrogen and $C_1$ to $C_2$ alkyl; and $R^{14}$, $R^{15}$, $R^{16}$, $R^{17}$, $R^{18}$ and $R^{19}$ are selected from the group consisting of hydrogen, halogen, alkyl, and $-OR^{601}$, wherein (a) said alkyl substituent may be optionally substituted with one or more substituents independently selected from the group consisting of halogen, $-OR^{603}$, $-C(O)R^{603}$, $-C(O)OR^{603}$, $-NR^{603}R^{604}$, and $-C(O)NR^{603}R^{604}$; and $R^{601}$, $R^{603}$ and $R^{604}$ are independently selected from the group consisting of hydrogen and alkyl.

In another embodiment, $R^9$, $R^{10}$, $R^{11}$, $R^{12}$, $R^{13}$ are selected from the group consisting of hydrogen, halogen, $C_1$ to $C_4$ alkyl, $-OR^{201}$, and $-NR^{201}R^{202}$; wherein (a) when the alkyl is methyl, the methyl may be optionally substituted with 1, 2, or 3 halogen substituents, (b) when the alkyl comprises at least two carbon atoms, the alkyl may be optionally substituted with one or more substituents selected from the group consisting of halogen, oxo, $C_1$ to $C_2$ alkoxy and hydroxy; and wherein $R^{201}$ and $R^{202}$ are independently selected from the group consisting of hydrogen and $C_1$ to $C_2$ alkyl.

In another embodiment, $R^9$, $R^{10}$, $R^{11}$, $R^{12}$, $R^{13}$ are selected from the group consisting of hydrogen, chloro, fluoro, methyl, ethyl, propyl, butyl, pentyl, hexyl, trifluoromethyl, hydroxy, methoxy, ethoxy, propoxy, butoxy, amino, methylamino, dimethylamino, ethylamino, and diethylamino.

In another embodiment, $R^{14}$, $R^{15}$, $R^{16}$, $R^{17}$, $R^{18}$ and $R^{19}$ are selected from the group consisting of hydrogen, alkyl, and $-OR^{601}$, wherein (a) said alkyl substituent may be optionally substituted with one or more substituents independently selected from the group consisting of $-OR^{603}$, $-C(O)R^{603}$, $-C(O)OR^{603}$, and $-C(O)NR^{603}R^{604}$ and $R^{601}$, $R^{603}$ and $R^{604}$ are independently selected from the group consisting of hydrogen and alkyl.

In another embodiment, $R^{14}$, $R^{15}$, $R^{16}$, $R^{17}$, $R^{18}$ and $R^{19}$ are selected from the group consisting of hydrogen, OH, $-CH_3$, $-CH_2CH_3$, $-CH_2CH_2CH_3$, $-CH_2CH_2CH_2CH_3$, $-CH(CH_3)CH_3$, $-C(CH_3)_2CH_3$, $-C(CH_3)_3$, $-CH_2OH$, $-CH_2CH_2OH$, $-CH_2CH_2CH_2OH$, $-CH_2CH(CH_3)OH$, $-CH(CH_3)CH(CH_3)OH$, $-CH_2C(CH_3)_2OH$, $-CH_2C(O)OH$, $-CH_2C(O)OC(CH_3)_3$, and $-C(O)NH_2$.

Embodiments of $R^2$ Substituent

In one embodiment of Formula I, $R^2$ is selected from the group consisting of aryl and 3 to 10 membered ring heterocycyl wherein $R^2$ may be optionally substituted as provided in Formula I.

In one embodiment of Formula I, $R^2$ is selected from the group consisting of phenyl and a 3 to 10 membered ring heteroaryl, optionally substituted as provided in Formula I. In another embodiment of Formula I, $R^2$ is selected from the group consisting of phenyl and a 5 to 7 membered ring heterocyclyl, optionally substituted as provided in Formula I. In another embodiment of Formula I, $R^2$ is selected from the group consisting of phenyl and a 5 to 7 membered ring heteroaryl, optionally substituted as provided in Formula I. In another embodiment of Formula I, $R^2$ is selected from the group consisting of phenyl and a 5 to 6 membered ring heteroaryl, optionally substituted as provided in Formula I. In another embodiment of Formula I, $R^2$ is a 5 to 6 membered ring heteroaryl that comprises 1, 2, or 3 ring heteroatoms selected from the group consisting of oxygen and nitrogen.

In one embodiment of Formula I, $R^2$ is selected from the group consisting of phenyl, thienyl, furanyl, thiazolyl, imidazolyl, pyrazolyl, isoxazolyl, isothiazolyl, pyrazinyl pyridinyl, triazinyl, imidazyl, thiophenyl, pyrazolyl, oxazolyl, oxadiazolyl, pyridyl, pyrazyl, pyrimidinyl, pyridazinyl, benzofuran, and benzodioxolyl. In another embodiment of Formula I, $R^2$ is selected from the group consisting of phenyl, pyridinyl, pyrimidinyl, isoxazolyl, pyrazolyl, benzofuran, and benzodioxolyl, optionally substituted as provided in Formula I. In another embodiment of Formula I, $R^2$ is selected from the group consisting of phenyl, thienyl, and pyridinyl optionally substituted as provided in Formula I.

In another embodiment of Formula I, $R^2$ is selected from the group consisting of phenyl,

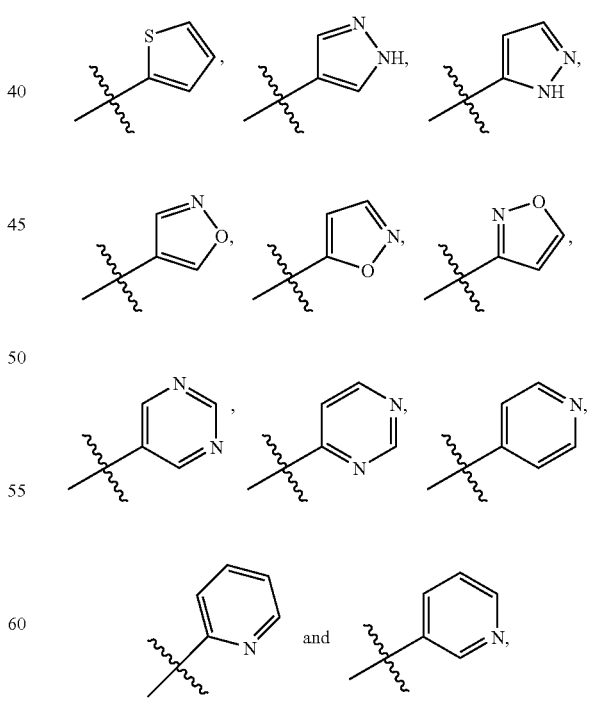

each optionally substituted as provided in Formula I. In another embodiment of Formula I, $R^2$ is selected from the group consisting of phenyl,

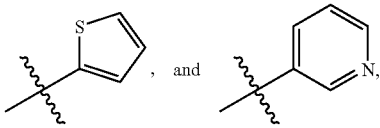, and each optionally substituted as provided in Formula I. In another embodiment of Formula I, R² is selected from the group consisting of phenyl,

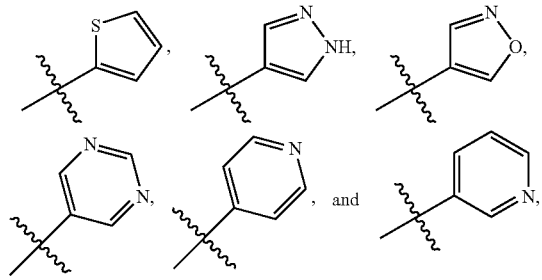

each optionally substituted as provided in Formula I. In another embodiment of Formula I, R² is selected from the group consisting of phenyl,

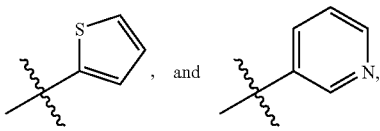, and each optionally substituted as provided in Formula I. In another embodiment of Formula I, R² is selected from the group consisting of phenyl and pyridinyl, each optionally substituted as provided in Formula I. In another embodiment of Formula I, R² is phenyl optionally substituted as provided in Formula I. In another embodiment of Formula I, R² is pyridinyl optionally substituted as provided in Formula I. In another embodiment of Formula I, R² is selected from the group consisting of phenyl and

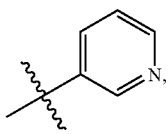

each optionally substituted as provided in Formula I. In another embodiment of Formula I, R² is selected from the group consisting of

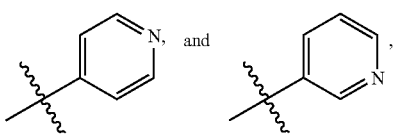, and each optionally substituted as provided in Formula I. In another embodiment, R² is 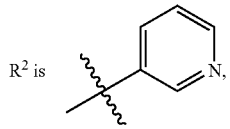

optionally substituted as provided in Formula I-1.

In one embodiment of Formula I, R² may be optionally substituted with one or more substituents selected from the group consisting of halogen, oxo, alkyl, —OR²⁰¹, —C(O)R²⁰¹, —OC(O)R²⁰¹, —C(O)OR²⁰¹, —NR²⁰¹R²⁰² and —C(O)NR²⁰¹R²⁰², wherein the alkyl substituent may be optionally substituted with one or more substituents independently selected from the group consisting of halogen, oxo, —OR²⁰³, and —C(O)OR²⁰³; wherein R²⁰¹, R²⁰², and R²⁰³ are independently selected from the group consisting of hydrogen and C₁ to C₄ alkyl.

In another embodiment of Formula I, R² may be optionally substituted with one or more substituents independently selected from the group consisting of halogen, cyano, oxo, C₁ to C₄ alkyl, —OR²⁰¹, —NR²⁰¹R²⁰², —C(O)OR²⁰¹, and —C(O)NR²⁰¹R²⁰², wherein (a) when the alkyl is methyl, the methyl may be optionally substituted with 1, 2, or 3 halogen substituents, (b) when the alkyl comprises at least two carbon atoms, the alkyl may be optionally substituted with one or more substituents selected from the group consisting of halogen, C₁ to C₄ alkoxy and hydroxy; and wherein R²⁰¹ and R²⁰² are independently selected from the group consisting of hydrogen and C₁ to C₂ alkyl.

In another embodiment of Formula I, R² may be optionally substituted with one or more substituents selected from the group consisting of halogen, C₁ to C₄ alkyl, —OR²⁰¹, and —NR²⁰¹R²⁰²; wherein (a) when the alkyl is methyl, the methyl may be optionally substituted with 1, 2, or 3 halogen substituents, (b) when the alkyl comprises at least two carbon atoms, the alkyl may be optionally substituted with one or more substituents selected from the group consisting of halogen, oxo, C₁ to C₂ alkoxy and hydroxy; and wherein R²⁰¹ and R²⁰² are independently selected from the group consisting of hydrogen and C₁ to C₂ alkyl.

In one embodiment of Formula I, R² may be optionally substituted with one or more substituents selected from the group consisting of chloro, fluoro, methyl, ethyl, propyl, butyl, pentyl, hexyl, trifluoromethyl, hydroxy, methoxy, ethoxy, propoxy, butoxy, amino, methylamino, dimethylamino, ethylamino, and diethylamino. In another embodiment of Formula I, R² may be optionally substituted with one or more substituents selected from the group consisting of fluoro, methyl, trifluoromethyl, methoxy, trifluoromethoxy, amino, methylamino, and dimethylamino.

In one embodiment of Formula I, R² is substituted with one or more fluoro substituents. In another embodiment of Formula I, R² is substituted with one fluoro substituent. In another embodiment of Formula I, R² is substituted with two fluoro substituents.

In one embodiment of Formula I, R² is substituted with methoxy.

In one embodiment of Formula I, R² is substituted at the para position with a substituent selected from the group consisting of fluoro, methyl, trifluoromethyl, methoxy, trifluoromethoxy, amino, methylamino, and dimethylamino. In another embodiment of Formula I, R² is substituted at the para position with a substituent selected from the group consisting of fluoro, methyl, trifluoromethyl, methoxy, and trifluoromethoxy. In another embodiment of Formula I, R² is substituted at the para position with methoxy.

In one embodiment of Formula I, R² is selected from the group in Table A consisting of Formula I-1, Formula I-5, Formula I-6, and Formula I-11, wherein R⁹, R¹⁰, R¹¹, R¹² and R¹³ are independently selected from the group consisting of hydrogen, halogen, oxo, alkyl, —OR²⁰¹, —C(O)R²⁰¹, —OC(O)R²⁰¹, —C(O)OR²⁰¹, —NR²⁰¹R²⁰² and —C(O)NR²⁰¹R²⁰², wherein the alkyl substitutent may be optionally substituted with one or more substituents independently selected from the group consisting of halogen, oxo, —OR²⁰³, and —C(O)OR²⁰³; wherein R²⁰¹, R²⁰², and R²⁰³ are independently selected from the group consisting of hydrogen and C₁ to C₄ alkyl. In another embodiment of Formula I, R² is selected from the group in Table A consisting of Formula I-1 and Formula I-6, wherein R⁹, R¹⁰, R¹¹, R¹² and R¹³ are independently selected from the group consisting of hydrogen, halogen, oxo, alkyl, —OR²⁰¹, —C(O)R²⁰¹, —OC(O)R²⁰¹, —C(O)OR²⁰¹, —NR²⁰¹R²⁰² and —C(O)NR²⁰¹R²⁰², wherein the alkyl substitutent may be optionally substituted with one or more substituents independently selected from the group consisting of halogen, oxo, —OR²⁰³, and —C(O)OR²⁰³; wherein R²⁰¹, R²⁰², and R²⁰³ are independently selected from the group consisting of hydrogen and C₁ to C₄ alkyl. In another embodiment of Formula I, R² is selected from the group in Table A consisting of Formula I-1, and Formula I-5, wherein R⁹, R¹⁰, R¹¹, R¹² and R¹³ are independently selected from the group consisting of hydrogen, halogen, alkyl, haloalkyl, oxy, alkoxy, hydroxy, and carboxy. In another embodiment of Formula I, R² is selected from the group in Table A consisting of Formula I-1, and Formula I-6, wherein R⁹, R¹⁰, R¹¹, R¹² and R¹³ are independently selected from the group consisting of hydrogen, fluoro, methyl, trifluoromethyl, and methoxy. In another embodiment of Formula I, R² is selected from the group in Table A consisting of Formula I-1 and Formula I-6, wherein R⁹, R¹⁰, R¹¹, R¹² and R¹³ are independently selected from the group consisting of hydrogen, fluoro, methyl, trifluoromethyl, and methoxy.

In another embodiment of Formula I, R² is as provided in Formula I-3 in Table A, wherein R¹¹ is selected from the group consisting of hydrogen, fluoro, methyl, trifluoromethyl, and methoxy. In another embodiment of Formula I, the R² substituent is as provided in Formula I-4 in Table A.

Embodiments of —NR⁶ᴬR⁶ᴮ Substituent

In one embodiment of Formula I, R⁶ᴬ and R⁶ᴮ together with the nitrogen to which they are attached form a partially or fully saturated 3 to 14 membered ring heterocyclyl, optionally substituted as provided in Formula I. In another embodiment, R⁶ᴬ and R⁶ᴮ together with the nitrogen to which they are attached form a partially or fully saturated 5 to 7 membered ring heterocyclyl, optionally substituted as provided in Formula I. In another embodiment, R⁶ᴬ and R⁶ᴮ together with the nitrogen to which they are attached form a partially or fully saturated 5 to 6 membered ring heterocyclyl, optionally substituted as provided in Formula I.

In one embodiment of Formula I, R⁶ᴬ and R⁶ᴮ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted as provided in Formula I.

In another embodiment, R⁶ᴬ and R⁶ᴮ together with the nitrogen to which they are attached form a heterocyclyl selected from the group consisting of

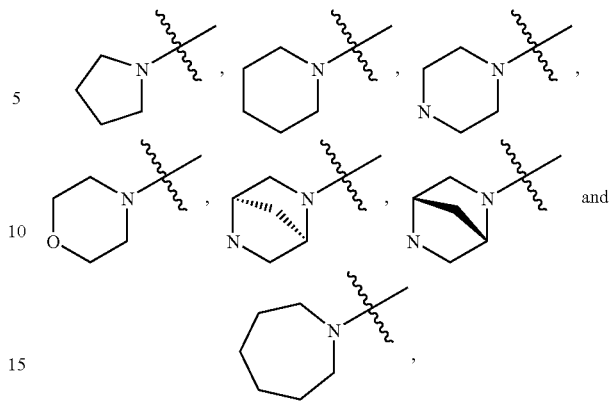

each optionally substituted as provided in Formula I.

In another embodiment, R⁶ᴬ and R⁶ᴮ together with the nitrogen to which they are attached form a heterocyclyl selected from the group consisting of

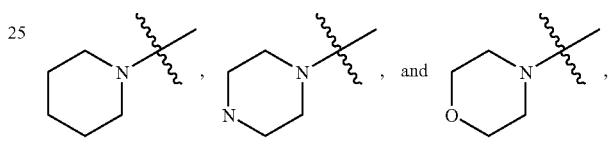

each optionally substituted as provided in Formula I. In another embodiment, R⁶ᴬ and R⁶ᴮ together with the nitrogen to which they are attached form a piperazinyl as provided in Formula I-22.

In one embodiment, the R⁶ᴬ and R⁶ᴮ heterocyclyl may be optionally substituted with one or more substituents independently selected from the group consisting of hydrogen, halogen, cyano, oxo, alkyl, —OR⁶⁰¹, —C(O)R⁶⁰¹, —C(O)OR⁶⁰¹, —NR⁶⁰¹R⁶⁰², —N(R⁶⁰¹)C(O)R⁶⁰², —C(O)NR⁶⁰¹R⁶⁰², wherein (a) said alkyl substituent may be optionally substituted with one or more substituents independently selected from the group consisting of halogen, —OR⁶⁰³, —C(O)R⁶⁰³, —C(O)OR⁶⁰³, —NR⁶⁰³R⁶⁰⁴, and —C(O)NR⁶⁰³R⁶⁰⁴; and R⁶⁰¹, R⁶⁰², R⁶⁰³ and R⁶⁰⁴ are independently selected from the group consisting of hydrogen and alkyl, wherein (a) said R⁶⁰¹ and R⁶⁰² alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

In another embodiment, the R⁶ᴬ and R⁶ᴮ heterocyclyl may be optionally substituted with one or more substituents independently selected from the group consisting of hydrogen, halogen, alkyl, and —OR⁶⁰¹, wherein (a) said alkyl substituent may be optionally substituted with one or more substituents independently selected from the group consisting of halogen, —OR⁶⁰³, —C(O)R⁶⁰³, —C(O)OR⁶⁰³, —NR⁶⁰³R⁶⁰⁴, and —C(O)NR⁶⁰³R⁶⁰⁴; and R⁶⁰¹, R⁶⁰³ and R⁶⁰⁴ are independently selected from the group consisting of hydrogen and alkyl.

In another embodiment, the R⁶ᴬ and R⁶ᴮ heterocyclyl may be optionally substituted with one or more substituents independently selected from the group consisting of hydrogen, halogen, alkyl, and —OR⁶⁰¹, wherein (a) said alkyl substituent may be optionally substituted with one or more substituents independently selected from the group consisting of halogen, —OR$^{603}$, —C(O)R$^{603}$, —C(O)OR$^{603}$, —NR$^{603}$R$^{604}$, and —C(O)NR$^{603}$R$^{604}$; and R$^{601}$, R$^{603}$ and R$^{604}$ are independently selected from the group consisting of hydrogen and alkyl.

In another embodiment, the R$^{6A}$ and R$^{6B}$ heterocyclyl may be optionally substituted with one or more substituents independently selected from the group consisting of hydrogen, alkyl, and —OR$^{601}$, wherein (a) said alkyl substituent may be optionally substituted with one or more substituents independently selected from the group consisting of —OR$^{603}$, —C(O)R$^{603}$, —C(O)OR$^{603}$, and —C(O)NR$^{603}$R$^{604}$; and R$^{601}$, R$^{603}$ and R$^{604}$ are independently selected from the group consisting of hydrogen and alkyl.

In another embodiment, the R$^{6A}$ and R$^{6B}$ heterocyclyl may be optionally substituted with one or more substituents independently selected from the group consisting of hydrogen, hydroxy, alkyl, hydroxyalkyl, alkylcarboxyalkyl, carboxyalkyl, and aminocarbonyl.

In another embodiment, the R$^{6A}$ and R$^{6B}$ heterocyclyl may be optionally substituted with one or more substituents independently selected from the group consisting of hydrogen, —OH, —CH$_3$, —CH$_2$CH$_3$, —CH$_2$CH$_2$CH$_3$, —CH$_2$CH$_2$CH$_2$CH$_3$, —CH(CH$_3$)CH$_3$, —C(CH$_3$)$_2$CH$_3$, —C(CH$_3$)$_3$, —CH$_2$OH, —CH$_2$CH$_2$OH, —CH$_2$CH$_2$CH$_2$OH, —CH$_2$CH(CH$_3$)OH, —CH(CH$_3$)CH(CH$_3$)OH, —CH$_2$C(CH$_3$)$_2$OH, —CH$_2$C(O)OH, —CH$_2$C(O)OC(CH$_3$)$_3$, and —C(O)NH$_2$. In another embodiment, the R$^{6A}$ and R$^{6B}$ heterocyclyl may be optionally substituted with one or more substituents independently selected from the group consisting of hydrogen, —OH, —CH$_3$, —CH$_2$CH$_3$, —CH$_2$OH, —CH$_2$CH$_2$OH, —CH$_2$CH$_2$CH$_2$OH, —CH$_2$CH(CH$_3$)OH, —CH$_2$(CH$_3$)CH(CH$_3$)OH, and —CH$_2$C(CH$_3$)$_2$OH.

In another embodiment, the R$^{6A}$ and R$^{6B}$ heterocyclyl may be optionally substituted with one or more substituents independently selected from the group consisting of hydrogen and —CH$_2$CH$_2$OH. In another embodiment, the R$^{6A}$ and R$^{6B}$ heterocyclyl may be optionally substituted with one or more —CH$_2$CH$_2$OH.

Embodiments of R$^8$ Substituent

In one embodiment of Formula I, R$^8$ is C$_1$ to C$_{10}$ alkyl, optionally substituted as provided in Formula I. In another embodiment of Formula I, R$^8$ is C$_1$ to C$_8$ alkyl, optionally substituted as provided in Formula I. In another embodiment of Formula I, R$^8$ is C$_1$ to C$_6$ alkyl, optionally substituted as provided in Formula I. In another embodiment of Formula I, R$^8$ is C$_1$ to C$_4$ alkyl, optionally substituted as provided in Formula I. In another embodiment of Formula I, R$^8$ is ethyl, optionally substituted as provided in Formula I.

In one embodiment of Formula I, R$^8$ is substituted with —OR$^{801}$, wherein R$^{801}$ is as provided in Formula I. In another embodiment of Formula I, R$^8$ may be optionally substituted with one or more substituents independently selected from the group consisting of halogen and —OR$^{801}$, wherein R$^{801}$ is selected from the group consisting of hydrogen and C$_1$ to C$_6$ alkyl, wherein (a) when the C$_1$ to C$_6$ alkyl is methyl, the methyl may be optionally substituted with 1, 2, or 3 fluoro substituents, (b) when the C$_1$ to C$_6$ alkyl comprises at least two carbon atoms, the alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

In another embodiment of Formula I, R$^{801}$ is C$_2$ to C$_4$ alkyl optionally substituted with one or more substituents independently selected from the group consisting of halogen, hydroxy, carboxy, alkoxy, haloalkyl, hydroxyalkyl, carboxyalkyl, haloalkoxy, hydroxyalkoxy, and carboxyalkoxy. In another embodiment of Formula I, R$^8$ may be optionally substituted with one or more substituents independently selected from the group consisting of halogen, haloalkoxy, hydroxy, and alkoxy. In another embodiment of Formula I, R$^8$ may be optionally substituted with one or more substituents independently selected from the group consisting of haloalkoxy and alkoxy. In another embodiment of Formula I, R$^8$ is ethyl optionally substituted with one or more substituents independently selected from the group consisting of halogen, haloalkoxy, hydroxy, carboxy, and alkoxy. In another embodiment of Formula I, R$^8$ is ethyl optionally substituted with one or more substituents independently selected from the group consisting of haloalkoxy and alkoxy.

In another embodiment of Formula I, R$^8$ is alkyl substituted with —OR$^{801}$, wherein R$^{801}$ is as provided in Formula I.

In another embodiment of Formula I, R$^8$ is alkoxyalkyl, optionally substituted as provided in Formula I.

In another embodiment of Formula I, R$^8$ is a (C$_1$ to C$_4$)alkoxy(C$_1$ to C$_4$)alkyl, optionally substituted as provided in Formula I.

In another embodiment of Formula I, R$^8$ is methoxyethyl, as provided in Formula I-13 in Table A.

In another embodiment of Formula I, R$^8$ is ethoxyethyl, as provided in Formula I-14 in Table A.

In another embodiment of Formula I, R$^8$ is propoxyethyl, as provided in Formula I-15 in Table A.

In another embodiment of Formula I, R$^8$ is trifluoroethylethoxy as provided in Formula I-16 in Table A.

Additional Embodiments

The following are additional embodiments of the compounds of Formula I. Unless otherwise specified, substituents are as provided in Formula I. Further embodiments of Formula I provided when R$^2$, R$^{6A}$, R$^{6B}$ and R$^8$ are selected from the various embodiments provided above.

Embodiments where R$^8$ is Alkyl Substituted with —OR$^{801}$, R$^2$ is Phenyl or 5 to 6 Membered Heteroaryl In one embodiment of Formula I, R$^2$ is selected from the group consisting of phenyl and 5 to 6 membered ring heterocycyl, wherein the R$^2$ phenyl and heterocyclyl may be optionally substituted as provided in Formula I, and R$^8$ is alkyl substituted with —OR$^{801}$, wherein R$^{801}$ is as provided in Formula I.

In one embodiment of Formula I, R$^2$ is selected from the group consisting of phenyl and 5 to 6 membered ring heteroaryl, wherein the R$^2$ phenyl and heteroaryl may be optionally substituted as provided in Formula I, and R$^8$ is alkyl substituted with —OR$^{801}$, wherein R$^{801}$ is as provided in Formula I. In another embodiment of Formula I, R$^2$ is selected from the group consisting of phenyl and 5 to 6 membered ring heteroaryl, wherein the R$^2$ phenyl and heterocyclyl may be optionally substituted as provided in Formula I, and R$^8$ is alkoxyalkyl, wherein the R$^8$ alkoxyalkyl may be optionally substituted as provided in Formula I.

In another embodiment of Formula I, R$^2$ is selected from the group consisting of phenyl, thienyl, pyridinyl, and isoquinolinyl wherein the R$^2$ phenyl, thienyl, pyridinyl, and isoquinolinyl may be optionally substituted as provided in Formula I, and R$^8$ is a (C$_1$ to C$_4$)alkoxy(C$_1$ to C$_4$)alkyl, wherein the R$^8$ alkoxyalkyl may be optionally substituted as provided in Formula I.

In another embodiment of Formula I, R$^2$ is selected from the group consisting of phenyl, thienyl and pyridinyl, wherein the R$^2$ phenyl, thienyl and pyridinyl may be optionally substituted as provided in Formula I, and R$^8$ is selected from the group consisting of methoxyethyl, ethoxyethyl, propoxyethyl, and trifluoroethoxyethyl.

In another embodiment of Formula I, $R^2$ is selected from the group consisting of phenyl and pyridinyl, wherein the $R^2$ phenyl and pyridinyl may be optionally substituted as provided in Formula I, and $R^8$ is selected from the group consisting of methoxyethyl, ethoxyethyl, propoxyethyl, and trifluoroethylethoxy.

In another embodiment of Formula I, $R^2$ is selected from the group consisting of phenyl and pyridinyl, wherein the $R^2$ phenyl and pyridinyl may be optionally substituted with one or more substituents independently selected from the group consisting of hydrogen, fluoro, chloro, methyl, methoxy, ethoxy, isopropoxy, hydroxy, hydroxymethyl, ethanone, dimethylamino and ethylsulfonyl and $R^8$ is selected from the group consisting of methoxyethyl, ethoxyethyl, propoxyethyl and trifluoroethylethoxy.

In another embodiment of Formula I, $R^2$ is selected from the group consisting of phenyl and pyridinyl, wherein the $R^2$ phenyl and pyridinyl may be optionally substituted with one or more substituents independently selected from the group consisting of hydrogen, fluoro, chloro, methyl, and methoxy and $R^8$ is selected from the group consisting of methoxyethyl, ethoxyethyl, and propoxyethyl.

In another embodiment of Formula I, $R^2$ is pyridinyl, optionally substituted with methoxy, and $R^8$ is propoxyethyl.

In another embodiment, $R^2$ and $R^8$ are as provided in Formula I-18 of Table A.

Embodiments where $R^{6A}$ and $R^{6B}$ Together with the Nitrogen to which They are Attached Form a Partially or Fully Saturated 5 to 7 Membered Ring Heterocyclyl and $R^8$ is Alkyl Substituted with —$OR^{801}$ In one embodiment, $R^{6A}$ and $R^{6B}$ together with the nitrogen to which they are attached is a partially or fully saturated 5 to 7 membered ring heterocyclyl, wherein the 5 to 7 membered ring heterocyclyl may be optionally substituted as provided in Formula I, and $R^8$ is alkyl substituted with —$OR^{801}$, wherein $R^{801}$ is as provided in Formula I.

In another embodiment, $R^{6A}$ and $R^{6B}$ together with the nitrogen to which they are attached form a partially or fully saturated 5 to 7 membered ring heterocyclyl heterocycyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted as provided in Formula I, and $R^8$ is alkyl substituted with —$OR^{801}$, wherein $R^{801}$ is as provided in Formula I.

In another embodiment, $R^{6A}$ and $R^{6B}$ together with the nitrogen to which they are attached form a partially or fully saturated 5 to 7 membered ring heterocyclyl heterocycyl selected from the group consisting of piperadinyl, piperazinyl, and morpholinyl, wherein the piperadinyl, piperazinyl, and morpholinyl may be optionally substituted as provided in Formula I, and $R^8$ is alkyl substituted with —$OR^{801}$, wherein $R^{801}$ is as provided in Formula I.

In another embodiment, $R^{6A}$ and $R^{6B}$ together with the nitrogen to which they are attached forms a piperadinyl optionally substituted as provided in Formula I, and $R^8$ is alkyl substituted with —$OR^{801}$, wherein $R^{801}$ is as provided in Formula I.

In another embodiment, $R^{6A}$ and $R^{6B}$ together with the nitrogen to which they are attached forms a piperazinyl optionally substituted as provided in Formula I, and $R^8$ is alkyl substituted with —$OR^{801}$, wherein $R^{801}$ is as provided in Formula I.

Embodiments where $R^2$ is Phenyl or 5 to 6 Membered Heteroaryl, $R^{6A}$ and $R^{6B}$ Together with the Nitrogen to which they are Attached Form a 5 to 7 Membered Fully Saturated Heterocyclyl, and $R^8$ is Alkyl Substituted with —$OR^{801}$ In one embodiment of Formula I, $R^2$ is selected from the group consisting of phenyl and 5 to 6 membered ring heteroaryl, wherein the $R^2$ phenyl and heteroaryl may be optionally substituted as provided in Formula I; $R^{6A}$ and $R^{6B}$ together with the nitrogen to which they are attached is a partially or fully saturated 5 to 7 membered ring heterocyclyl, wherein the 5 to 7 membered ring heterocyclyl may be optionally substituted as provided in Formula I; and $R^8$ is alkyl substituted with —$OR^{801}$, wherein $R^{801}$ is as provided in Formula I.

In another embodiment of Formula I, $R^2$ is selected from the group consisting of phenyl, thienyl, pyridinyl, and isoquinolinyl, wherein the $R^2$ phenyl, thienyl, pyridinyl, and isoquinolinyl may be optionally substituted as provided in Formula I; $R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted as provided in Formula I; and $R^8$ is alkyl substituted with —$OR^{801}$, wherein $R^{801}$ is as provided in Formula I.

Embodiments where $R^2$ is Phenyl, Thienyl or Pyridinyl, $R^{6A}$ and $R^{6B}$ Together with the Nitrogen to which they are Attached Form a Partially of Fully Saturated 5 to 7 Membered Ring Heterocyclyl, and $R^8$ is Alkyl Substituted with —$OR^{801}$ In one embodiment of Formula I, $R^2$ is selected from the group consisting of phenyl, thienyl, and pyridinyl, wherein the $R^2$ phenyl, thienyl, and pyridinyl may be optionally substituted with one or more substituents independently selected from the group consisting of halogen, cyano, nitro, oxo, alkyl, alkenyl, —$OR^{201}$, —$C(O)R^{201}$, —$C(O)OR^{201}$, —$NR^{201}R^{202}$, and —$S(O)_2R^{201}$; wherein said alkyl and alkenyl substituents may be optionally substituted with one or more substituents independently selected from the group consisting of halogen, oxo, —$OR^{203}$, and —$C(O)OR^{203}$; and $R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy and alkoxy;

$R^{6A}$ and $R^{6B}$ together with the nitrogen to which they are attached form a partially or fully saturated 5 to 7 membered ring heterocyclyl, wherein the 5 to 7 membered ring heterocyclyl may be optionally substituted with one or more substituents independently selected from the group consisting of hydrogen, halogen, cyano, oxo, alkyl, —$OR^{601}$, —$C(O)R^{601}$, —$C(O)OR^{601}$, —$NR^{601}R^{602}$, —$N(R^{601})C(O)R^{602}$, and —$C(O)NR^{601}R^{602}$, wherein (a) said alkyl substituent may be optionally substituted with one or more substituent selected from the group consisting of halogen, —$OR^{603}$, —$C(O)R^{603}$, —$C(O)OR^{603}$, —$NR^{603}R^{604}$, and —$C(O)NR^{603}R^{604}$; and $R^{601}$, $R^{602}$, $R^{603}$ and $R^{604}$ are independently selected from the group consisting of hydrogen and alkyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy;

$R^8$ is alkyl substituted with —$OR^{801}$; and $R^{801}$ is selected from the group consisting of hydrogen and alkyl wherein (a) when said alkyl is methyl, said methyl may be optionally substituted with 1, 2, or 3 fluoro substituents, (b) when said alkyl comprises at least two carbon atoms, said alkyl may be optionally substituted with one or more substituents independently selected from the group consisting of halogen, hydroxy, carboxy, oxo, and alkynyl.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents and $R^2$ is selected from the group consisting of phenyl, thienyl, and pyridinyl, wherein the $R^2$ phenyl, thienyl, and pyridinyl may be optionally substituted with one or more substituents independently selected from the group consisting of hydroxy, halogen, alkyl, —$OR^{201}$, —$C(O)R^{201}$, $NR^{201}R^{202}$, and —$S(O)_2R^{201}$; wherein said alkyl may be optionally substituted with one or more —$OR^{203}$, and $R^{201}$, $R^{202}$ and $R^{203}$ are independently selected from the group consisting of hydrogen and alkyl. In another embodiment, the $R^2$ phenyl, thienyl, and pyridinyl may be optionally substituted with one or more substituents independently selected from the group consisting of hydroxy, chloro, fluoro, methyl, methoxy, ethoxy, hydroxymethyl, —$C(O)CH_3$, —$C(O)CH(CH_3)_2$, —$N(CH_3)_2$, and —$S(O)_2CH_2(CH_3)$.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents and $R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of halogen, alkyl, —$OR^{601}$, and —$C(O)NR^{601}R^{602}$, wherein said alkyl substituent may be optionally substituted with one or more substituent selected from the group consisting of —$OR^{603}$, —$C(O)OR^{603}$, and —$NR^{603}R^{604}$; and $R^{601}$, $R^{602}$, $R^{603}$ and $R^{604}$ are independently selected from the group consisting of hydrogen and alkyl. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents and $R^{6A}$ and $R^{6B}$ together with the nitrogen to which they are attached form a heterocyclyl selected from the group consisting of piperadinyl, piperazinyl and morpholinyl wherein the piperadinyl, piperazinyl and morpholinyl may be optionally substituted with one or more substituents independently selected from the group consisting of chloro, hydroxy, methyl, ethyl, propyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents and $R^{6A}$ and $R^{6B}$ together with the nitrogen to which they are attached form a piperazinyl wherein the piperazinyl may be optionally substituted with one or more substituents independently selected from the group consisting of chloro, hydroxy, methyl, ethyl, propyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is selected from the group consisting of phenyl and pyridinyl, wherein the phenyl and pyridinyl may be optionally substituted with one or more substituents selected from the group consisting of hydroxy, chloro, fluoro, methyl, methoxy, ethoxy, hydroxymethyl, —$C(O)CH_3$, —$C(O)CH(CH_3)_2$, —$N(CH_3)_2$, and —$S(O)_2CH_2(CH_3)$, and $R^{6A}$ and $R^{6B}$ together with the nitrogen to which they are attached form a heterocyclyl selected from the group consisting of piperadinyl, piperazinyl, and morpholinyl wherein the piperadinyl, piperazinyl, and morpholinyl may be optionally substituted with one or more substituents selected from the group consisting of chloro, hydroxy, ethyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$.

In another embodiment, $R^2$ is pyridinyl substituted with methoxy; $R^{6A}$ and $R^{6B}$ together with the nitrogen to which they are attached form a piperazinyl, optionally substituted with one or more substituents selected from the group consisting of chloro, hydroxy, ethyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$; and $R^8$ is propoxyethyl. Embodiments where $R^2$ is Phenyl, Thienyl or Pyridinyl, $R^{6A}$ and $R^{6B}$ Together with the Nitrogen to which they are Attached Form a Pyrrolidinyl, Piperadinyl, Piperazinyl or Morpholino, and $R^8$ is Alkyl Substituted with —$OR^{801}$ In one embodiment of Formula I, $R^2$ is selected from the group consisting of phenyl, thienyl, and pyridinyl, wherein the $R^2$ phenyl, thienyl, and pyridinyl may be optionally substituted with one or more substituents independently selected from the group consisting of halogen, cyano, nitro, oxo, alkyl, alkenyl, —$OR^{201}$, —$C(O)R^{201}$, —$C(O)OR^{201}$, —$NR^{201}R^{202}$, and —$S(O)_2R^{201}$; wherein said alkyl and alkenyl substituents may be optionally substituted with one or more substituents independently selected from the group consisting of halogen, oxo, —$OR^{203}$, and —$C(O)OR^{203}$; and $R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy and alkoxy;

$R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of hydrogen, halogen, cyano, oxo, alkyl, —$OR^{601}$, —$C(O)R^{601}$, —$C(O)OR^{601}$, —$NR^{601}R^{602}$, —$N(R^{601})C(O)R^{602}$, and —$C(O)NR^{601}R^{602}$, wherein said alkyl substituent may be optionally substituted with one or more substituent selected from the group consisting of halogen, —$OR^{603}$, —$C(O)R^{603}$, —$C(O)OR^{603}$, —$NR^{603}R^{604}$, and —$C(O)NR^{603}R^{604}$; and $R^{601}$, $R^{602}$, $R^{603}$ and $R^{604}$ are independently selected from the group consisting of hydrogen and alkyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

$R^8$ is alkyl substituted with —$OR^{801}$; and $R^{801}$ is selected from the group consisting of hydrogen and alkyl wherein (a) when said alkyl is methyl, said methyl may be optionally substituted with 1, 2, or 3 fluoro substitutents, (b) when said alkyl comprises at least two carbon atoms, said alkyl may be optionally substituted with one or more substituents independently selected from the group consisting of halogen, hydroxy, carboxy, oxo, and alkynyl.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents and $R^{6A}$ and $R^{6B}$ together with the nitrogen to which they are attached form a heterocyclyl selected from the group consisting of piperadinyl, piperazinyl, and morpholinyl, wherein the piperadinyl, piperazinyl, and morpholinyl may be optionally substituted as provided above. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is selected from the group consisting of phenyl and pyridinyl, wherein the $R^2$ phenyl and pyridinyl may be optionally substituted as provided above, and $R^{6A}$ and $R^{6B}$ together with the nitrogen to which they are attached form a heterocyclyl selected from the group consisting of piperadinyl, piperazinyl, and morpholinyl, wherein the piperadinyl, piperazinyl, and morpholinyl may be optionally substituted as provided above. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is phenyl, wherein the phenyl may be optionally substituted as provided above, and $R^{6A}$ and $R^{6B}$ together with the nitrogen to which they are attached form a heterocyclyl selected from the group consisting of piperadinyl and piperazinyl, wherein the piperadinyl and piperazinyl may be optionally substituted as provided above. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is phenyl, optionally substituted as provided above, and $R^{6A}$ and $R^{6B}$ together with the nitrogen to which they are attached form a piperadinyl wherein the piperadinyl may be optionally substituted as provided above.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is pyridinyl, wherein the pyridinyl may be optionally substituted as provided above, and $R^{6A}$ and $R^{6B}$ together with the nitrogen to which they are attached form a heterocyclyl selected from the group consisting of piperadinyl and piperazinyl, wherein the piperadinyl and piperazinyl may be optionally substituted as provided above.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is pyridinyl, wherein the pyridinyl may be optionally substituted as provided above, and $R^{6A}$ and $R^{6B}$ together with the nitrogen to which they are attached form a piperazinyl wherein the piperazinyl may be optionally substituted as provided above.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is pyridinyl, wherein the pyridinyl may be optionally substituted as provided above, and $R^{6A}$ and $R^{6B}$ together with the nitrogen to which they are attached form a piperadinyl wherein the piperadinyl may be optionally substituted as provided above.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is selected from the group consisting of phenyl, thienyl and pyridinyl, wherein the $R^2$ phenyl, thienyl and pyridinyl may be optionally substituted with one or more substituents independently selected from the group consisting of hydroxy, halogen, alkyl, —$OR^{201}$, —$C(O)R^{201}$, —$NR^{201}R^{202}$, and $S(O)_2R^{201}$; wherein said alkyl may be optionally substituted with one or more —$OR^{203}$; and $R^{201}$, $R^{202}$, and $R^{201}$ are independently selected from the group consisting of hydrogen and alkyl. In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^2$ is selected from the group consisting of phenyl, thienyl and pyridinyl, wherein the $R^2$ phenyl, thienyl and pyridinyl may be optionally substituted with one or more substituents independently selected from the group consisting of hydroxy, chloro, fluoro, methyl, methoxy, ethoxy, hydroxymethyl, —$C(O)CH_3$, —$C(O)CH(CH_3)_2$, —$N(CH_3)_2$ and —$S(O)_2CH_2(CH_3)$).

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of hydrogen, halogen, alkyl, —$OR^{601}$, and —$C(O)NR^{601}R^{602}$, wherein said alkyl substituent may be may be optionally substituted with one or more substituent selected from the group consisting of —$OR^{603}$, —$C(O)OR^{603}$, and —$NR^{603}R^{604}$, and $R^{601}$, $R^{602}$, $R^{603}$, and $R^{604}$ are independently selected from the group consisting of hydrogen and alkyl.

In another embodiment, $R^8$ is $C_1$ to $C_4$ alkyl substituted with —$R^{801}$, wherein $R^{801}$ is $C_1$ to $C_4$ alkyl optionally substituted with 1, 2, or 3 fluoro substitutents; $R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of chloro, hydroxy, ethyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$.

In another embodiment, $R^2$ is selected from the group consisting of phenyl and pyridinyl, wherein the phenyl and pyridinyl may be optionally substituted with one or more substitutents selected from the group consisting of halogen, cyano, nitro, oxo, alkyl, alkenyl, —$OR^{201}$, —$C(O)R^{201}$, —$C(O)OR^{201}$, —$NR^{201}R^{202}$, and —$S(O)_2R^{201}$; wherein said alkyl and alkenyl substituents may be optionally substituted with one or more substituents independently selected from the group consisting of halogen, oxo, —$OR^{203}$, and —$C(O)OR^{203}$; and $R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy and alkoxy;

$R^{6A}$ and $R^{6B}$ together with the nitrogen to which they are attached form a heterocyclyl selected from the group consisting of piperadinyl, piperazinyl, and morpholinyl wherein the piperadinyl, piperazinyl, and morpholinyl may be optionally substituted with one or more substituents selected from the group consisting of hydrogen, halogen, cyano, oxo, alkyl, —$OR^{601}$, —$C(O)R^{601}$, —$C(O)OR^{601}$, —$NR^{601}R^{602}$, —$N(R^{601})C(O)R^{602}$, and —$C(O)NR^{601}R^{602}$, wherein (a) said alkyl substituent may be optionally substituted with one or more substituents selected from the group consisting of halogen, —$OR^{603}$, —$C(O)R^{603}$, —$C(O)OR^{603}$, and —$NR^{603}R^{604}$; and $R^{601}$, $R^{602}$, $R^{603}$ and $R^{604}$ are independently selected from the group consisting of hydrogen and alkyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

In another embodiment, $R^2$ is selected from the group consisting of phenyl and pyridinyl, wherein the phenyl and pyridinyl may be optionally substituted with hydroxy, halogen, alkyl, $-OR^{201}$, $-C(O)R^{201}$, $NR^{201}R^{202}$, and $-S(O)_2R^{201}$; wherein said alkyl may be optionally substituted with one or more $-OR^{203}$;

$R^{201}$, $R^{202}$ and $R^{203}$ are independently selected from the group consisting of hydrogen and alkyl;

$R^{6A}$ and $R^{6B}$ together with the nitrogen to which they are attached form a heterocyclyl selected from the group consisting of piperadinyl, piperazinyl, and morpholinyl wherein the piperadinyl, piperazinyl, and morpholinyl may be optionally substituted with one or more substituents selected from the group consisting of halogen, alkyl, $-OR^{601}$, and $-C(O)NR^{601}R^{602}$, wherein said alkyl substituent may be optionally substituted with one or more substituent selected from the group consisting of $-OR^{603}$, $-C(O)OR^{603}$, and $-NR^{603}R^{604}$; and $R^{601}$, $R^{602}$, $R^{603}$ and $R^{604}$ are independently selected from the group consisting of hydrogen and alkyl.

In another embodiment, $R^8$ is $C_1$ to $C_4$ alkyl substituted with $-R^{801}$, wherein $R^{801}$ is $C_1$ to $C_4$ alkyl optionally substituted with 1, 2, or 3 fluoro substitutents; $R^2$ is selected from the group consisting of phenyl and pyridinyl, wherein the phenyl and pyridinyl may be optionally substituted with one or more substituents selected from the group consisting of hydroxy, chloro, fluoro, methyl, methoxy, ethoxy, hydroxymethyl, $-C(O)CH_3$, $-C(O)CH(CH_3)_2$, $-N(CH_3)_2$, and $-S(O)_2CH_2(CH_3)$, and $R^{6A}$ and $R^{6B}$ together with the nitrogen to which they are attached form a heterocyclyl selected from the group consisting of piperadinyl, piperazinyl, and morpholinyl wherein the piperadinyl, piperazinyl, and morpholinyl may be optionally substituted with one or more substituents selected from the group consisting of chloro, hydroxy, ethyl, hydroxymethyl, hydroxyethyl, hydroxypropyl, $-CH_2C(CH_3)_2NH_2$, $-CH(CH_3)CH(CH_3)NH_2$, $-CH_2CH(CH_3)OH$, $-CH_2C(O)OC(CH_3)_3$, $-CH_2C(O)OH$, and $-C(O)NH_2$.

In another embodiment, $R^8$ is ethyl substituted with $-R^{801}$, wherein $R^{801}$ is selected from the group consisting of hydrogen, methyl, ethyl, and propyl wherein said methyl, ethyl and propyl may be optionally substituted with 1, 2 or 3 fluoro substituents; $R^2$ is selected from the group consisting of phenyl and pyridinyl, wherein the phenyl and pyridinyl may be optionally substituted with one or more substituents selected from the group consisting of hydroxy, chloro, fluoro, methyl, methoxy, ethoxy, hydroxymethyl, $-C(O)CH_3$, $-C(O)CH(CH_3)_2$, $-N(CH_3)_2$, and $-S(O)_2CH_2(CH_3)$, and $R^{6A}$ and $R^{6B}$ together with the nitrogen to which they are attached form a heterocyclyl selected from the group consisting of piperadinyl, piperazinyl, and morpholinyl wherein the piperadinyl, piperazinyl, and morpholinyl may be optionally substituted with one or more substituents selected from the group consisting of chloro, hydroxy, ethyl, hydroxymethyl, hydroxyethyl, hydroxypropyl, $-CH_2C(CH_3)_2NH_2$, $-CH(CH_3)CH(CH_3)NH_2$, $-CH_2CH(CH_3)OH$, $-CH_2C(O)OC(CH_3)_3$, $-CH_2C(O)OH$, and $-C(O)NH_2$.

In another embodiment, $R^2$ is pyridinyl substituted with methoxy, and $R^{6A}$ and $R^{6B}$ together with the nitrogen to which they are attached form a piperazinyl, wherein the piperazinyl may be optionally substituted with one or more substituents selected from the group consisting of chloro, hydroxy, ethyl, hydroxymethyl, hydroxyethyl, hydroxypropyl, $-CH_2C(CH_3)_2NH_2$, $-CH(CH_3)CH(CH_3)NH_2$, $-CH_2CH(CH_3)OH$, $-CH_2C(O)OC(CH_3)_3$, $-CH_2C(O)OH$, and $-C(O)NH_2$; and $R^8$ is propoxyethyl.

Embodiments of Formula I-12

In one embodiment, the invention comprises compounds having the structure of Formula I-12 of Table A:

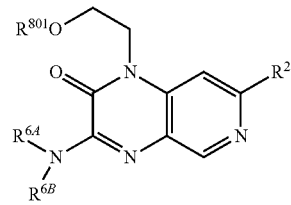

wherein:

$R^2$ is pyridinyl, optionally substituted with one or more substituents independently selected from the group consisting of halogen, cyano, nitro, oxo, alkyl, alkenyl, alkynyl, cycloalkyl, $-OR^{201}$, $-C(O)R^{201}$, $-OC(O)R^{201}$, $-C(O)OR^{201}$, $-NR^{201}R^{202}$, $-N(R^{202})C(O)R^{202}$, $-C(O)NR^{201}R^{202}$, $-C(O)NR^{201}C(O)R^{202}$ and $-S(O)_2R$; wherein said alkyl, alkenyl, and alkynyl and cycloalkyl substituents may be optionally substituted with one or more substituents independently selected from the group consisting of halogen, oxo, $-OR^{203}$, and $-C(O)OR^{203}$;

$R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy, alkoxy, carboxy and $-C(O)NH_2$;

$R^{6A}$ and $R^{6B}$ together with the nitrogen to which they are attached form a 5 to 7 membered partially or fully saturated ring heterocyclyl, wherein the heterocyclyl may be optionally substituted with one or more substituents independently selected from the group consisting of hydrogen, halogen, oxo, alkyl, alkenyl, alkynyl, cyano, $-OR^{601}$, $-C(O)R^{601}$, $-OC(O)R^{601}$, $-C(O)OR^{601}$, $-NR^{601}R^{602}$, $-N(R^{601})C(O)R^{602}$, $-C(O)NR^{601}R^{602}$, $-C(O)NR^{601}C(O)R^{602}$, cycloalkyl, aryl, and heterocyclyl, wherein (a) said alkyl, alkoxy, alkylamino, alkylcarbonyl, alkenyl, alkynyl and cycloalkyl substituents may be optionally substituted with one or more substituents independently selected from the group consisting of halogen, cyano, oxo, $-OR^{603}$, $-C(O)R^{603}$, $-C(O)OR^{603}$, $-OC(O)R^{603}$, $-NR^{603}R^{604}$, $-N(R^{603})C(O)R^{604}$, $-C(O)NR^{603}R^{604}$, $-C(O)NR^{603}C(O)R^{604}$, $-SR^{603}$, $-S(O)R^{603}$, $-S(O)_2R^{603}$, $-N(R^{603})S(O)_2R^{604}$, and $-S(O)_2NR^{603}R^{604}$, $C(O)NR^{603}C(O)R^{604}$, $-SR^{603}$, $-S(O)R^{603}$, $-S(O)_2R^{603}$, $-N(R^{603})S(O)_2R^{604}$, and $-S(O)_2NR^{603}R^{604}$, and (b) said $R^6$ aryl and heterocyclyl substituents may be optionally substituted with one or more substituents independently selected from the group consisting of halogen, alkyl, alkenyl, alkynyl, cyano, oxo, $-OR^{601}$, $-C(O)R^{601}$, $-C(O)OR^{601}$, $-OC(O)R^{601}$, $-NR^{601}R^{602}$, $-N(R^{601})C(O)R^{602}$, $-C(O)NR^{601}R^{602}$, $-C(O)NR^{601}C(O)R^{602}$, $-SR^{601}$, $-S(O)R^{602}$, $-S(O)_2R^{601}$, $-N(R^{601})S(O)_2R^{602}$, and $-S(O)_2NR^{601}R^{602}$;

$R^{601}$, $R^{602}$, $R^{603}$ and $R^{604}$ are independently selected from the group consisting of hydrogen, alkyl, alkenyl, and alkynyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy, and (b) said $R^{601}$ and $R^{602}$ alkenyl and alkynyl substituents may be optionally substituted with one or more substituents independently selected from the group consisting of halogen, cyano, hydroxy, carboxy, oxo, alkoxy, haloalkoxy, hydroxyalkoxy, and carboxyalkoxy; and $R^{801}$ is selected from the group consisting of hydrogen, and methyl, ethyl and propyl, wherein said methyl, ethyl and propyl may be optionally substituted with 1, 2, or 3 fluoro substituents.

In another embodiment of Formula I-12, $R^2$ is pyridinyl optionally substituted with one or more substituents independently selected from the group consisting of hydroxy, halogen, alkyl, —$OR^{201}$, —$C(O)R^{201}$, $NR^{201}R^{202}$, and —$S(O)_2 R^{201}$; wherein said alkyl may be optionally substituted with one or more —$OR^{203}$, and $R^{201}$, $R^{202}$ and $R^{203}$ are independently selected from the group consisting of hydrogen and alkyl.

In another embodiment of Formula I-12, $R^2$ is pyridinyl optionally substituted with one or more substituents independently selected from the group consisting of hydroxy, chloro, fluoro, methyl, ethyl, methoxy, ethoxy, hydroxymethyl, hydroxyethyl, —$C(O)C(CH_3)_2$, —$C(O)CH_3$, —$N(CH_3)_2$, and —$S(O)_2CH_2(CH_3)$.

In another embodiment of Formula I-12, the $R^2$ pyridinyl is selected from the group consisting of

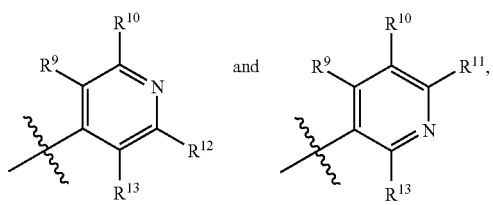

wherein $R^9$, $R^{10}$, $R^{11}$, and $R^{13}$ are independently selected from the group consisting of hydrogen, halogen, hydroxy, alkyl, hydroxyalkyl, aminoalkyl, alkoxy, alkoxyalkyl, amino, alkylamino, aminosulfonyl, and alkylsulfonyl.

In another embodiment of Formula I-12, the $R^2$ pyridinyl has the structure

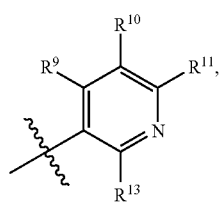

wherein $R^9$, $R^{10}$, $R^{11}$, and $R^{13}$ are independently selected from the group consisting of hydrogen, halogen, hydroxy, alkyl, hydroxyalkyl, aminoalkyl, alkoxy, alkoxyalkyl, amino, alkylamino, aminosulfonyl, and alkylsulfonyl.

In another embodiment of Formula I-12, the $R^2$ pyridinyl has the structure

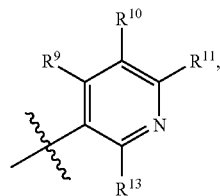

wherein $R^9$, $R^{10}$, $R^{11}$, and $R^{13}$ are independently selected from the group consisting of hydrogen, chloro, fluoro, hydroxy, methyl, ethyl, methoxy, ethoxy, hydroxymethyl, hydroxyethyl, —$C(O)CH_3$, —$C(O)CH(CH_3)_2$, —$N(CH_3)_2$, and —$S(O)_2CH_2(CH_3)$.

In another embodiment of Formula I-12, the $R^2$ pyridinyl has the structure

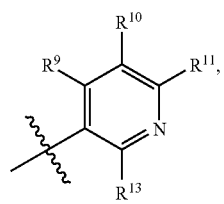

wherein at least one of $R^9$, $R^{10}$, $R^{11}$, and $R^{13}$ are independently selected from the group consisting of chloro, fluoro, hydroxy, methyl, methoxy, ethoxy, hydroxymethyl, —$C(O) CH_3$, —$C(O)CH(CH_3)_2$, —$N(CH_3)_2$, and —$S(O)_2CH_2 (CH_3)$.

In another embodiment of Formula I-12, the $R^2$ pyridinyl has the structure

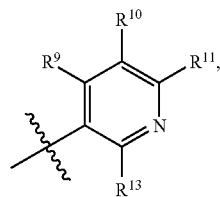

wherein $R^9$, $R^{10}$ and $R^{13}$ are each hydrogen, and $R^{11}$ is selected from the group consisting of hydrogen, chloro, fluoro, hydroxy, methyl, ethyl, methoxy, ethoxy, hydroxymethyl, hydroxyethyl, —$C(O)CH_3$, —$C(O)CH(CH_3)_2$, —$N(CH_3)_2$, and —$S(O)_2CH_2(CH_3)$.

In another embodiment of Formula I-12, the $R^2$ pyridinyl has the structure

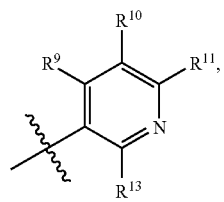

wherein $R^9$, $R^{10}$ and $R^{13}$ are each hydrogen, and $R^{11}$ is selected from the group consisting of hydrogen, methyl, methoxy, and —$N(CH_3)_2$.

In another embodiment of Formula I-12, the $R^2$ pyridinyl has the structure

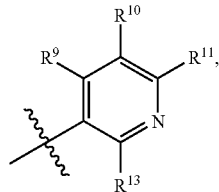

wherein $R^9$, $R^{10}$ and $R^{13}$ are each hydrogen, and $R^{11}$ is methoxy.

In another embodiment of Formula I-12, $R^2$ pyridinyl has the structure

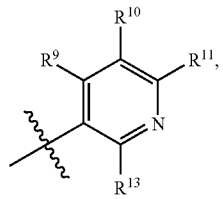

wherein $R^9$, $R^{10}$ and $R^{13}$ are each hydrogen, and $R^{11}$ is selected from the group consisting of hydrogen, chloro, fluoro, hydroxy, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$); $R^{6A}$ and $R^{6B}$ together with the nitrogen to which they are attached form a 5 to 7 membered partially or fully saturated ring heterocyclyl, wherein the heterocyclyl may be optionally substituted with one or more substituents independently selected from the group consisting of hydrogen, halogen, cyano, oxo, alkyl, —OR$^{601}$, —C(O)R$^{601}$, —C(O)OR$^{601}$, —NR$^{601}$R$^{602}$, —N(R$^{601}$)C(O)R$^{602}$, and —C(O)NR$^{601}$R$^{602}$, wherein (a) said alkyl substituent may be optionally substituted with one or more substituents independently selected from the group consisting of halogen, —OR$^{603}$, —C(O)R$^{603}$, —C(O)OR$^{603}$, and —NR$^{603}$R$^{604}$; and R$^{601}$, R$^{602}$, R$^{603}$ and R$^{604}$ are independently selected from the group consisting of hydrogen and alkyl, wherein said R$^{601}$ and R$^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

In another embodiment of Formula I-12, the $R^2$ pyridinyl has the structure

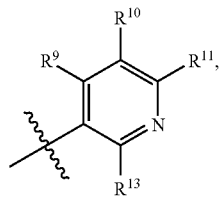

wherein $R^9$, $R^{10}$, $R^{11}$, and $R^{13}$ are independently selected from the group consisting of hydrogen, chloro, fluoro, hydroxy, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$); $R^{6A}$ and $R^{6B}$ together with the nitrogen to which they are attached form a 5 to 7 membered partially or fully saturated ring heterocyclyl, wherein the heterocyclyl may be optionally substituted with one or more substituents independently selected from the group consisting of hydrogen, halogen, alkyl, —OR$^{601}$, and —C(O)NR$^{601}$R$^{602}$, and R$^{601}$, R$^{602}$, R$^{603}$ and R$^{604}$ are independently selected from the group consisting of hydrogen and alkyl.

In another embodiment of Formula I-12, the $R^2$ pyridinyl has the structure

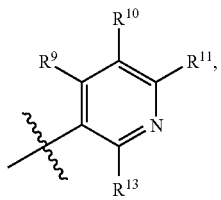

wherein $R^9$, $R^{10}$, $R^{11}$, and $R^{13}$ are independently selected from the group consisting of hydrogen, chloro, fluoro, hydroxy, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$); $R^{6A}$ and $R^{6B}$ together with the nitrogen to which they are attached form a heterocyclyl selected from the group consisting of pyrrolidinyl, piperadinyl, piperazinyl, morpholinyl and diazapinyl, wherein the pyrrolidinyl, piperadinyl, piperazinyl, morpholinyl and diazapinyl may be optionally substituted with one or more substituents selected from the group consisting of chloro, hydroxy, methyl, ethyl, propyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

In another embodiment of Formula I-12, the $R^2$ pyridinyl has the structure

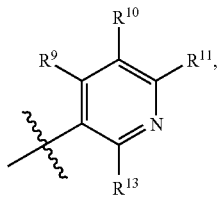

wherein $R^9$, $R^{10}$, $R^{11}$, and $R^{13}$ are independently selected from the group consisting of hydrogen, chloro, fluoro, hydroxy, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$); $R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of hydrogen, halogen, cyano, oxo, alkyl, —OR$^{601}$, —C(O)R$^{601}$, —C(O)OR$^{601}$, —NR$^{601}$R$^{602}$, —N(R$^{601}$)C(O)R$^{602}$, and —C(O)NR$^{601}$R$^{602}$, wherein (a) said alkyl substituent may be optionally substituted with one or more substituents independently selected from the group consisting of halogen, —OR$^{603}$, —C(O)R$^{603}$, —C(O)OR$^{603}$, and —NR$^{603}$R$^{604}$;

and $R^{601}$, $R^{602}$, $R^{603}$ and $R^{604}$ are independently selected from the group consisting of hydrogen and alkyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

In another embodiment of Formula I-12, the $R^2$ pyridinyl may be optionally substituted with one or more substituents independently selected from the group consisting of hydroxy, halogen, alkyl, —$OR^{201}$, —$C(O)R^{201}$, $NR^{201}R^{202}$, and —$S(O)_2R^{201}$; wherein said alkyl may be optionally substituted with one or more —$OR^{203}$, and $R^{201}$, $R^{202}$ and $R^{203}$ are independently selected from the group consisting of hydrogen and alkyl;

$R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of halogen, alkyl, —$OR^{601}$, and —$C(O)NR^{601}R^{602}$, wherein (a) said alkyl substituent may be optionally substituted with one or more substituents independently selected from the group consisting of —$OR^{603}$, —$C(O)OR^{603}$, and —$NR^{603}R^{604}$; and $R^{601}$, $R^{602}$, $R^{603}$ and $R^{604}$ are independently selected from the group consisting of hydrogen and alkyl.

In another embodiment of Formula I-12, the $R^2$ pyridinyl may be optionally substituted with one or more substituents independently selected from the group consisting of hydroxy, chloro, fluoro, methyl, ethyl, methoxy, ethoxy, hydroxymethyl, hydroxyethyl, —$C(O)CH_3$, —$C(O)CH(CH_3)_2$, —$N(CH_3)_2$, and —$S(O)_2CH_2(CH_3)$; $R^{6A}$ and $R^{6B}$ together with the nitrogen to which they are attached form a heterocyclyl selected from the group consisting of pyrrolidinyl, piperadinyl, piperazinyl, morpholinyl, and diazapinyl, wherein the pyrrolidinyl, piperadinyl, piperazinyl, morpholinyl, and diazapinyl may be optionally substituted with one or more substituents independently selected from the group consisting of chloro, hydroxy, methyl, ethyl, propyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$.

In another embodiment of Formula I-12, the $R^2$ pyridinyl is selected from the group consisting of

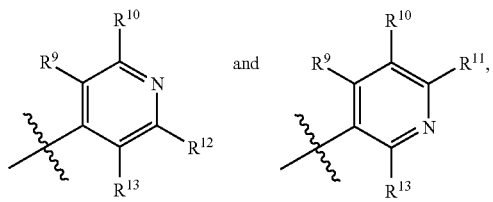

wherein $R^9$, $R^{10}$, $R^{11}$, and $R^{13}$ are independently selected from the group consisting of hydrogen, halogen, hydroxy, alkyl, hydroxyalkyl, aminoalkyl, alkoxy, alkoxyalkyl, amino, alkylamino, aminosulfonyl, and alkylsulfonyl; $R^{6A}$ and $R^{6B}$ together with the nitrogen to which they are attached form a heterocyclyl selected from the group consisting of piperadinyl, piperazinyl and morpholinyl wherein the piperadinyl, piperazinyl and morpholinyl may be optionally substituted with one or more substituents independently selected from the group consisting of chloro, hydroxy, methyl, ethyl, propyl, hydroxymethyl, hydroxyethyl, hydroxypropyl, —$CH_2C(CH_3)_2NH_2$, —$CH(CH_3)CH(CH_3)NH_2$, —$CH_2CH(CH_3)$OH, —$CH_2C(O)OC(CH_3)_3$, —$CH_2C(O)OH$, and —$C(O)NH_2$.

In another embodiment of Formula I-12, the $R^2$ pyridinyl has the structure

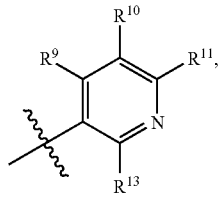

wherein $R^9$, $R^{10}$ and $R^{13}$ are each hydrogen; $R^{11}$ is selected from the group consisting of hydrogen, hydroxy, chloro, fluoro, methyl, ethyl, methoxy, ethoxy, hydroxymethyl, hydroxyethyl, —$C(O)CH_3$, —$C(O)CH(CH_3)_2$, —$N(CH_3)_2$, and —$S(O)_2CH_2(CH_3)$; $R^{6A}$ and $R^{6B}$ together with the nitrogen to which they are attached form a heterocyclyl selected from the group consisting of piperadinyl, piperazinyl and morpholinyl wherein the piperadinyl, piperazinyl and morpholinyl may be optionally substituted with one or more substituents independently selected from the group consisting of chloro, hydroxy, methyl, ethyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$; and $R^{801}$ is propyl.

In another embodiment of Formula I-12, the $R^2$ pyridinyl has the structure

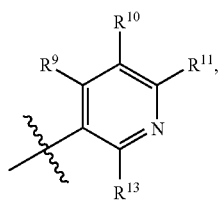

wherein one of $R^9$, $R^{10}$, $R^{11}$ and $R^{13}$ is methoxy and the remainder of $R^9$, $R^{10}$, $R^{11}$ and $R^{13}$ are hydrogen; $R^{6A}$ and $R^{6B}$ together with the nitrogen to which they are attached form a heterocyclyl selected from the group consisting of piperadinyl, piperazinyl and morpholinyl wherein the piperadinyl, piperazinyl and morpholinyl may be optionally substituted with one or more substituents independently selected from the group consisting of chloro, hydroxy, methyl, ethyl, hydroxymethyl, hydroxyethyl, hydroxypropyl, —$CH_2C(CH_3)_2NH_2$, —$CH(CH_3)CH(CH_3)NH_2$, —$CH_2CH(CH_3)$OH, —$CH_2C(O)OC(CH_3)_3$, —$CH_2C(O)OH$, and —$C(O)NH_2$; and $R^{801}$ is propyl.

In another embodiment of Formula I-12, the $R^2$ pyridinyl has the structure

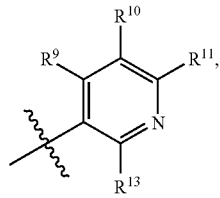

wherein one of $R^9$, $R^{10}$, $R^{11}$ and $R^{13}$ is methoxy and the remainder of $R^9$, $R^{10}$, $R^{11}$ and $R^{13}$ are hydrogen; $R^{6A}$ and $R^{6B}$ together with the nitrogen to which they are attached form a piperazinyl wherein the piperazinyl may be optionally substituted with one or more substituents independently selected from the group consisting of chloro, hydroxy, methyl, ethyl, propyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, —$CH_2C(O)OH$, and —$C(O)NH_2$.

In another embodiment of Formula I-12, the $R^2$ pyridinyl has the structure

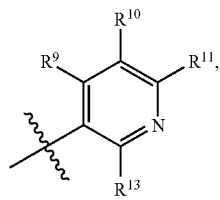

wherein one of $R^9$, $R^{10}$, $R^{11}$ and $R^{13}$ is methoxy and the remainder of $R^9$, $R^{10}$, $R^{11}$ and $R^{13}$ are hydrogen; $R^{6A}$ and $R^{6B}$ together with the nitrogen to which they are attached form a piperazinyl wherein the piperazinyl may be optionally substituted with one or more substituents independently selected from the group consisting of methyl, ethyl, propyl, hydroxymethyl, hydroxyethyl, hydroxypropyl, —$CH_2C(CH_3)_2NH_2$, —$CH(CH_3)CH(CH_3)NH_2$, —$CH_2CH(CH_3)OH$, —$CH_2C(O)OC(CH_3)_3$, and —$CH_2C(O)OH$.

C. Isomers

When an asymmetric center is present in a compound of Formulae (I) through (I-32) the compound can exist in the form of enantiomers or diastereomers. In one embodiment, the present invention comprises enantiomeric forms and mixtures, including racemic mixtures of the compounds of Formulae (I) through (I-32). In another embodiment, the present invention comprises diastereomeric forms (individual diastereomers and mixtures thereof) of compounds of Formulae (I) through (I-32). When a compound of Formulae (I) through (I-32) contains an alkenyl group or moiety, geometric isomers may arise.

D. Tautomeric Forms

The present invention comprises the tautomeric forms of compounds of Formulae (I) through (I-32). For instance, a tautomeric form of the following compound:

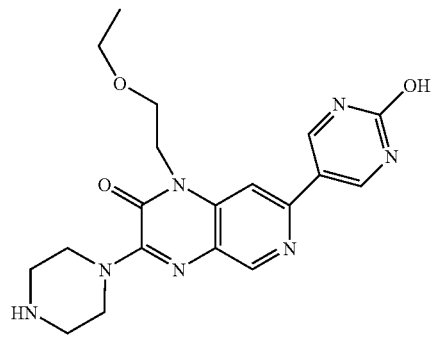

may be represented by:

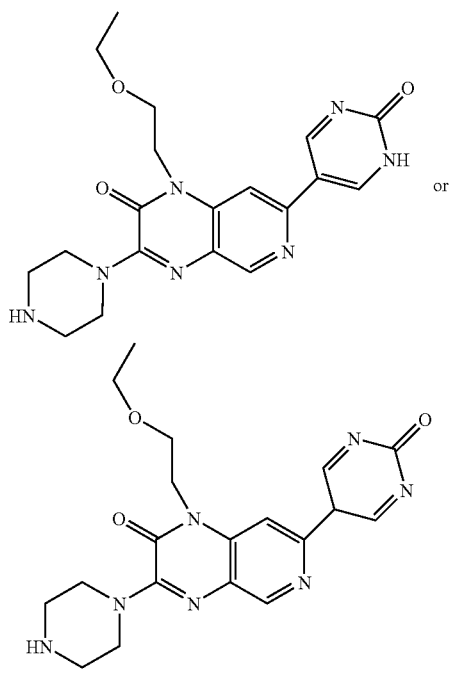

The various ratios of the tautomers in solid and liquid form is dependent on the various substituents on the molecule as well as the particular crystallization technique used to isolate a compound.

E. Salts

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formulae (I)-(I-32) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclyl, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

In another embodiment, examples of suitable addition salts formed include the acetate, aspartate, benzoate, besylate, bicarbonate/carbonate, bisulphate/sulphate, borate, camsyate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, nitrate, orotate, oxalate, palmitate, pamoate, phosphate/hydrogen phosphate/dihidrogen phosphate, saccharate, stearate, succinate, tartrate, tosylate and trifluoroacetate salts.

In another embodiment, representative salts include benzenesulfonate, hydrobromide and hydrochloride.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$ to $C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, salts of the compounds of this invention include hydrochloric acid (HCl) salts, trifluoroacetate ($CF_3COOH$ or "TFA") salts, mesylate salts, and tosylate salts.

Pharmaceutically acceptable salts of compounds of Formulae (I) to (I-32) may be prepared by one or more of three methods:

(i) by reacting the compound of any one of Formulae (I)-(I-32) with the desired acid or base;

(ii) by removing an acid- or base-labile protecting group from a suitable precursor of the compound of any one of Formulae (I)-(I-32) or by ring-opening a suitable cyclic precursor, for example, a lactone or lactam, using the desired acid or base; and (iii) by converting one salt of the a compound of Formulae (I) through (I-32) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionised.

F. Methods of Treatment

The present invention further comprises methods for treating a condition in a subject having or susceptible to having such a condition, by administering to the subject a therapeutically-effective amount of one or more compounds of Formulae (I) through (I-32) as provided above. In one embodiment, the treatment is preventative treatment. In another embodiment, the treatment is palliative treatment. In another embodiment, the treatment is restorative treatment.

In another embodiment, the condition is a PDE5-mediated condition. In another embodiment, the condition is a cGMP-mediated condition. A condition in which, for instance, insufficient cGMP is a major component, and whose production or action is modulated in response to the PDE5 enzyme, would therefore be considered a disorder mediated by cGMP.

The conditions that can be treated in accordance with the present invention include, but are not limited to, cardiovascular conditions, metabolic conditions, central nervous system conditions, pulmonary conditions, sexual dysfunction, pain and renal dysfunction.

In another embodiment, the condition is a cardiovascular condition selected from the group consisting of hypertension (including essential hypertension, pulmonary hypertension, pulmonary arterial hypertension, secondary hypertension, isolated systolic hypertension, hypertension associated with diabetes, hypertension associated with atherosclerosis, and renovascular hypertension); complications associated with hypertension (including vascular organ damage, congestive heart failure, angina, stroke, glaucoma and impaired renal function); valvular insufficiency; stable, unstable and variant (Prinzmetal) angina; peripheral vascular disease; myocardial infarct; stroke (including stroke recovery); thromboembolic disease; restenosis; arteriosclerosis; atherosclerosis; angiostenosis after bypass; angioplasty (including percutaneous transluminal angioplasty and percutaneous transluminal coronary angioplasty); hyperlipidemia; hypoxic vasoconstriction; vasculitis (including Kawasaki's syndrome); heart failure (including congestive heart failure, decompensated heart failure, systolic heart failure, diastolic heart failure, left ventricular heart failure, right ventricular heart failure, and left ventricular hypertrophy); Raynaud's phenomenon; preeclampsia; pregnancy-induced high blood pressure; cardiomyopathy; and arterial occlusive disorders.

In another embodiment, the condition is hypertension.

In another embodiment, the condition is pulmonary hypertension.

In another embodiment, the condition is pulmonary arterial hypertension.

In another embodiment, the condition is heart failure.

In another embodiment, the condition is diastolic heart failure.

In another embodiment, the condition is systolic heart failure.

In another embodiment, the condition is angina.

In another embodiment, the condition is thrombosis.

In another embodiment, the condition is stroke.

In another embodiment, the condition is a condition associated with endothelial dysfunction (including conditions selected from the group consisting of atherosclerotic lesions, myocardial ischaemia, peripheral ischaemia, valvular insufficiency, pulmonary arterial hypertension, angina, clots, vascular complications after vascular bypass, vascular dilation, vascular repermeabilisation, and heart transplantation).

In another embodiment, the condition is a metabolic condition selected from the group consisting of Syndrome X (also known as metabolic syndrome); diabetes (including type I and type II diabetes); insulin resistance; syndromes of insulin resistance (including insulin receptor disorders, Rabson-Mendenhall syndrome, leprechaunism, Kobberling-Dunnigan syndrome, Seip syndrome, Lawrence syndrome, Cushing syndrome, acromegaly, pheochomocytoma, glucagonoma, primary aldosteronism, somatostatinoma, Lipoatrophic diabetes, β-cell toxin induced diabetes, Grave's disease, Hashimoto's thyroiditis and idiopathic Addison's disease); impaired glucose tolerance; diabetic complications (including diabetic gangrene, diabetic arthropathy, diabetic nephropathy, diabetic glomerulosclerosis, diabetic deramatopathy, diabetic neuropathy, peripheral diabetic neuropathy, diabetic cataract, and diabetic retinopathy); hyperglycemia; and obesity.

In another embodiment, the condition is insulin resistance.

In another embodiment, the condition is nephropathy.

In another embodiment, the condition is a central nervous system condition selected from the group consisting of dementia, including vascular dementia and AIDS-induced dementia; spinal cord trauma, head trauma; traumatic brain injury; hypoglycemic neuronal damage; craniocerebral trauma; cerebral infarct; cerebrovascular accident; concentration disorders; chronic degenerative disorders, including Alzheimer's disease; Parkinson's disease, including idiopathic and drug-induced Parkinson' disease; amyotrophic lateral sclerosis; amyolateral sclerosis; Huntington's disease, including Huntington's Chorea; muscular spasms and disorders associated with muscular spasticity including tremors, epilepsy, convulsions; restless legs syndrome; multiple sclerosis; Creutzfeld-Jacob disease; sleep disorders, including narcolepsy; cognitive disorders, including cognitive disorders relating to schizophrenia; psychosis, schizophrenia; substance withdrawal, including withdrawal from substances such as opiates, nicotine, tobacco products, alcohol, benzodiazepines, cocaine, sedatives, hypnotics; anxiety, including generalized anxiety disorder, social anxiety disorder, panic disorder, post-traumatic stress disorder and obsessive compulsive disorder; attention deficit/hyperactivity disorder, conduct disorder; mood disorders, including depression, mania, bipolar disorders; trigeminal neuralgia, hearing loss, tinnitus, emesis, brain edema, tardive dyskinesia; and migraine, including migraine headache.

In another embodiment, the condition is Alzheimer's disease.

In another embodiment, the condition is Parkinson's disease.

In another embodiment, the condition is amyolateral sclerosis.

In another embodiment, the condition is cerebral infact.

In another embodiment, the condition is a concentration disorder.

In another embodiment, the condition is stroke.

In another embodiment, the present invention further comprises methods for promoting functional recovery following brain injury. In another embodiment the present invention further comprises methods for promoting functional recovery following craniocerebral trauma. In another embodiment, the present invention further comprises methods for promoting functional recovery following stroke. (Ren, J. N., Finklestein, S. P., Tate, B., Stephenson, D. T., Seeger, T. F., and Menniti, F. S. The PDE5 inhibitor sildenafil improves functional recovery after middle cerebral artery occlusion in rats: mechanism of action? 582.15 Society for Neuroscience, 36th Annual Meeting 2006).

In another embodiment, the present invention further comprises methods for promoting neurorestoration, including neurorestoration following stroke, such as neurorestoration following coronary artery bypass grafting (CABG)-related stroke; neurorestoration following traumatic brain injury; neurorestoration following cerebral ischemia, including cerebral ischemia related to CABG; neurorestoration related to multi-infarct dementia; and neurorestoration related to post-CABG dementia.

In another embodiment, the condition is a concentration disorder.

In another embodiment, the condition is a pulmonary condition selected from the group consisting of asthma; acute respiratory distress; cystic fibrosis; chronic obstructive pulmonary disease; bronchitis; and chronic reversible pulmonary obstruction.

In another embodiment, the condition is pain. In another embodiment, the condition is acute pain. Examples of acute pain include acute pain associated with injury or surgery. In another embodiment, the condition is chronic pain. Examples of chronic pain include neuropathic pain (including postherpetic neuralgia and pain associated with peripheral, cancer or diabetic neuropathy), carpal tunnel syndrome, back pain (including pain associated with herniated or ruptured intervertabral discs or abnormalities of the lumber facet joints, sacroiliac joints, paraspinal muscles or the posterior longitudinal ligament), headache, cancer pain (including tumour related pain such as bone pain, headache, facial pain or visceral pain) or pain associated with cancer therapy (including postchemotherapy syndrome, chronic postsurgical pain syndrome, post radiation syndrome, pain associated with immunotherapy, or pain associated with hormonal therapy), arthritic pain (including osteoarthritis and rheumatoid arthritis pain), chronic post-surgical pain, post herpetic neuralgia, trigeminal neuralgia, HIV neuropathy, phantom limb pain, central post-stroke pain and pain associated with chronic alcoholism, hypothyroidism, uremia, multiple sclerosis, spinal cord injury, Parkinson's disease, epilepsy and vitamin deficiency. In another embodiment, the condition is nociceptive pain (including pain from central nervous system trauma, strains/sprains, burns, myocardial infarction and acute pancreatitis, post-operative pain (pain following any type of surgical procedure), posttraumatic pain, renal colic, cancer pain and back pain). In another embodiment, the condition is pain associated with inflammation (including arthritic pain (such as osteoarthritis and rheumatoid disease pain), ankylosing spondylitis, visceral pain (including inflammatory bowel disease, functional bowel disorder, gastro-esophageal reflux, dyspepsia, irritable bowel syndrome, functional abdominal pain syndrome, Crohn's disease, ileitis, ulcerative colitis, dysmenorrheal, cystitis, pancreatitis and pelvic pain). In another embodiment, the condition is pain resulting from musculo-skeletal disorders (including myalgia, fibromyalgia, spondylitis, seronegative (non-rheumatoid) arthropathies, non-articular rheumatism, dystrophinopathy, glycogenolysis, polymyositis and pyomyositis). In another embodiment, the condition is selected from the group consisting of heart and vascular pain (including pain caused by angina, myocardial infarction, mitral stenosis, pericarditis, Raynaud's phenomenon, scleredoma and skeletal muscle ischemia). In another embodiment, the condition is selected from the group consisting of head pain (including migraine such as migraine with aura and migraine without aura), cluster headache, tension-type headache mixed headache and headache associated with vascular disorders; orofacial pain, including dental pain, otic pain, burning mouth syndrome and temporomandibular myofascial pain).

In another embodiment, the condition is sexual dysfunction (including sexual dysfunction selected from the group consisting of impotence (organic or psychic); male erectile dysfunction; clitoral dysfunction; sexual dysfunction after spinal cord injury; female sexual arousal disorder; female sexual orgasmic dysfunction; female sexual pain disorder; and female hypoactive sexual desire disorder).

In another embodiment, the condition is male erectile dysfunction.

In another embodiment, the condition is renal dysfunction (including renal dysfunction selected from the group consisting of acute renal failure, chronic renal failure; nephropathy (such as diabetic nephropathy); tubulointerstitial disorders; glomerulopathy; and nephritis. In another embodiment, the condition is a cancer condition selected from the group consisting of cancerous cachexia; tumor metastasis and neoplasia.

In another embodiment, the condition is osteoporosis.

In another embodiment, the condition is a gastrointestinal condition selected from the group consisting of nutcracker oesophagus; anal fissure; disorders of gut motility; irritable bowel syndrome, Crohn's disease and haemorrhoids. In another embodiment, the condition is a urologic condition selected from the group consisting of overactive bladder; bladder outlet obstruction; incontinence and benign prostatic hyperplasia.

In another embodiment, the condition is a skin condition, selected from psoriasis; urticaria and skin necrosis.

In another embodiment, the condition is an ophthalmic condition selected from retinal disease; macular degeneration and glaucoma.

In another embodiment, the condition is nitrate intolerance.

In another embodiment, the condition is baldness.

In another embodiment, the condition is a gynecologic condition selected from the group consisting of dysmenorrhoea (primary and secondary); infertility and premature labor. In another embodiment, the condition is secondary dysmenorrhoea.

In another embodiment, the present invention further comprises methods for inducing weight loss or maintenance of weight loss in a subject by administering to the subject a therapeutically-effective amount of a compound of Formulae (I) through (I-32).

G. Subjects

The methods and compounds of the present invention are suitable for use with, for example, mammalian subjects such as humans, other primates (e.g., monkeys, chimpanzees), companion animals (e.g., dogs, cats, horses), farm animals (e.g., goats, sheep, pigs, cattle), laboratory animals (e.g., mice, rats), and wild and zoo animals (e.g., wolves, bears, deer). In one embodiment, the subject is a mammalian subject. In another embodiment, the subject is a human.

H. Hypothesized Mechanism

Without being held to a particular theory, it is hypothesized that compounds of Formulae (I) through (I-32) are inhibitors of the PDE5 enzyme. It is further hypothesized that the compounds of Formulae (I) through (I-32) inhibit the action of the PDE5 enzyme leading to an increase in intracellular cGMP levels. This increase in intracellular cGMP levels reduces intracellular calcium signaling, which in turn results in vascular smooth muscle relaxation and a reduction in blood pressure.

I. Administration and Dosing

Typically, a compound described in this specification is administered in an amount effective to inhibit PDE-5. The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of Formulae (I) through (I-32) (administered in single or divided doses) is typically from about 0.01 to about 100 mg/kg. In another embodiment, total daily dose of the compound of Formulae (I) through (IX) is from about 0.1 to about 50 mg/kg, and in another embodiment, from about 0.5 to about 30 mg/kg (i.e., mg compound of Formulae (I) through (I-32) per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient to be treated. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

J. Use in the Preparation of a Medicament

In one embodiment, the present invention comprises the compounds of Formulae (I) through (I-32) for use as a medicament (such as a unit dosage tablet or unit dosage capsule). It is understood that the medicament may be in combination with one or more pharmaceutically-acceptable carriers and/or other active ingredients.

In another embodiment, the invention comprises the use of one or more compounds of Formulae (I) through (I-32) for use as a medicament (such as a unit dosage tablet or unit dosage capsule) for use in treating one or more of the conditions previously identified in the above sections discussing methods of treatment.

In another embodiment, the invention comprises the use of one or more compounds of Formulae (I) through (I-32) in the preparation of a medicament for the treatment of hypertension.

K. Pharmaceutical Compositions

For the treatment of the conditions referred to above, the compounds of Formulae (I) through (I-32) can be administered as compound per se. Alternatively, pharmaceutically acceptable salts of the compounds of Formulae (I) through (I-32) can also be administered. In another embodiment, the compounds of Formulae (I) through (I-32) can be administered as a mixture of compound per se and one or more pharmaceutically acceptable salts of the compound per se.

In another embodiment, the present invention comprises pharmaceutical compositions. Such pharmaceutical compositions comprise compounds of Formulae (I) through (I-32) presented with at least one pharmaceutically-acceptable carrier. The carrier can be a solid, a liquid, or both, and may be formulated with the compound as a unit-dose composition, for example, a tablet, which can contain from 0.05% to 95% by weight of the compounds of Formulae (I) through (I-32). Compounds of Formulae (I) through (I-32) may be coupled with suitable polymers as targetable drug carriers. Other pharmacologically active substances can also be present.

The compounds of Formulae (I) through (I-32) may be administered by any suitable route, preferably in the form of a pharmaceutical composition adapted to such a route, and in a dose effective for the treatment intended. The compounds and compositions of Formulae (I) through (I-32), for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formulae (I) through (I-32) are ordinarily combined with one or more adjuvants. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Formulations suitable for topical administration to the eye include, for example, eye drops wherein the compound of this invention is dissolved or suspended in suitable carrier. For intranasal administration or administration by inhalation, the compounds of Formulae (I) through (I-32) are conveniently delivered in the form of a solution or suspension from a pump spray container that is squeezed or pumped by the patient or as an aerosol spray presentation from a pressurized container or a nebulizer, with the use of a suitable propellant.

In another embodiment, the present invention comprises a rectal dose form. Such rectal dose form may be in the form of, for example, a suppository.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., Handbook of Pharmaceutical Excipients ($3^{rd}$ Ed.), American Pharmaceutical Association, Washington, 1999.

L. Combinations and Combination Therapy

One or more compounds of the present invention can be used, alone or in combination with other therapeutic agents, in the treatment of various conditions or disease states discussed above. The compound(s) of the present invention and other therapeutic agent(s) may be may be administered simultaneously (either in the same dosage form or in separate dosage forms) or sequentially. Accordingly, in one embodiment, the present invention comprises methods for treating a condition in a subject having or susceptible to having such a condition by administering to the subject a therapeutically-effective amount of one or more compounds of Formulae (I) through (I-32) and one or more additional therapeutic agents. In another embodiment, the present invention comprises a pharmaceutical composition comprising one or more compounds of Formulae (I) through (I-32), one or more additional therapeutic agents, and a pharmaceutically acceptable carrier.

For instance, in one embodiment, one or more compounds of Formulae (I) through (I-32) may be administered with aspirin.

In another embodiment, one or more compounds of Formulae (I) through (I-32) may be co-administered with one or more diruretic. Examples of suitable diuretics include hydroclorothiazide (such as MICROZIDE™ or ORETIC™), hydroflumethiazide (such as SALURON™), bemetanide (such as BUMEX™), torsemide (such as DEMADEX™), metolazone (such as ZAROXOLYN™), chlorothiazide (such as DIURIL™, ESIDRIX™ or HYDRODIURIL™), triamterene (such as DYRENIUM™), ethacrynic acid (such as EDECRIN™), chlorthalidone (such as HYGROTON™), furosemide (such as LASIX™), indapamide (such as LOZOL™), or amiloride (such as MIDAMOR™ or MODURETIC™).

In one embodiment, one or more compounds of Formulae (I) through (I-32) may be co-administered with one or more angiotensin converting enzyme inhibitors. Examples of suitable angiotensin converting enzyme inhibitors include quinapril (such as ACCUPRIL™), perindopril (such as ACEON™), captopril (such as CAPOTEN™), enalapril (such as VASOTEC™), ENALAPRILAT™, ramipril (such as ALTACE™), cilazapril, delapril, fosenopril (such as MONOPRIL™), zofenopril, indolapril, benazepril (such as LOTENSIN™), lisinopril (such as PRINIVIL™ and ZESTRIL™), spirapril, trandolapril (such as MAVIK™), perindep, pentopril, moexipril (such as UNIVASC™) fasidotril, S-allymercaptocaptopril, and pivopril.

In another embodiment, one or more compounds of Formulae (I) through (I-32) may be co-administered with one or more angiotensin II receptor blockers. Examples of suitable angiotensin II receptor blockers include candesartan (such as ATACAND™), eprosartan (such as TEVETEN™), irbesartan (such as AVEPRO™), losartan (such as COZAAR™), olmesartan, olmesartan medoxomil (such as BENICAR™), tasosartan, telmisartan (such as MICARDIS™), valsartan (such as DIOVAN™), zolasartan, FI-6828K, RNH-6270, UR-7198, Way-126227, KRH-594, TAK-536, BRA-657, and TA-606.

In another embodiment, one or more compounds of Formulae (I) through (I-32) may be co-administered with one or more calcium channel blockers. Examples of suitable calcium channel blockers include nifedipine (such as ADALAT™, ADALAT CC™ and PROCARDIA™), verapamil (such as CALANT™, COVERA-HS™, ISOPTIN SR™ and VERELAN™), diltiazem (such as CARDIZEM™ CARDIZEM CD™, CARDIZEM LA™, CARDIZEM SR™, DILACOR™, TIAMATE™ and TIAZAC™), isradipine (such as DYNACIRC™ and DYNACIRC CR™), amlodipine (such as NORVASC™), felodipine (such as PLENDIL™), nisoldipine (such as SULAR™), bepridil (such as VASCOR™), vatanidipine, clevidipine, lercanidipine, dilitiazem, and NNC-55-0396.

In another embodiment, one or more compounds of Formulae (I) through (I-32) may be co-administered with one or more beta blockers. Examples of suitable beta blockers include timolol (such as BLOCARDEN™), carteolol (such as CARTROL™), carvedilol (such as COREG™), nadolol (such as CORGARD™), propranolol (such as INNOPRAN XL™), betaxolol (such as KERLONE™), penbutolol (such as LEVATOL™), metoprolol (such as LOPRESSOR™ and TOPROL-XL™), atenolol (such as TENORMIN™), pindolol (such as VISKEN™), and bisoprolol.

In another embodiment, one or more compounds of Formulae (I) through (I-32) may be co-administered with one or more alpha blockers. Examples of suitable alpha blockers include prazosin, doxazosin (such as CARDURA™), phenoxybenzamine (such as DIBENZYLINE™), terazosin (such as HYTRIN™), CDRI-93/478 and CR-2991.

In another embodiment, one or more compounds of Formulae (I) through (I-32) may be co-administered with one or more alpha-beta blockers. An example of a suitable alpha-beta blocker is labetalol (such as NORMODYNE™ or TRANDATE™).

In another embodiment, one or more compounds of Formulae (I) through (I-32) may be co-administered with one or more aldosterone receptor antagonists. Examples of suitable aldosterone receptor antagonists include eplerenone (such as INSPRA™) or spironolactone (such as ALDACTONE™).

In another embodiment, one or more compounds of Formulae (I) through (I-32) may be co-administered with one or more renin inhibitors. Examples of suitable renin inhibitors include aliskiren (SPP 100), SPP-500/600 and YS-004-39.

In another embodiment, one or more compounds Formulae (I) through (I-32) may be co-administered with one or more central antiadrenergics. Examples of suitable central antiadrenergics includes methyldopa (such as ALDOMET™), clonidine (such as CATAPRES™ or CATAPRES-TTS™), guanfacine (such as TENEX™), and guanabenz (such as WYTENSIN™).

In another embodiment, one or more compounds of Formulae (I) through (I-32) may be co-administered with one or more glycosides/inotropic agents. An example of a suitable glycoside/inotropic agent is digoxin (such as LANOXIN™).

In another embodiment, one or more compounds of Formulae (I) through (I-32) may be co-administered with one or more human B-type natriuretic peptides (hBNP) such as nesiritide (such as NATRECOR™).

In another embodiment, one or more compounds of Formulae (I) through (I-32) may be co-administered with one or more organic nitrates or an NO donors. "Nitric oxide donor" refers to a compound that donates, releases and/or directly or indirectly transfers a nitrogen monoxide species, and/or stimulate the endogenous production of nitric oxide or endothelium-derived relaxing factor (EDRF) in vivo and/or elevate endogenous levels of nitric oxide or EDRF in vivo. It also includes compounds that are substrates for nitric oxide synthase. Examples of suitable nitric oxide donors include S-nitrosothiols, nitrites, nitrates, N-oxo-N-nitrosamines, SPM 3672, SPM 5185, SPM 5186 and analogues thereof, sodium nitroprusside, nitroglycerin, isosorbide dinitrate, isosorbide mononitrate, molsidomine, SIN-1 and substrates of the various isozymes of nitric oxide synthase.

In another embodiment, one or more compounds of Formulae (I) through (I-32) may be co-administered with one or more soluble guanylate cyclase activator ("sGCa"). An example of a suitable soluble guanylate cyclase activator is BAY-41-8543.

In another embodiment, one or more compounds of Formulae (I) through (I-32) may be co-administered with one or more bradykinin agonists.

In another embodiment, one or more compounds of Formulae (I) through (I-32) may be co-administered with one or more neutral endopeptidase inhibitors. Examples of suitable neutral endopeptidase inhibitors include omapatrilat, fasidotril, mixanpril, sampatrilat, Z13752A,

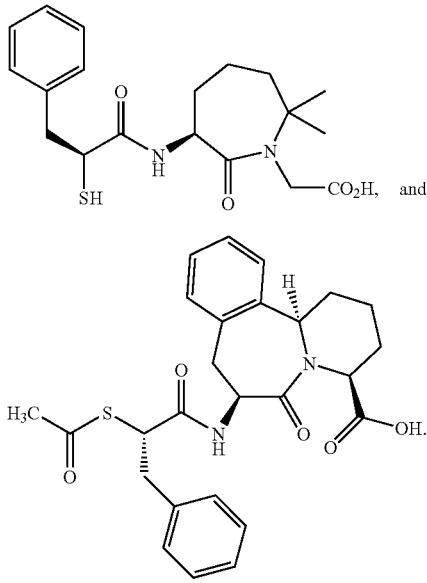

BMS-189921

MDL-100240

In another embodiment, one or more compounds of Formulae (I) through (I-32) may be co-administered with one or more endothelian antagonists. Examples of suitable endothelin antagonists include ambrisentan, darusentan, J-104132, SPP-301, TBC-3711, YM-62899, YM-91746 and BMS-193884.

In another embodiment, one or more compounds of Formulae (I) through (I-32) may be co-administered with one or more 3-hydroxy-3-methylglutaryl coenzyme A reductase inhibitors. Examples of suitable 3-hydroxy-3-methylglutaryl coenzyme A reductase inhibitors include fluvastatin (such as LESCOL™), atorvastatin (such as LIPITOR™), lovastatin (such as ALTOCOR™ or MEVACOR™), pravastatin (such as PRAVACHOL™), rosuvastatin (such as CRESTOR™), and simvastatin (such as ZOCOR™).

In another embodiment, one or more compounds of Formulae (I) through (I-32) may be co-administered with niacin or one or more nicotinic acid derivatives. Examples of suitable niacin or nicotinic acid derivatives include NIACOR™, NIASPAN™, NICOLAR™, and SLO-NIACIN™.

In another embodiment, one or more compounds of Formulae (I) through (I-32) may be co-administered with one or more fibric acid derivatives. Examples of suitable fibric acid derivatives include clofibrate (such as ATROMID-S™), gemfibrozil (such as LOPID™), and fenofibrate (such as TRICOR™).

In another embodiment, one or more compounds of Formulae (I) through (I-32) may be co-administered with one or more bile acid sequestants. Examples of suitable bile acid sequestants include colestipol (such as COLESTID™), cholestyramine (such as LOCHOLEST™, PREVALITE™, QUESTRAN™, and QUESTRAN LIGHT™), colesevelam (such as WELCHOL™).

In another embodiment, one or more compounds of Formulae (I) through (I-32) may be co-administered with one or more cholesterol absorption inhibitors. An example of a suitable cholesterol absorption inhibitor is ezetimibe (such as ZETIA™).

In another embodiment, one or more compounds of Formulae (I) through (I-32) may be co-administered with one or more cholesteryl ester transport protein inhibitors. An example of a suitable cholesteryl ester transport protein inhibitor is torcetrapib.

In another embodiment, one or more compounds of Formulae (I) through (I-32) may be co-administered with one or more apical sodium-dependent bile acid cotransporter inhibitors. Examples of suitable apical sodium-dependent bile acid cotransporter inhibitors include SD-5613, AZD7806 and 264W94.

In another embodiment, one or more compounds of Formulae (I) through (I-32) may be co-administered with one or more alpha glucosidase inhibitors. Examples of suitable alpha glucosidase inhibitors include miglitol (such as GLYSET™) and acarbose (such as PRECOSE™).

In another embodiment, one or more compounds of Formulae (I) through (I-32) may be co-administered with one or more biguanides. Examples of suitable biguanides include rosiglitazone (such as AVANDAMET™) and metformin (such as GLUCOPHAGE™ and GLUCOPHAGE XR™).

In another embodiment, one or more compounds of Formulae (I) through (I-32) may be co-administered with one or more insulins. Examples of suitable insulins include HUMALOG™, HUMALOG 50/50™, HUMALOG 75/25™, HUMULIN 50/50™, HUMALIN 75/25™, HUMALIN L™, HUMALIN N™, HUMALIN R™, HUMALIN R U-500™, HUMALIN U™, ILETIN II LENTE™, ILETIN II NPH™, ILETIN II REGULAR™, LANTUS™, NOVOLIN 70/30™, NOVILIN N™, NOVILIN R™, NOVOLOG™, VELOSULIN BR™, and EXUBERA™.

In another embodiment, one or more compounds of Formulae (I) through (I-32) may be co-administered with one or more meglitnides. Examples of suitable meglitnides include repaglinide (such as PRANDIN™) and nateglinide (such as STARLIX™).

In another embodiment, one or more compounds of Formulae (I) through (I-32) may be co-administered with one or more sulfonylureas. Examples of suitable sulfonylureas include glimepiride (such as AMARYL™), glyburide (such as DIABETA™, GLYNASE PRESTAB™ or MICRONASE™), and glipizide (such as GLUCOTROL™ and GLUCOTROL XL™).

In another embodiment, one or more compounds of Formulae (I) through (I-32) may be co-administered with one or more thiazolidinediones. Examples of suitable thiazolidinediones include pioglitazone (such as ACTOS™) and rosiglitazone (such as AVANDIA™).

In another embodiment, one or more compounds of Formulae (I) through (I-32) may be co-administered with one or more alpha-2-delta ligands. Examples of suitable alpha-2-delta ligands include gabapentin, pregabalin (such as LYRICA™), [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)-(3-aminomethyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid and (3S,5R)-3-amino-5-methyl-octanoic acid), (2S,4S)-4-(3-Chlorophenoxy)praline, and (2S,4S)-4-(3-Fluorobenzyl)praline.

M. Kits

The present invention further comprises kits that are suitable for use in performing the methods of treatment or prevention described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of Formulae (I) through (I-32) and an angiotensin converting enzyme inhibitor.

In another embodiment, the kit of the present invention comprises one or more compounds of Formulae (I) through (I-32) and an angiotensin II receptor antagonist.

In another embodiment, the kit of the present invention comprises one or more compounds of Formulae (I) through (I-32) and an aldosterone receptor antagonist.

In another embodiment, the kit of the present invention comprises one or more compounds of Formulae (I) through (I-32) and a NO donor.

N. Compound Preparations

Schemes

The starting materials used herein are commercially available or may prepared by routine methods known to those of ordinary skill in the art (such as those methods disclosed in standard reference books such as the COMPENDIUM OF ORGANIC SYNTHETIC METHODS, Vol. I-VI (published by Wiley-Interscience)).

The compounds of the present invention may be prepared using the methods illustrated in the general synthetic schemes and experimental procedures detailed below. The general synthetic schemes are presented for purposes of illustration and are not intended to be limiting.

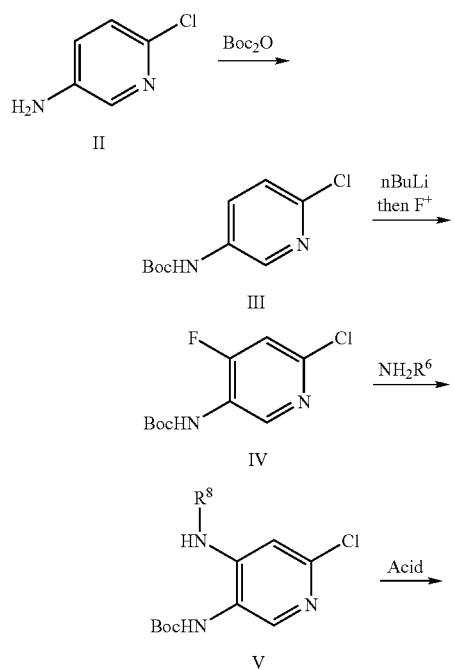

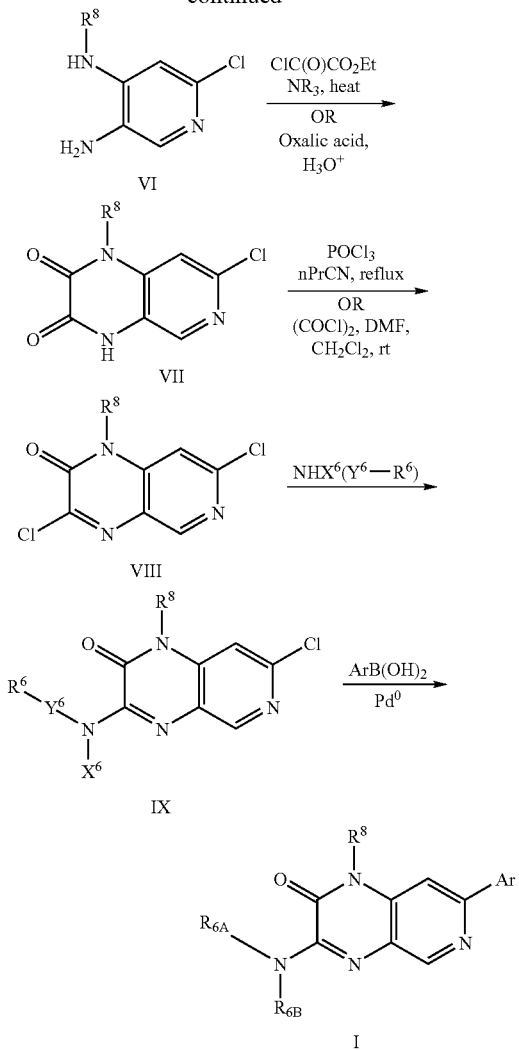

Scheme 1 outlines a general procedure for the preparation of 7-aryl pyrido[3,4-b]pyrazin of formula I.

The starting material was the commercially available 6-chloropyridin-3-amine II. 6-chloropyridin-3-amine II was protected, for example by converting to tert-butyl 6-chloropyridin-3-ylcarbamate III by treatment with reagents such as di-tert-butyl dicarbonate, (2E)-{[(tert-butoxycarbonyl)oxy]imino}(phenyl)acetonitrile and tert-butyl phenyl carbonate. This reaction was carried out in solvents such as dioxane, tetrahydrofuran, water, ethyl acetate or dichloromethane, in the presence or absence of inorganic bases such as potassium carbonate or sodium bicarbonate or organic bases such as triethylamine, 4-methylmorpholine, pyridine or N,N-diisopropylethylamine at temperatures ranging from room temperature to 110° C.

tert-butyl 6-chloropyridin-3-ylcarbamate III was converted to tert-butyl 6-chloro-4-fluoropyridin-3-ylcarbamate IV by metallation followed by quenching with an electrophilic fluorine source.

Lithation was achieved be treating tert-butyl 6-chloropyridin-3-ylcarbamate III with an organolithium such as n-butyl lithium or t-butyl lithium in the presence or absence of additives such as N,N,N',N'-tetramethylethylenediamine in solvents such as diethyl ether or tetrahydrofuran at temperatures ranging from −80° C. to 0° C. Suitable electrophilic fluorine sources include N-fluorobenzenesulfonimide.

Addition of primary and benzylic amines to tert-butyl 6-chloro-4-fluoropyridin-3-ylcarbamate IV afforded amines of the formula V. This conversion was achieved by treatment of IV with amines in solvents such as ethyl alcohol, isopropyl alcohol, dimethylformamide, dimethylactemide, toluene, dioxane and dichloroethane in the presence or absence of inorganic bases such as potassium carbonate or sodium bicarbonate or organic bases such as triethylamine, 4-methylmorpholine, pyridine or N,N-diisopropylethylamine at temperatures ranging from room temperature to 110° C. Amines of the formula V were converted to diamines of the formula VI by removing the carbamate protecting group under standard conditions, as described in Green, T., Wuts, P. *Protecting Groups in Organic Synthesis*, John Wiley & Sons, INC, Second edition, 1991, pp 309-405.

The diamines of formula VI were converted to the diones of formula VIII using various reaction procedures. In one procedure, this conversion was achieved by refluxing an aqueous solution of VI in the presence of oxalic acid and a catalytic amount of a mineral acid such as HCl. Alternatively, this conversion to structures of formula VII was achieved by addition of either methyl chlorooxoacetate or oxalyl chloride to a solution of VI in the presence of an organic base such as triethylamine, 4-methylmorpholine, or N,N-diisopropylethylamine, at 0° C., followed by warming to either room temp or the reflux temperature of the solvent. Suitable solvents include toluene, dichloromethane, dicholroethane, dioxane, or tetrahydrofuran.

The chloroimidate of formula VIII was prepared by a number of methods. In one procedure, a dione of formula VII was heated to reflux in the presence of phosphorous oxychloride and a phase transfer catalyst such as tetraethylammonium chloride. Suitable solvents for this reaction include propionitrile or acetonitrile. In an alternate procedure, the formation of chloroimidate VII was achieved by dissolving VII in a suitable solvent such as dichloromethane, tetrahydrofuran, or dioxane and treating it with oxalyl chloride in the presence of a catalytic amount of dimethylformamide between 0° C. and room temperature.

The 6-aminopyrazinones of formula IX were prepared by the addition of various primary and secondary amines to chloroimidate VIII in the presence of an organic base such as triethylamine, 4-methylmorpholine, or N,N-diisopropylethylamine at temperatures ranging from 0° C. to room temperature. Suitable solvents include dichloromethane, tetrahydrofuran, and dioxane. Formation of the desired pteridinone of formula I was prepared through a standard palladium catalyzed Suzuki coupling between chloride IX and suitable boronic acids, as described in Miyaura, N., Suzuki, A; *Chem Rev.* 1995, 95, 2457-2483. A solution of the chloride, IX, in a suitable solvent such as tetrahydrofuran or dioxane was heated to reflux in the presence of the desired boronic, an inorganic base such as sodium carbonate or cesium carbonate, and a palladium(0) source such palladium(II) acetate or tetrakis(triphenylphosphine)palladium to give compounds of formula I.

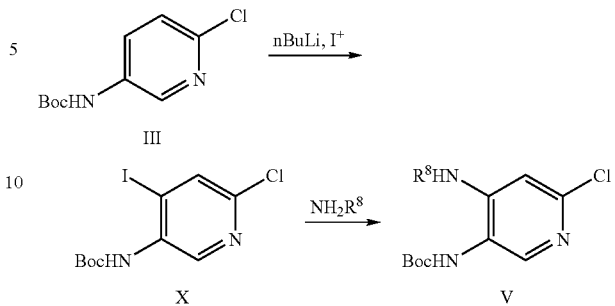

Scheme 2

Scheme 2 outlines an alternate conversion of tert-butyl 6-chloropyridin-3-ylcarbamate III to amines of formula V.

tert-butyl 6-chloropyridin-3-ylcarbamate III was converted to tert-butyl 6-chloro-4-iodopyridin-3-ylcarbamate X by metallation followed by quenching with an electrophilic iodine source. Lithation was achieved be treating tert-butyl 6-chloropyridin-3-ylcarbamate III with an organolithium such as n-butyl lithium or t-butyl lithium in the presence or absence of additives such as N,N,N',N'-tetramethylethylenediamine in solvents such as diethyl ether or tetrahydrofuran at temperatures ranging from −80° C. to 0° C. Suitable electrophilic iodine sources include molecular iodine and 1-iodopyrrolidine-2,5-dione. Addition of primary and benzylic amines to tert-butyl 6-chloro-4-iodopyridin-3-ylcarbamate IV afforded amines of the formula V.

Amines of the formula X were converted to diamines of the formula V by standard coupling techniques as described in Ley, S., Thomas, A.; *Angew. Chem. Int. Ed.* 2003, 42, 5400-5449. A solution of iodide, X, in a suitable solvent such as tetrahydrofuran, dioxane, toluene, benzene, N,N dimethylformamide, isopropanol, ethanol or propionitrile was stirred at temperatures ranging from room temperature to reflux in the presence of the desired amine, a base such as sodium carbonate, cesium carbonate, potassium phosphate, or sodium tert-butoxide and a palladium with ligand and/or a copper source. Suitable sources of palladium include palladium(II) acetate, tetrakis(triphenylphosphine)palladium, dichloro[1,1'-bis(diphenylphosphino)ferrocene]palladium (II) dichloromethane adduct and tris(dibenzylideneacetone)dipalladium(0). Suitable ligands include triphenylphosphine, tri-2-furylphosphine, 4,5-bis(diphenylphosphine)-9-9-dimethylxathene, tricyclohexylphospine, tert-butylphospine and 2,2'-bis(diphenylphosphino)-1,1'-binapthyl. Suitable sources of copper include copper(II) acetate, copper(I) iodide and copper(I) chloride.

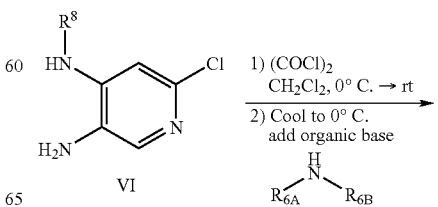

Scheme 3

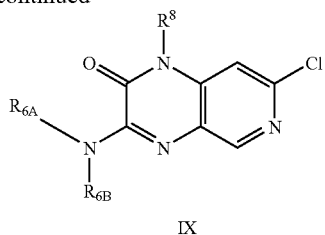

Scheme 3 outlines a one-pot procedure for the conversion of diaminopyridine of formula VI to amino substituted pyrazinone of formula IX.

The pyridine VI was dissolved in a solvent such as dichloromethane, tetrahydrofuran, or dioxane and cooled to 0° C. The mixture was treated with oxalyl chloride and allowed to slowly warm to room temperature. The reaction was typically mixed for 4-24 hours. The reaction mixture was then recooled to 0° C., treated with an organic base such as triethylamine, 4-methylmorpholine, or N,N-diisopropylethylamine, followed by addition of the requisite primary or secondary amine leading to isolation of the desired amine of formula IX.

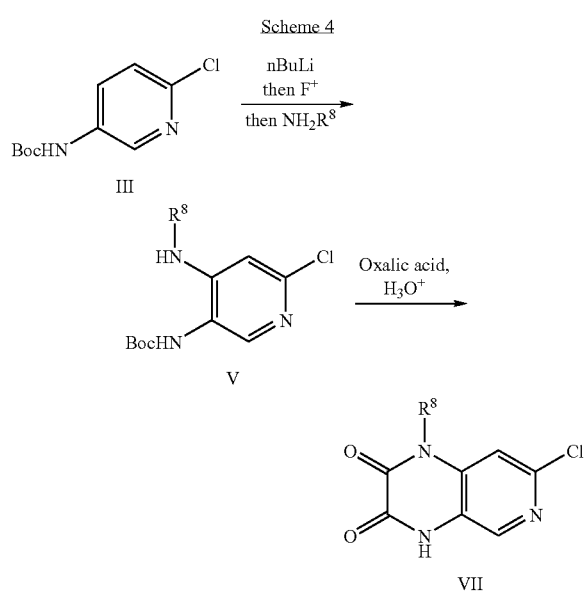

Scheme 4 outlines an alternate conversion of tert-butyl 6-chloropyridin-3-ylcarbamate III to diones of formula VII.

tert-butyl 6-chloropyridin-3-ylcarbamate III was converted to amines of formula V by metallation followed by quenching with an electrophilic fluorine source and displacement of the fluorine with primary or benzylic amines.

Lithation was achieved be treating tert-butyl 6-chloropyridin-3-ylcarbamate III with an organolithium such as n-butyl lithium or t-butyl lithium in the presence or absence of additives such as N,N,N',N'-tetramethylethylenediamine in solvents such as diethyl ether or tetrahydrofuran at temperatures ranging from −80° C. to 0° C. Suitable electrophilic fluorine sources include N-fluorobenzenesulfonimide.

Addition of primary and benzylic amines to the intermediate tert-butyl 6-chloro-4-fluoropyridin-3-ylcarbamate afforded amines of the formula V. This conversion was achieved by treatment of the crude tert-butyl 6-chloro-4-fluoropyridin-3-ylcarbamate with amines in solvents such as ethyl alcohol, isopropyl alcohol, dimethylformamide, dimethylactemide, toluene, dioxane and dichloroethane in the presence or absence of inorganic bases such as potassium carbonate or sodium bicarbonate or organic bases such as triethylamine, 4-methylmorpholine, pyridine or N,N-diisopropylethylamine at temperatures ranging from room temperature to 110° C.

Amines of the formula V were converted to diones of the formula VII by treatment with oxalic acid and additional protic acids such as HCl at temperatures ranging from 25° C. to 110° C., or in a stepwise fashion as detailed in Scheme 1.

COMPOUND EXAMPLES

The following illustrate the synthesis of various compounds of the Formulae (I)-(I-32). Other compounds of this invention may be prepared using the methods illustrated in these Examples, either alone or in combination with techniques generally known in the art.

Example 1

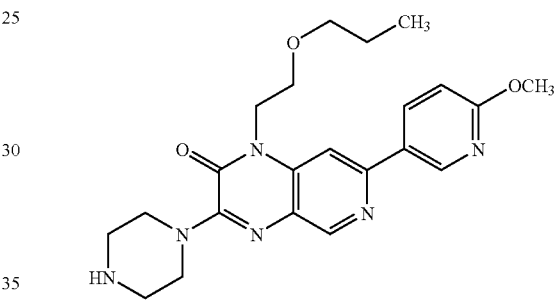

7-(6-methoxypyridin-3-yl)-3-(piperazin-1-yl)-1-(2-propoxyethyl)pyrido[3,4-b]pyrazin-2(1H)-one Step 1: Preparation of tert-butyl 6-chloropyridin-3-ylcarbamate A solution of 5-amino-2-chloropyridine (30.94 g, 236 mmol, Aldrich) and di-tert-butyldicarbonate (65.36 g, 299 mmol, Aldrich) in 1,4-dioxane (300 mL) was stirred at reflux for 20 hours. Additional di-tert-butyldicarbonate (8.30 g, 38 mmol) was added and the reaction was stirred at reflux for 7 hours. The reaction was cooled to room temperature and poured into water. The layers were separated and the aqueous layer was extracted with ethyl acetate. The combined organic layers were washed with brine, dried over magnesium sulfate, and solvent was removed at reduced pressure to give a brown oil. The oil was triturated with diethyl ether and filtered to give tert-butyl 6-chloropyridin-3-ylcarbamate as a tan solid. (49.84 g, 92% yield). $^1$H NMR (CDCl$_3$) δ 8.24 (m, 1H), 7.96 (1H), 7.27 (1H), 6.65 (1H), 1.51 (9H).

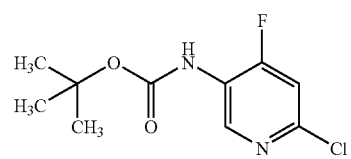

Step 2: Preparation of tert-butyl 6-chloro-4-fluoropyridin-3-ylcarbamate

To a −63° C. solution of tert-butyl 6-chloropyridin-3-ylcarbamate (24.99 g, 109.3 mmol) and TMEDA (39 mL, 260.0 mmol, Aldrich) in diethyl ether (700 mL) was added a 1.6M n-butyl lithium solution in hexane (193 mL, 308.8 mmol, Aldrich) over a period of 30 minutes while maintaining the temperature of the reaction at −60° to −50° C. The reaction was stirred at −60° C. for an additional 10 minutes after the addition was complete then warmed to −10° C. and stirred at −25° to −10° C. for 2.0 hours. The reaction was cooled to −60° C. and a solution of N-fluorobenzenesulfonimide (53.49 g, 169.6 mmol, Aldrich) in tetrahydrofuran (155 mL) was added while keeping the temperature below −50° C. It precipitated on addition and stirring became difficult. The reaction was then allowed to slowly warm to 0° C. over 1 hour. The reaction was quenched with saturated ammonium chloride solution (400 mL). The layers were separated and the aqueous layer was extracted with ethyl acetate (2×250 mL). The combined organic layers were washed with brine, dried over magnesium sulfate, and solvent was removed at reduced pressure to give an oily brown solid. The material was passed through a column of silica gel with 20% ethyl acetate/hexane. The 6-chloro-4-fluoropyridin-3-ylcarbamate was obtained as a yellow solid. (15.88 g, 59% yield). $^1$H NMR (CDCl$_3$) δ 9.09 (1H), 7.12 (1H), 6.55 (1H), 1.54 (s, 9H).

Step 3: Preparation of tert-butyl 6-chloro-4-[(2-propoxyethyl)amino]pyridin-3-ylcarbamate

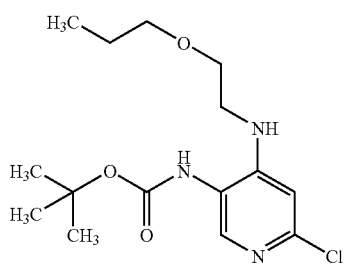

A solution of tert-butyl 6-chloro-4-fluoropyridin-3-ylcarbamate (11.96 g, 48.5 mmol) and 2-n-propoxyethylamine (11.8 mL, 97.2 mmol, TCI) in ethanol (120 mL) was stirred at reflux for 22 hours. The reaction was cooled to room temperature and solvent was removed at reduced pressure to give a yellow solid which was triturated with diethyl ether and filtered to give 6-chloro-4-[(2-propoxyethyl)amino]pyridin-3-ylcarbamate as a white solid. (13.08 g, 82% yield). $^1$H NMR (CDCl$_3$) δ 7.92 (1H), 6.54 (1H), 5.77 (1H), 5.11 (1H), 3.65 (2H), 3.44 (2H), 3.34-3.29 (2H), 1.65-1.56 (2H), 1.49 (9H), 0.94 (3H).

Step 4: Preparation of 6-chloro-N$^4$-(2-propoxyethyl)pyridine-3,4-diamine

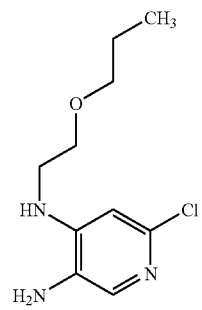

A solution of tert-butyl 6-chloro-4-[(2-propoxyethyl)amino]pyridin-3-ylcarbamate (7.08 g, 21.4 mmol) in 1,4-dioxane (20 mL) was treated with 4N HCl in 1,4-dioxane (100 mL) and stirred at room temperature for one hour. The reaction was partitioned between ethyl acetate and saturated sodium bicarbonate solution. The layers were separated and the aqueous layer was extracted with ethyl acetate. The combined organic layers were washed with brine, dried over magnesium sulfate, and solvent was removed at reduced pressure to give 6-chloro-N$^4$-(2-propoxyethyl)pyridine-3,4-diamine as a brown oil. (4.93 g, 100% yield). $^1$H NMR (CDCl$_3$) δ 7.63 (1H), 6.45 (1H), 4.67 (1H), 3.67 (2H), 3.43 (2H), 3.32-3.27 (2H), 2.92 (2H), 1.64-1.55 (2H), 0.93 (3H).

Step 5: Preparation of 3,7-dichloro-1-(2-propoxyethyl)pyrido[3,4-b]pyrazin-2(1H)-one

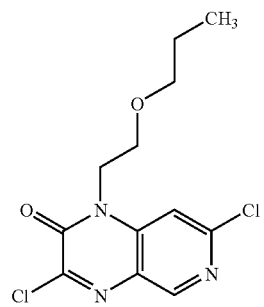

A 0° C. solution of 6-chloro-N$^4$-(2-propoxyethyl)pyridine-3,4-diamine (2.80 g, 12.2 mmol) and diisopropylethylamine (4.6 mL, 25.7 mmol) in dichloromethane (100 mL) was treated with methyl chlorooxoacetate (1.1 mL, 11.7 mmol, Aldrich), allowed to warm to room temperature and stirred for four hours. The reaction was diluted with dichloromethane and washed with saturated sodium bicarbonate solution, dried over magnesium sulfate, and solvent was removed at reduced pressure. The residue was dissolved in toluene (30 mL) and heated at 105° C. for four hours. The solvent was removed at reduced pressure and the resulting solid taken up in dichloromethane (100 mL) and treated with oxalyl chloride (2.1 mL, 24.1 mmol) and DMF (3 drops). The reaction was stirred at room temperature for 6 hours. The solvent was removed at reduced pressure to give a brown solid. This was passed through a column of silica gel with 70% ethyl acetate/hexane to give 3,7-dichloro-1-(2-propoxyethyl)pyrido[3,4-b]pyrazin-2(1H)-one as a white solid. (2.44 g, 66% yield). ¹H NMR (CDCl₃) δ 8.78 (1H), 7.59 (1H), 4.40 (2H), 3.80 (2H), 3.35 (2H), 1.52-1.46 (2H), 0.82 (3H).

Step 6: 7-chloro-3-(piperazin-1-yl)-1-(2-propoxyethyl)pyrido[3,4-b]pyrazin-2(1H)-one

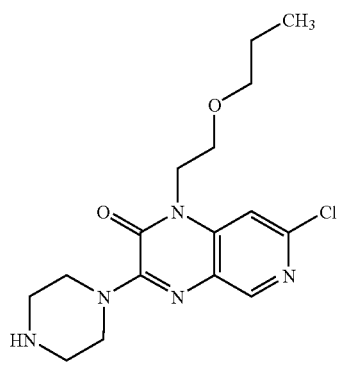

A solution of 3,7-dichloro-1-(2-propoxyethyl)pyrido[3,4-b]pyrazin-2(1H)-one (193 mg, 0.64 mmol), piperazine (118 mg, 0.91 mmol, Aldrich) and triethylamine (0.15 mL, 1.07 mmol) in THF (3 mL) was stirred at room temperature for one hour. The reaction was partitioned between ethyl acetate and water. The layers were separated and the aqueous layer was extracted with ethyl acetate. The combined organic layers were washed with brine, dried over magnesium sulfate, and solvent was removed at reduced pressure to give a brown oil. This was passed through a column of silica gel with 80-100% ethyl acetate/hexane to give 7-chloro-3-(piperazin-1-yl)-1-(2-propoxyethyl)pyrido[3,4-b]pyrazin-2(1H)-one. (183 mg, 72% yield).

Step 7: Preparation of 7-(6-methoxypyridin-3-yl)-3-(piperazin-1-yl)-1-(2-propoxyethyl)pyrido[3,4-b]pyrazin-2(1H)-one A solution of 7-chloro-3-(piperazin-1-yl)-1-(2-propoxyethyl)pyrido[3,4-b]pyrazin-2(1H)-one (72 mg, 0.18 mmol) in 1,4-dioxane (2.5 mL) was treated with tetrakis(triphenylphosphine) palladium(0) (19 mg, 0.016 mmol, Strem) and stirred at room temperature for five minutes. A warm solution of 2-methoxy-5-pyridineboronic acid (41 mg, 0.27 mmol, Frontier) in ethanol (0.5 mL) and 2.0 M aqueous sodium carbonate 1.5 mL) were added. The mixture was refluxed for 2.0 hours, filtered hot through celite and the filtrate was concentrated under reduced pressure. The residue was partitioned between ethyl acetate and water, and the layers were separated. The aqueous layer was extracted with ethyl acetate. The combined organic layers were washed with brine, dried over magnesium sulfate, concentrated under reduced pressure, and passed through a column of silica gel with 2% methanol/dichloromethane. Fractions were concentrated at reduced pressure and triturated with diethyl ether. The 7-(6-methoxypyridin-3-yl)-3-(piperazin-1-yl)-1-(2-propoxyethyl)pyrido[3,4-b]pyrazin-2(1H)-one was obtained as a pink powder.

¹H NMR (CDCl₃) δ8.77-8.74 (2H), 8.27-8.23 (1H), 7.64 (1H), 6.85 (1H), 4.42 (2H), 4.00-3.95 (7H), 3.79 (2H), 3.37 (2H), 3.07-3.03 (4H), 1.53-1.46 (2H), 0.78 (3H); HRMS m/z 425.2293 (calcd for M+H, 425.2296).

Example 2

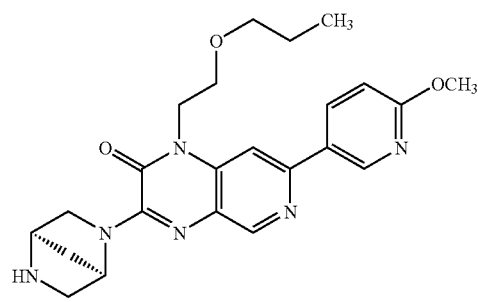

3-[(1R,4R)-2,5-diazabicyclo[2.2.1]hept-2-yl]-7-(6-methoxypyridin-3-yl)-1-(2-propoxyethyl)pyrido[3,4-b]pyrazin-2(1H)-one Prepared as described in example 1 using (1R,4R)-2,5-diazabicyclo[2.2.1]heptane in step 6.

¹H NMR (CDCl₃) δ8.74-8.70 (2H), 8.41-8.22 (1H), 7.59 (1H), 6.84 (1H), 4.39 (2H), 4.00 (3H), 3.85-3.73 (5H), 3.37 (2H), 3.17 (2H), 1.87-1.76 (2H), 1.54-1.47 (3H), 0.87-0.76 (4H); HRMS m/z 437.2316 (calcd for M+H, 437.2296).

Example 3

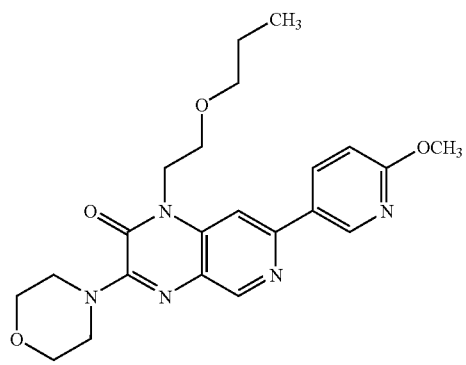

7-(6-methoxypyridin-3-yl)-3-morpholin-4-yl-1-(2-propoxyethyl)pyrido[3,4-b]pyrazin-2(1H)-one Prepared as described in example 1 using morpholine in step 6.

¹H NMR (CDCl₃) δ 8.77-8.75 (2H), 8.24 (1H), 7.64 (1H), 6.86 (1H), 4.42 (2H), 4.02-4.00 (7H), 3.86-3.83 (4H), 3.79

(2H), 3.36 (2H), 1.53-1.46 (2H), 0.78 (3H); HRMS m/z 426.2109 (calcd for M+H, 426.2136).

Example 4

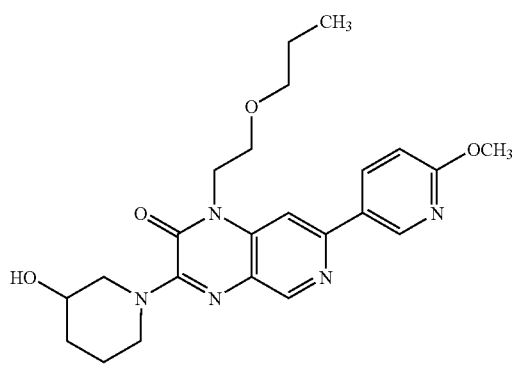

3-(3-hydroxypiperidin-1-yl)-7-(6-methoxypyridin-3-yl)-1-(2-propoxyethyl)pyrido[3,4-b]pyrazin-2(1H)-one Prepared as described in example 1 using 3-hydroxypiperidine in step 6.

$^1$H NMR (CDCl$_3$) δ 8.76 (2H), 8.28-8.25 (1H), 7.65 (1H), 6.86 (1H), 4.43 (2H), 4.17-4.14 (2H), 4.06 (1H), 4.01 (3H), 3.84-3.69 (4H), 3.37 (2H), 2.84 (1H), 1.97-1.92 (1H), 1.88-1.84 (2H), 1.54-1.47 (2H), 0.78 (3H); HRMS m/z 440.2280 (calcd for M+H, 440.2292).

Example 5

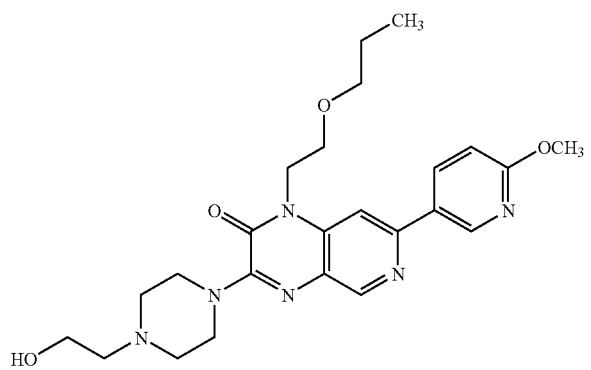

3-[4-(2-hydroxyethyl)piperazin-1-yl]-7-(6-methoxypyridin-3-yl)-1-(2-propoxyethyl)pyrido[3,4-b]pyrazin-2(1H)-one Step 1: Preparation of tert-butyl 6-chloropyridin-3-ylcarbamate A solution of 5-amino-2-chloropyridine (30.94 g, 236 mmol, Aldrich) and di-tert-butyldicarbonate (65.36 g, 299 mmol, Aldrich) in 1,4-dioxane (300 mL) was stirred at reflux for 20 hours. Additional di-tert-butyldicarbonate (8.30 g, 38 mmol) was added and the reaction was stirred at reflux for 7 hours. The reaction was cooled to room temperature and poured into water. The layers were separated and the aqueous layer was extracted with ethyl acetate. The combined organic layers were washed with brine, dried over magnesium sulfate, and solvent was removed at reduced pressure to give a brown oil. The oil was triturated with diethyl ether and filtered to give tert-butyl 6-chloropyridin-3-ylcarbamate as a tan solid. (49.84 g, 92% yield). $^1$H NMR (CDCl$_3$) δ 8.24 (m, 1H), 7.96 (1H), 7.27 (1H), 6.65 (1H), 1.51 (9H).

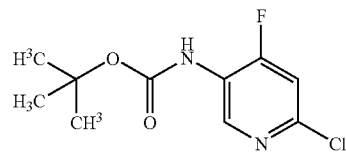

Step 2: Preparation of tert-butyl 6-chloro-4-fluoropyridin-3-ylcarbamate

To a −63° C. solution of tert-butyl 6-chloropyridin-3-ylcarbamate (24.99 g, 109.3 mmol) and TMEDA (39 mL, 260.0 mmol, Aldrich) in diethyl ether (700 mL) was added a 1.6M n-butyl lithium solution in hexane (193 mL, 308.8 mmol, Aldrich) over a period of 30 minutes while maintaining the temperature of the reaction at −60° to −50° C. The reaction was stirred at −60° C. for an additional 10 minutes after the addition was complete then warmed to −10° C. and stirred at −25° to −10° C. for 2.0 hours. The reaction was cooled to −60° C. and a solution of N-fluorobenzenesulfonimide (53.49 g, 169.6 mmol, Aldrich) in tetrahydrofuran (155 mL) was added while keeping the temperature below −50° C. It precipitated on addition and stirring became difficult. The reaction was then allowed to slowly warm to 0° C. over 1 hour. The reaction was quenched with saturated ammonium chloride solution (400 mL). The layers were separated and the aqueous layer was extracted with ethyl acetate (2×250 mL). The combined organic layers were washed with brine, dried over magnesium sulfate, and solvent was removed at reduced pressure to give an oily brown solid. The material was passed through a column of silica gel with 20% ethyl acetate/hexane. The 6-chloro-4-fluoropyridin-3-ylcarbamate was obtained as a yellow solid. (15.88 g, 59% yield). $^1$H NMR (CDCl$_3$) δ 9.09 (1H), 7.12 (1H), 6.55 (1H), 1.54 (s, 9H).

Step 3: Preparation of tert-butyl 6-chloro-4-[(2-propoxyethyl)amino]pyridin-3-ylcarbamate

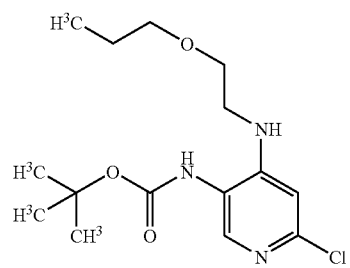

A solution of tert-butyl 6-chloro-4-fluoropyridin-3-ylcarbamate (11.96 g, 48.5 mmol) and 2-n-propoxyethylamine (11.8 mL, 97.2 mmol, TCI) in ethanol (120 mL) was stirred at reflux for 22 hours. The reaction was cooled to room temperature and solvent was removed at reduced pressure to give a yellow solid which was triturated with diethyl ether and filtered to give 6-chloro-4-[(2-propoxyethyl)amino]pyridin- 3-ylcarbamate as a white solid. (13.08 g, 82% yield). $^1$H NMR (CDCl$_3$) δ 7.92 (1H), 6.54 (1H), 5.77 (1H), 5.11 (1H), 3.65 (2H), 3.44 (2H), 3.34-3.29 (2H), 1.65-1.56 (2H), 1.49 (9H), 0.94 (3H).

Step 4: Preparation of 6-chloro-N$^4$-(2-propoxyethyl) pyridine-3,4-diamine

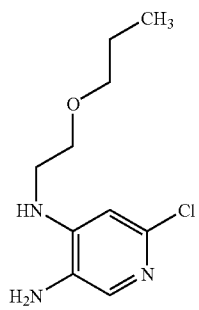

A solution of tert-butyl 6-chloro-4-[(2-propoxyethyl) amino]pyridin-3-ylcarbamate (7.08 g, 21.4 mmol) in 1,4-dioxane (20 mL) was treated with 4N HCl in 1,4-dioxane (100 mL) and stirred at room temperature for one hour. The reaction was partitioned between ethyl acetate and saturated sodium bicarbonate solution. The layers were separated and the aqueous layer was extracted with ethyl acetate. The combined organic layers were washed with brine, dried over magnesium sulfate, and solvent was removed at reduced pressure to give 6-chloro-N$^4$-(2-propoxyethyl)pyridine-3,4-diamine as a brown oil. (4.93 g, 100% yield). $^1$H NMR (CDCl$_3$) δ 7.63 (1H), 6.45 (1H), 4.67 (1H), 3.67 (2H), 3.43 (2H), 3.32-3.27 (2H), 2.92 (2H), 1.64-1.55 (2H), 0.93 (3H).

Step 5: Preparation of 3,7-dichloro-1-(2-propoxyethyl)pyrido[3,4-b]pyrazin-2(1H)-one

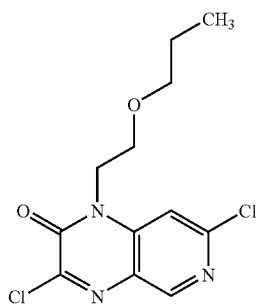

A 0° C. solution of 6-chloro-N$^4$-(2-propoxyethyl)pyridine-3,4-diamine (2.80 g, 12.2 mmol) and diisopropylethylamine (4.6 mL, 25.7 mmol) in dichloromethane (100 mL) was treated with methyl chlorooxoacetate (1.1 mL, 11.7 mmol, Aldrich), allowed to warm to room temperature and stirred for four hours. The reaction was diluted with dichloromethane and washed with saturated sodium bicarbonate solution, dried over magnesium sulfate, and solvent was removed at reduced pressure. The residue was dissolved in toluene (30 mL) and heated at 105° C. for four hours. The solvent was removed at reduced pressure and the resulting solid taken up in dichloromethane (100 mL) and treated with oxalyl chloride (2.1 mL, 24.1 mmol) and DMF (3 drops). The reaction was stirred at room temperature for 6 hours. The solvent was removed at reduced pressure to give a brown solid. This was passed through a column of silica gel with 70% ethyl acetate/hexane to give 3,7-dichloro-1-(2-propoxyethyl)pyrido[3,4-b]pyrazin-2(1H)-one as a white solid. (2.44 g, 66% yield). $^1$H NMR (CDCl$_3$) δ 8.78 (1H), 7.59 (1H), 4.40 (2H), 3.80 (2H), 3.35 (2H), 1.52-1.46 (2H), 0.82 (3H).

In the alternative, the conversion of 6-chloro-N$^4$-(2-propoxyethyl)pyridine-3,4-diamine from Step 3 to the 7-chloro-1-(2-propoxyethyl)pyrido[4,3-b]pyrazine-2,3(1H,4H)-dione of Step 5 can be conducted in a one-pot synthesis using an aqueous solvent as described in Steps V to VII in Scheme 4.

Step 6: 7-chloro-3-[4-(2-hydroxyethyl)piperazin-1-yl]-1-(2-propoxyethyl)pyrido[3,4-b]pyrazin-2(1H)-one

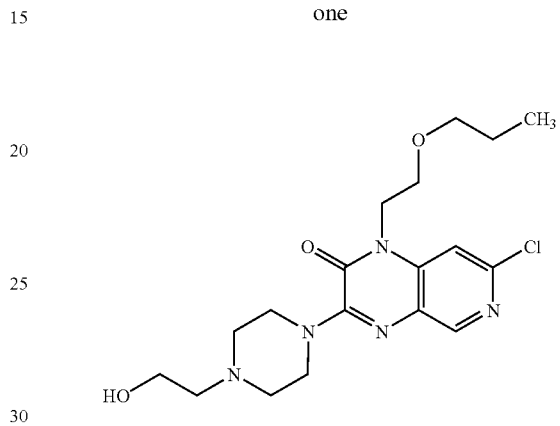

A solution of 3,7-dichloro-1-(2-propoxyethyl)pyrido[3,4-b]pyrazin-2(1H)-one (200 mg, 0.66 mmol), 1-(2-hydroxyethyl)piperazine (117 mg, 0.90 mmol, Aldrich) and triethylamine (0.27 mL, 1.94 mmol) in THF (3 mL) was stirred at room temperature for one hour. The reaction was partitioned between ethyl acetate and water. The layers were separated and the aqueous layer was extracted with ethyl acetate. The combined organic layers were washed with brine, dried over magnesium sulfate, and solvent was removed at reduced pressure to give 7-chloro-3-[4-(2-hydroxyethyl)piperazin-1-yl]-1-(2-propoxyethyl)pyrido[3,4-b]pyrazin-2(1H)-one. (218 mg, 83% yield). $^1$H NMR (CDCl$_3$) δ 8.48 (1H), 7.34 (1H), 4.33-4.30 (2H), 4.04-4.00 (4H), 3.76-3.72 (2H), 3.69-3.65 (2H), 3.38-3.34 (2H), 2.67-2.64 (4H), 2.62-2.58 (2H), 1.55-1.48 (2H), 0.87-0.82 (3H).

Step 7: Preparation of 3-[4-(2-hydroxyethyl)piperazin-1-yl]-7-(6-methoxypyridin-3-yl)-1-(2-propoxyethyl)pyrido[3,4-b]pyrazin-2(1H)-one

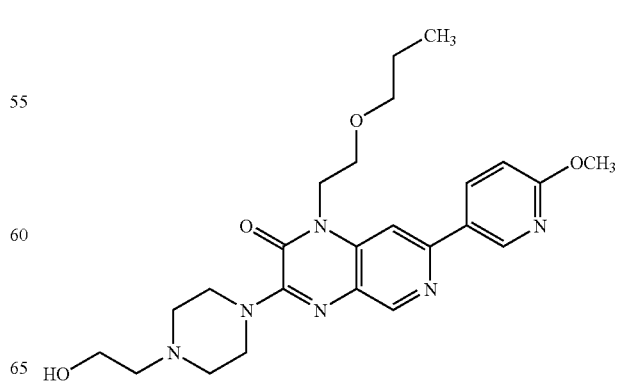

A solution of 7-chloro-3-[4-(2-hydroxyethyl)piperazin-1-yl]-1-(2-propoxyethyl)pyrido[3,4-b]pyrazin-2(1H)-one (218 mg, 0.55 mmol) in 1,4-dioxane (3.0 mL) was treated with tetrakis(triphenylphosphine) palladium(0) (19 mg, 0.016 mmol, Strem) and stirred at room temperature for five minutes. A warm solution of 2-methoxy-5-pyridineboronic acid (41 mg, 0.27 mmol, Frontier) in ethanol (0.5 mL) and 2.0 M aqueous sodium carbonate 1.5 mL) were added. The mixture was refluxed for 2.0 hours, filtered hot through celite and the filtrate was concentrated under reduced pressure. The residue was partitioned between ethyl acetate and water, and the layers were separated. The aqueous layer was extracted with ethyl acetate. The combined organic layers were washed with brine, dried over magnesium sulfate, concentrated under reduced pressure, and passed through a column of silica gel with 2.5% methanol/dichloromethane. Fractions were concentrated at reduced pressure and triturated with diethyl ether. The 7-(6-methoxypyridin-3-yl)-3-(piperazin-1-yl)-1-(2-propoxyethyl)pyrido[3,4-b]pyrazin-2(1H)-one was obtained as a pink powder. $^1$H NMR (CDCl$_3$) δ 8.77-8.76 (2H), 8.24 (1H), 7.64 (1H), 6.86 (1H), 4.43 (2H), 4.06-4.03 (4H), 4.00 (3H), 3.79 (2H), 3.71-3.67 (2H), 3.37 (2H), 2.78 (1H), 2.72-2.69 (4H), 2.66-2.62 (2H), 1.53-1.46 (2H), 0.78 (3H); HRMS m/z 469.2572 (calcd for M+H, 469.2558).

Example 6

3-[3-(hydroxymethyl)piperidin-1-yl]-7-(6-methoxypyridin-3-yl)-1-(2-propoxyethyl)pyrido[3,4-b]pyrazin-2(1H)-one Prepared as described in example 1 using piperidin-3-yl-methanol in step 6.

$^1$H NMR (CDCl$_3$) δ 8.69 (1H), 8.67 (1H,), 8.16 (1H), 7.56 (1H), 6.78 (1H), 4.39-4.32 (2H), 3.94-3.81 (6H), 3.79-3.64 (4H), 3.56-3.52 (1H), 3.32 (2H), 2.05-1.95 (1H), 1.84-1.78 (1H), 1.70-1.62 (2H), 1.50-1.41 (3H), 0.73 (3H); HRMS m/z 454.2419 (calcd for M+H, 454.2449).

Example 7

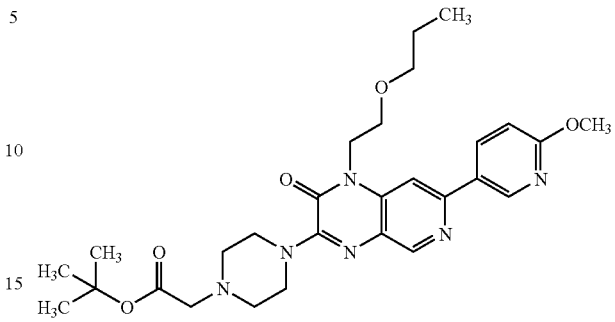

tert-butyl {4-[7-(6-methoxypyridin-3-yl)-2-oxo-1-(2-propoxyethyl)-1,2-dihydropyrido[3,4-b]pyrazin-3-yl]piperazin-1-yl}acetate Prepared as in example 1 using tert-butyl 2-(piperazin-1-yl)acetate in step 6.

$^1$H NMR (CDCl$_3$) δ 8.77-8.75 (2H), 8.24 (1H), 7.64 (1H), 6.86 (1H), 4.42 (2H), 4.08 (4H), 4.01 (3H), 3.78 (2H), 3.37 (2H), 3.19 (2H), 2.77 (4H), 1.53-1.44 (11H), 0.78 (3H). HRMS m/z 539.2949 (calcd for M+H, 539.2976).

Example 8

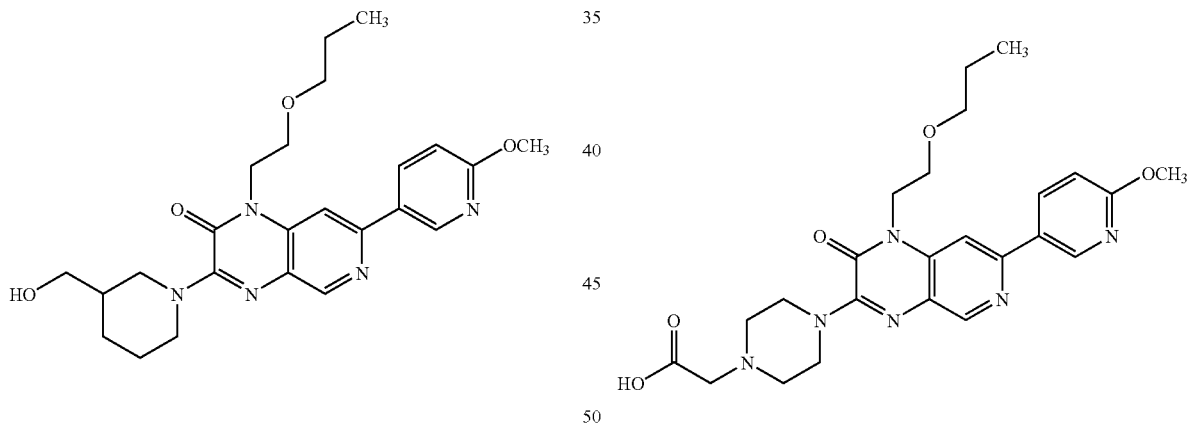

{4-[7-(6-methoxypyridin-3-yl)-2-oxo-1-(2-propoxyethyl)-1,2-dihydropyrido[3,4-b]pyrazin-3-yl]piperazin-1-yl}acetic acid A solution of tert-butyl {4-[7-(6-methoxypyridin-3-yl)-2-oxo-1-(2-propoxyethyl)-1,2-dihydropyrido[3,4-b]pyrazin-3-yl]piperazin1-yl}acetate (174 mg, 0.32 mmol) in dichloromethane (3 mL) was treated with trifluoroacetic acid (2 mL) and stirred at room temperature for 1 hour. The reaction mixture was concentrated under reduced pressure, triturated with diethyl ether, concentrated and recrystallized from ethyl acetate and hexane and filtered. The {4-[7-(6-methoxypyridin-3-yl)-2-oxo-1-(2-propoxyethyl)-1,2-dihydropyrido[3,4-b]pyrazin-3-yl]piperazin1-yl}acetic acid was obtained as a white solid. (81 mg, 52% yield).

¹H NMR (CD₃OD) δ 8.76-8.74 (2H), 8.24 (1H), 8.09 (1H), 7.02 (1H), 4.61 (2H), 4.40 (4H), 4.17 (2H), 4.02 (3H), 3.84 (2H), 3.61-3.59 (4H), 3.38 (2H), 1.47-1.40 (2H), 0.73 (3H). HRMS m/z 483.2361 (calcd for M+H, 483.2350).

Example 9

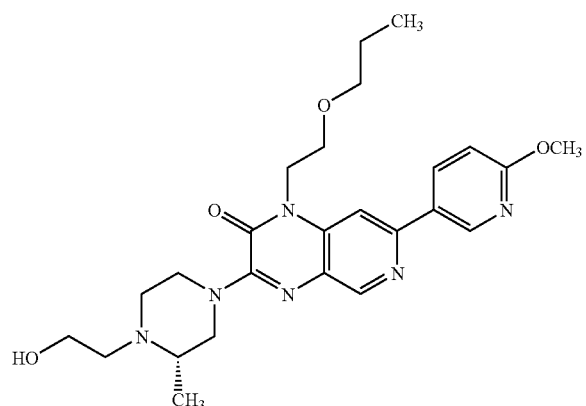

3-[(3S)-4-(2-hydroxyethyl)-3-methylpiperazin-1-yl]-7-(6-methoxypyridin-3-yl)-1-(2-propoxyethyl)pyrido[3,4-b]pyrazin-2(1H)-one Prepared as in example 1 using 2-((S)-2-methylpiperazin-1-yl)ethanol in step 6.

¹H NMR (CDCl₃) δ 8.77-8.75 (2H), 8.24 (1H), 7.64 (1H), 6.86 (1H), 4.44-4.40 (4H), 4.00 (3H), 3.79 (2H), 3.74-3.67 (1H), 3.63-3.57 (2H), 3.41-3.35 (3H), 3.04-2.96 (2H), 2.76-2.72 (2H), 2.53-2.43 (1H), 2.41-2.36 (1H), 1.53-1.44 (2H), 1.17 (3H), 0.78 (3H). HRMS m/z 483.2732 (calcd for M+H, 483.2714).

Example 10

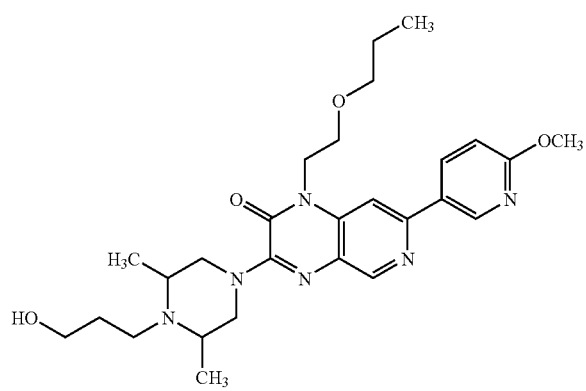

3-[4-(3-hydroxypropyl)-3,5-dimethylpiperazin-1-yl]-7-(6-methoxypyridin-3-yl)-1-(2-propoxyethyl)pyrido[3,4-b]pyrazin-2(1H)-one Prepared as in example 1 using 3-(2,6-dimethylpiperazin-1-yl)propan-1-ol in step 6. ¹H NMR (CDCl₃) δ 8.76-8.75 (2H), 8.24 (1H), 7.63 (1H), 6.86 (1H), 4.78-4.73 (2H), 4.42 (2H), 4.00 (3H), 3.97 (1H), 3.81-3.77 (4H), 3.37 (2H), 2.93-2.86 (4H), 2.70 (2H), 1.77-1.73 (2H), 1.53-1.46 (2H), 1.23 (6H), 0.78 (3H). HRMS m/z 511.3026 (calcd for M+H, 511.3027).

Example 11

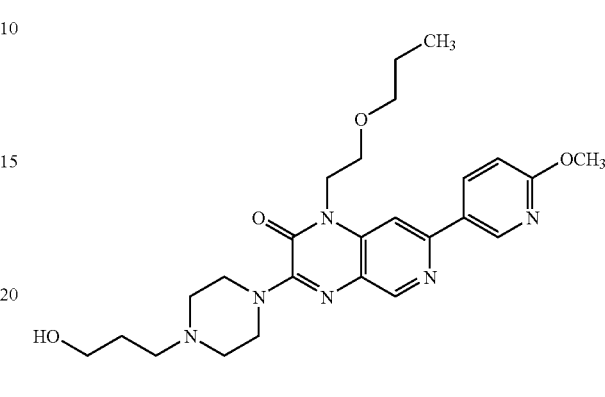

3-[4-(3-hydroxypropyl)piperazin-1-yl]-7-(6-methoxypyridin-3-yl)-1-(2-propoxyethyl)pyrido[3,4-b]pyrazin-2(1H)-one Prepared as in example 1 using 3-(piperazin-1-yl)propan-1-ol in step 6.

¹H NMR (CDCl₃) δ 8.78-8.76 (2H), 8.25 (1H), 7.65 (1H), 6.86 (1H), 4.42 (2H), 4.13-4.06 (4H), 4.01 (3H), 3.86 (2H), 3.79 (2H), 3.37 (2H), 2.76 (6H), 1.83 (2H), 1.53-1.46 (2H), 0.78 (3H). HRMS m/z 483.2747 (calcd for M+H, 483.2714).

Example 12

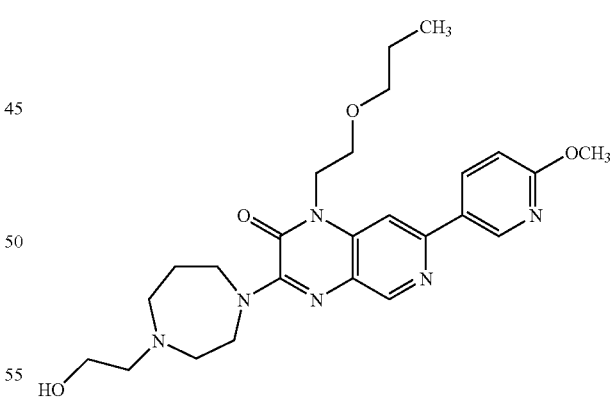

3-[4-(2-hydroxyethyl)-1,4-diazepan-1-yl]-7-(6-methoxypyridin-3-yl)-1-(2-propoxyethyl)pyrido[3,4-b]pyrazin-2(1H)-one Prepared as in example 1 using 2-(1,4-diazepan-1-yl)ethanol in step 6.

¹H NMR (CDCl₃) δ 8.75-8.73 (2H), 8.24 (1H), 7.60 (1H), 6.86 (1H), 4.41 (2H), 4.13-4.11 (2H), 4.05-4.00 (5H), 3.78

(2H), 3.64 (2H), 3.38 (2H), 3.03 (2H). 2.82-2.76 (4H), 2.12 (2H), 1.54-1.47 (2H), 0.80 (3H). HRMS m/z 483.2720 (calcd for M+H, 483.2714).

Example 13

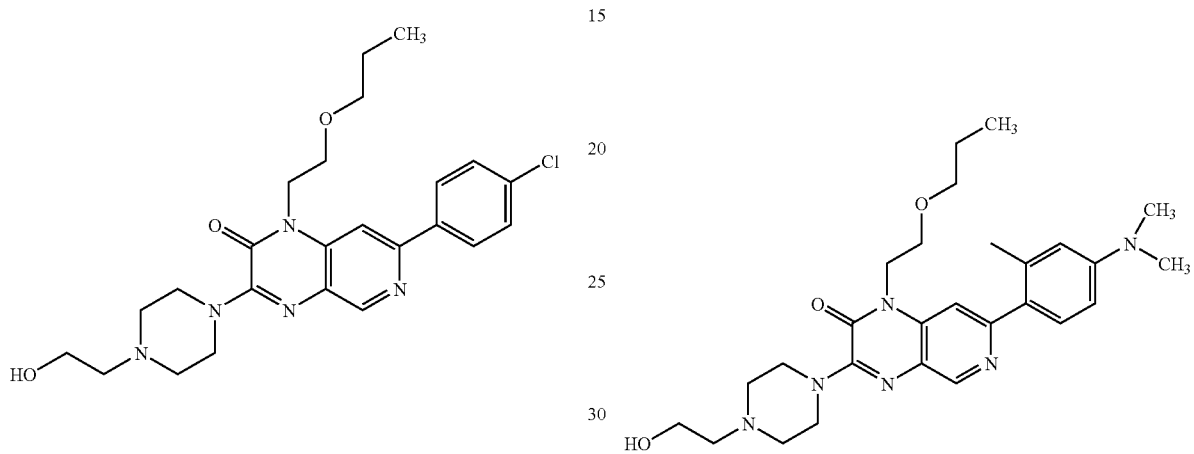

7-(4-chlorophenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol is step 6 and 4-chlorophenylboronic acid in step 7. HRMS m/z 472.2177 (calcd for M+H, 472.2115)

Example 14

3-(4-(2-hydroxyethyl)piperazin-1-yl)-7-(4-hydroxyphenyl)-1-(2-propoxyethyl)pyrido[3,4-b]pyrazin-2(1H)-one Prepared as in example 1 using 2-(piperazin-1-yl)ethanol in step 6 and 4-hydroxyphenylboronic acid in step 7. HRMS m/z 454.2456 (calcd for M+H, 454.2454).

Example 15

7-(4-(dimethylamino)-2-methylphenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 4-(dimethylamino)-2-methylphenylboronic acid in step 7. HRMS m/z 496.2983 (calcd for M+H, 496.3036).

Example 16

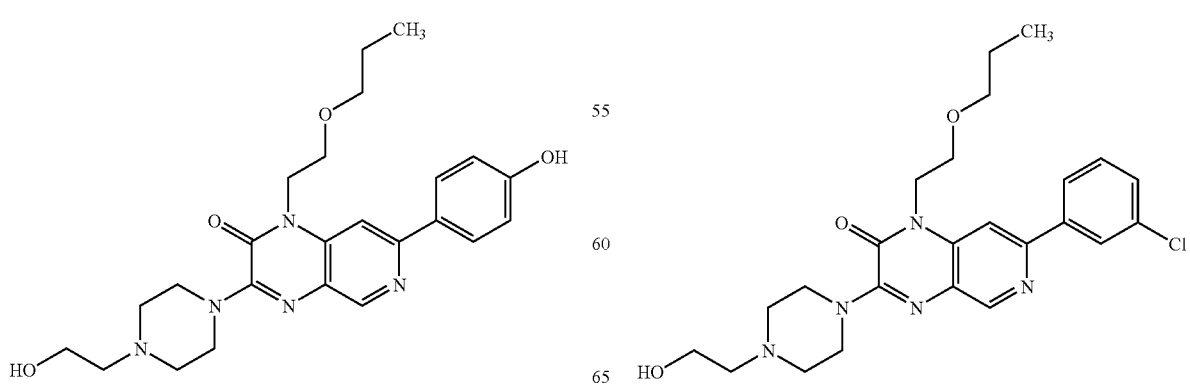

71

7-(3-chlorophenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 3-chlorophenylboronic acid in step 7. HRMS m/z 472.2095 (calcd for M+H, 472.2115).

Example 17

72

7-(2,4-difluorophenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 2,4-difluorophenylboronic acid in step 7. HRMS m/z 474.2299 (calcd for M+H, 474.2317).

Example 19

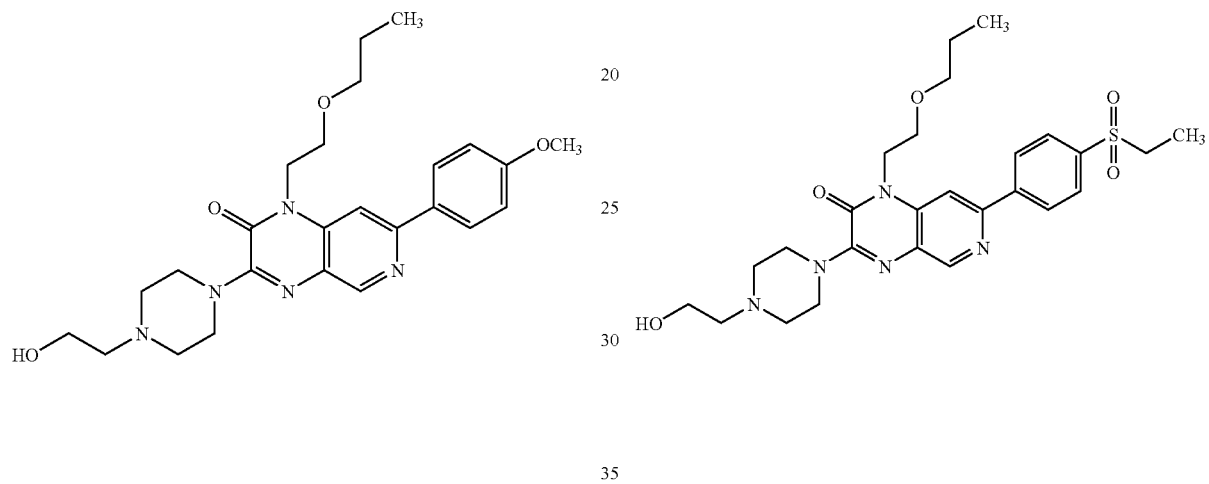

3-(4-(2-hydroxyethyl)piperazin-1-yl)-7-(4-methoxyphenyl)-1-(2-propoxyethyl)pyrido[3,4-b]pyrazin-2(1H)-one Prepared as in example 1 using 2-(piperazin-1-yl)ethanol in step 6 and 4-methoxyphenylboronic acid in step 7. HRMS m/z 468.2527 (calcd for M+H, 468.2611).

Example 18

7-(4-(ethylsulfonyl)phenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 4-(ethylsulfonyl)phenylboronic acid in step 7. HRMS m/z 530.2369 (calcd for M+H, 530.2437).

Example 20

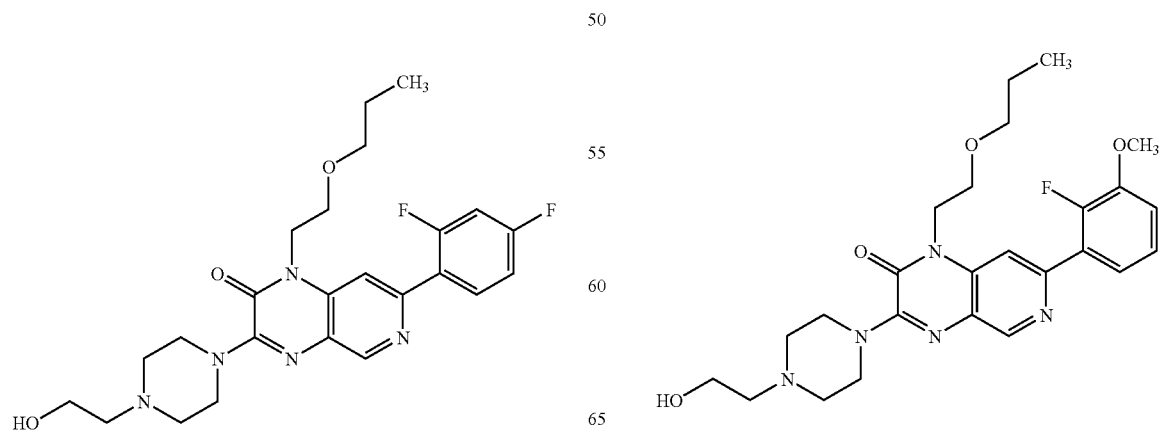

7-(2-fluoro-3-methoxyphenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 2-fluoro-3-methoxyphenylboronic acid in step 7. HRMS m/z 486.2464 (calcd for M+H, 486.2516).

Example 21

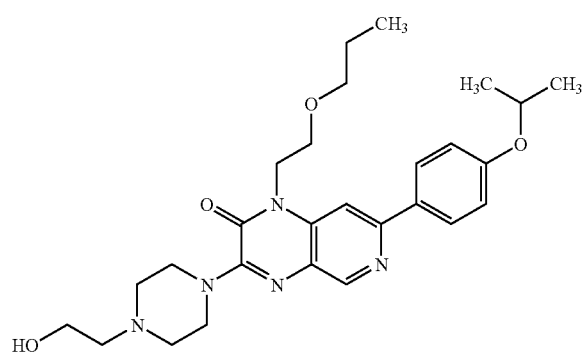

3-(4-(2-hydroxyethyl)piperazin-1-yl)-7-(4-isopropoxyphenyl)-1-(2-propoxyethyl)pyrido[3,4-b]pyrazin-2(1H)-one Prepared as in example 1 using 2-(piperazin-1-yl)ethanol in step 6 and 4-isopropoxyphenylboronic acid in step 7. HRMS m/z 496.2932 (calcd for M+H, 496.2924).

Example 22

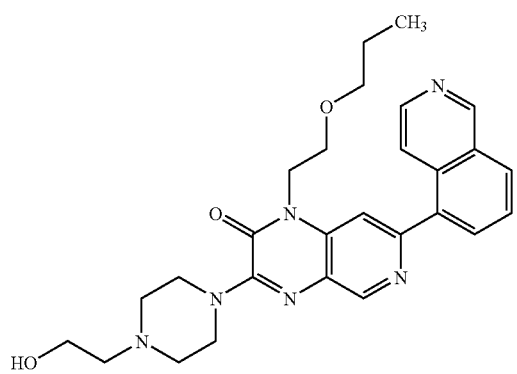

3-(4-(2-hydroxyethyl)piperazin-1-yl)-7-(isoquinolin-5-yl)-1-(2-propoxyethyl)pyrido[3,4-b]pyrazin-2(1H)-one Prepared as in example 1 using 2-(piperazin-1-yl)ethanol in step 6 and isoquinolin-5-yl-5-boronic acid in step 7. HRMS m/z 489.2621 (calcd for M+H, 489.2621).

Example 23

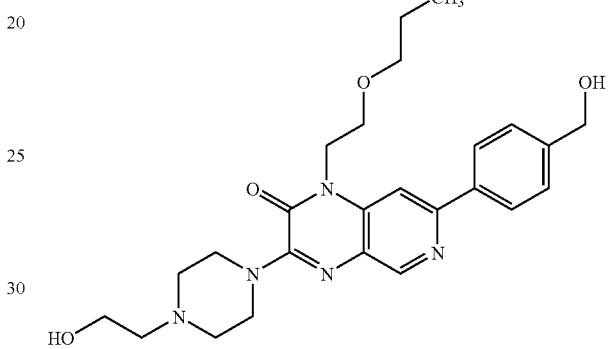

3-(4-(2-hydroxyethyl)piperazin-1-yl)-7-(4-(hydroxymethyl)phenyl)-1-(2-propoxyethyl)pyrido[3,4-b]pyrazin-2(1H)-one Prepared as in example 1 using 2-(piperazin-1-yl)ethanol in step 6 and 4-(hydroxymethyl)phenylboronic acid in step 7. HRMS m/z 468.2537 (calcd for M+H, 468.2611).

Example 24

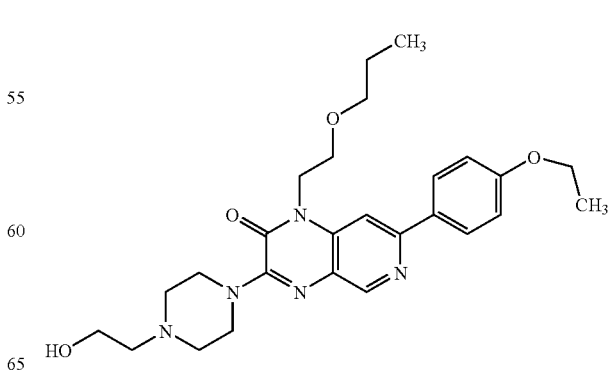

75

7-(4-ethoxyphenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 4-ethoxyphenylboronic acid in step 7. HRMS m/z 482.2747 (calcd for M+H, 482.2767).

Example 25

76

7-(2,3-difluorophenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 2,3-difluorophenylboronic acid in step 7. HRMS m/z 474.2396 (calcd for M+H, 474.2317).

Example 27

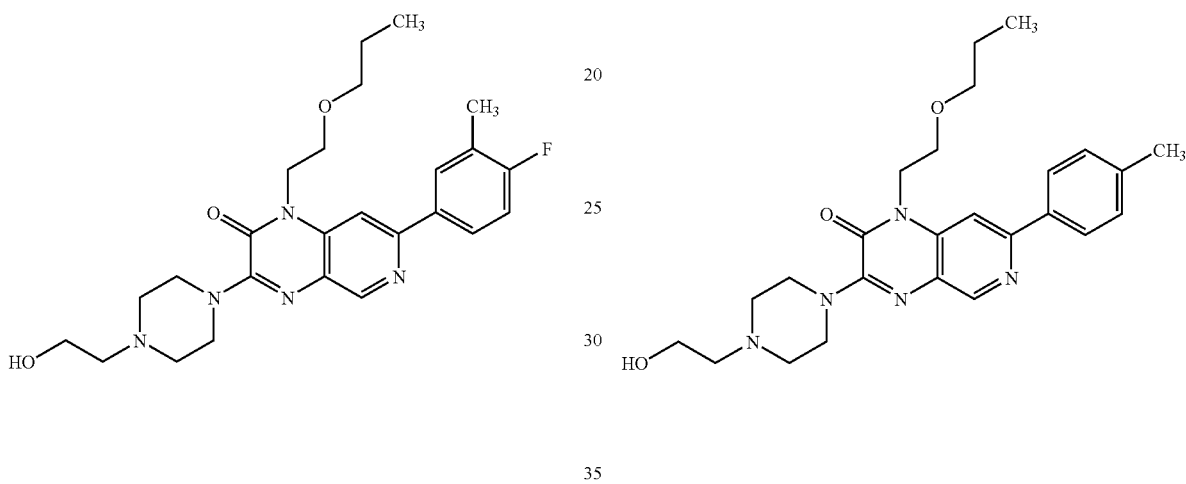

7-(4-fluoro-3-methylphenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 4-fluoro-3-methylphenylboronic acid in step 7. HRMS m/z 470.2620 (calcd for M+H, 470.2567).

Example 26

3-(4-(2-hydroxyethyl)piperazin-1-yl)-1-(2-propoxyethyl)-7-p-tolylpyrido[3,4-b]pyrazin-2(1H)-one Prepared as in example 1 using 2-(piperazin-1-yl)ethanol in step 6 and 4-methylphenylboronic acid in step 7. HRMS m/z 452.2651 (calcd for M+H, 452.2661).

Example 28

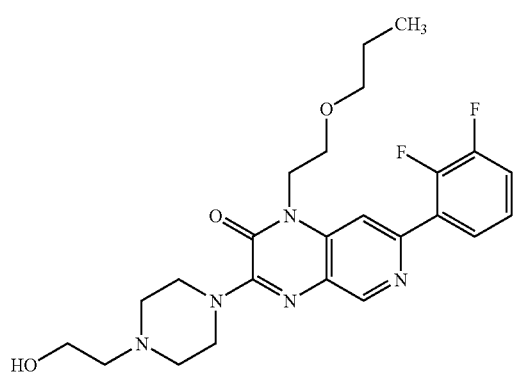

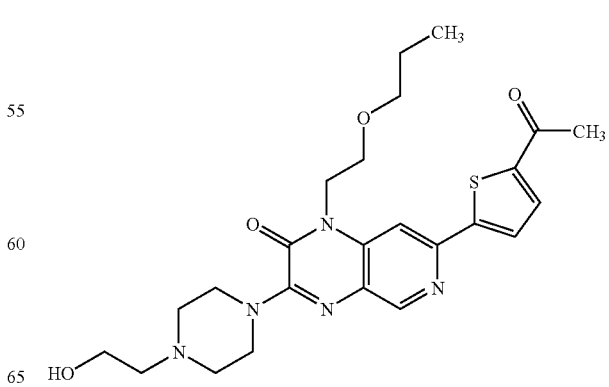

77

7-(5-acetylthiophen-2-yl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 5-acetylthiophen-2-yl-2-boronic acid in step 7. HRMS m/z 486.2128 (calcd for M+H, 486.2175).

Example 29

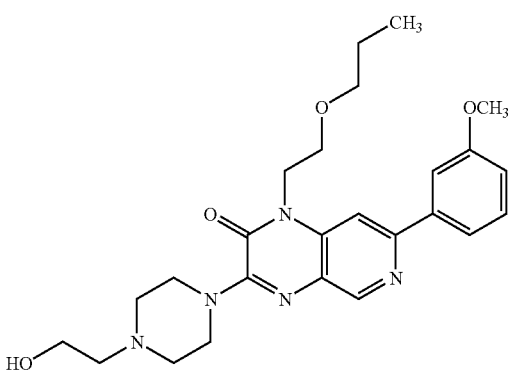

3-(4-(2-hydroxyethyl)piperazin-1-yl)-7-(3-methoxyphenyl)-1-(2-propoxyethyl)pyrido[3,4-b]pyrazin-2(1H)-one Prepared as in example 1 using 2-(piperazin-1-yl)ethanol in step 6 and 3-methoxyphenylboronic acid in step 7. HRMS m/z 468.2603 (calcd for M+H, 468.2611).

Example 30

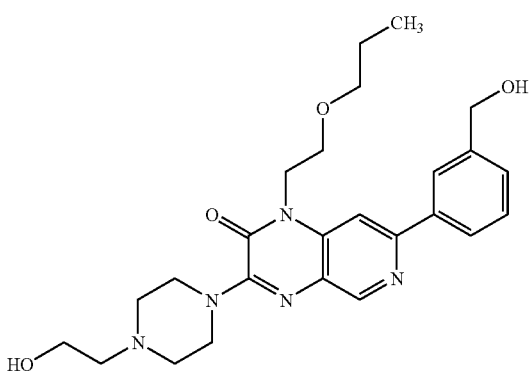

78

3-(4-(2-hydroxyethyl)piperazin-1-yl)-7-(3-(hydroxymethyl)phenyl)-1-(2-propoxyethyl)pyrido[3,4-b]pyrazin-2(1H)-one Prepared as in example 1 using 2-(piperazin-1-yl)ethanol in step 6 and 3-(hydroxymethyl)phenylboronic acid in step 7. HRMS m/z 468.2550 (calcd for M+H, 468.2611).

Example 31

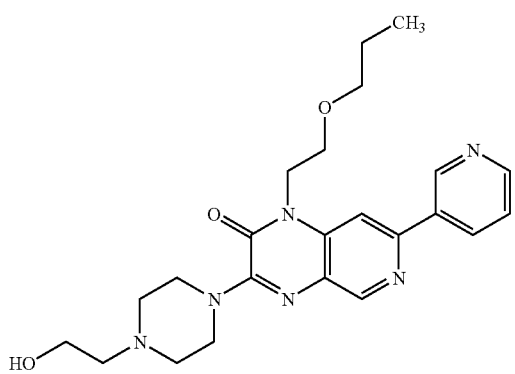

3-(4-(2-hydroxyethyl)piperazin-1-yl)-1-(2-propoxyethyl)-7-(pyridin-3-yl)pyrido[3,4-b]pyrazin-2(1H)-one Prepared as in example 1 using 2-(piperazin-1-yl)ethanol in step 6 and pyridin-3-yl-3-boronic acid in step 7. HRMS m/z 439.2361 (calcd for M+H, 439.2458).

Example 32

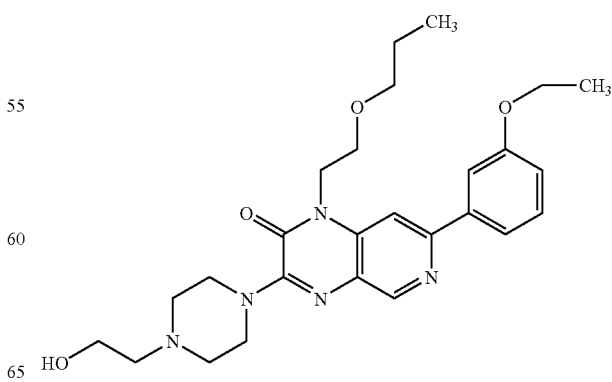

7-(3-ethoxyphenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 3-ethoxyphenylboronic acid in step 7. HRMS m/z 482.2743 (calcd for M+H, 482.2767).

Example 33

7-(5-chloro-2-fluorophenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 5-chloro-2-fluorophenylboronic acid in step 7. HRMS m/z 490.1991 (calcd for M+H, 490.2021).

Example 35

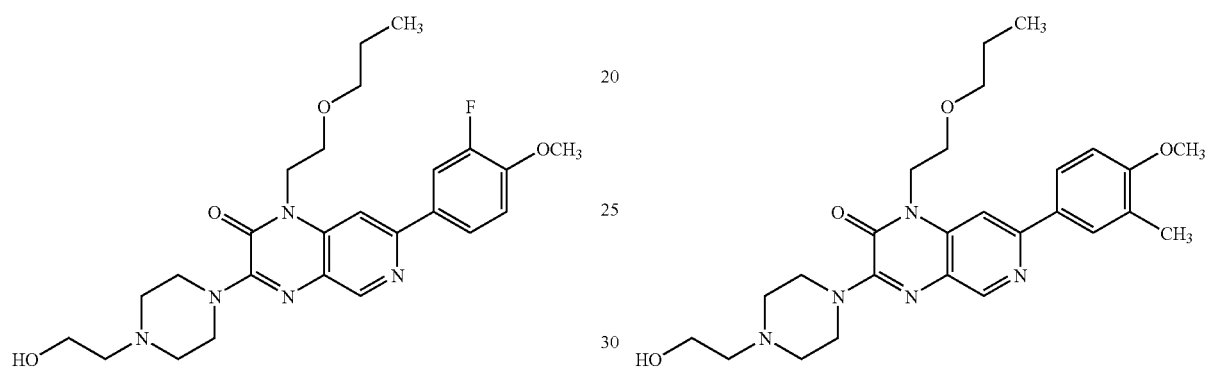

7-(3-fluoro-4-methoxyphenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 3-fluoro-4-methoxyphenylboronic acid in step 7. HRMS m/z 486.2608 (calcd for M+H, 486.2516).

Example 34

3-(4-(2-hydroxyethyl)piperazin-1-yl)-7-(4-methoxy-3-methylphenyl)-1-(2-propoxyethyl)pyrido[3,4-b]pyrazin-2(1H)-one Prepared as in example 1 using 2-(piperazin-1-yl)ethanol in step 6 and 4-methoxy-3-methylphenylboronic acid in step 7. HRMS m/z 482.2771 (calcd for M+H, 482.2767).

Example 36

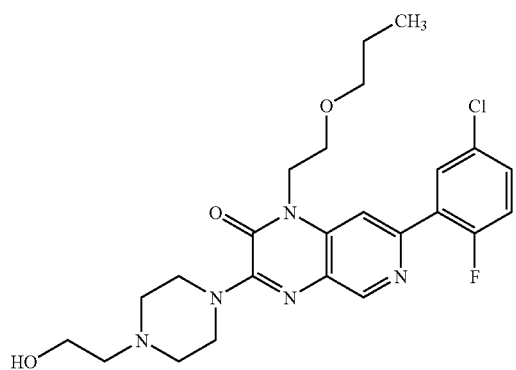

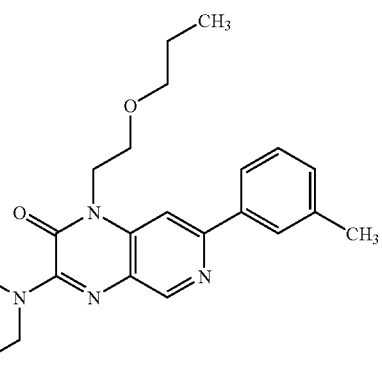

81

3-(4-(2-hydroxyethyl)piperazin-1-yl)-1-(2-propoxy-ethyl)-7-m-tolylpyrido[3,4-b]pyrazin-2(1H)-one Prepared as in example 1 using 2-(piperazin-1-yl)ethanol in step 6 and 3-methylphenylboronic acid in step 7. HRMS m/z 452.2672 (calcd for M+H, 452.2661).

Example 37

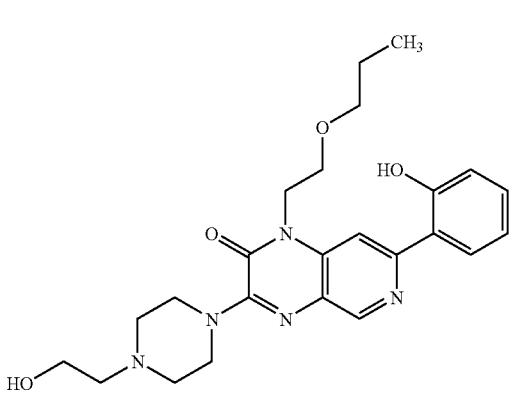

3-(4-(2-hydroxyethyl)piperazin-1-yl)-7-(2-hydroxyphenyl)-1-(2-propoxyethyl)pyrido[3,4-b]pyrazin-2(1H)-one Prepared as in example 1 using 2-(piperazin-1-yl)ethanol in step 6 and 2-hydroxyphenylboronic acid in step 7. HRMS m/z 454.2383 (calcd for M+H, 454.2383).

Example 38

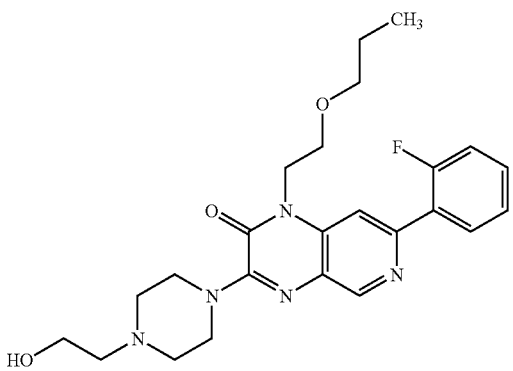

82

7-(2-fluorophenyl)-3-(4-(2-hydroxyethyl)piperazin-1-yl)-1-(2-propoxyethyl)pyrido[3,4-b]pyrazin-2(1H)-one Prepared as in example 1 using 2-(piperazin-1-yl)ethanol in step 6 and 2-fluorophenylboronic acid in step 7. HRMS m/z 456.2417 (calcd for M+H, 456.2411).

Example 39

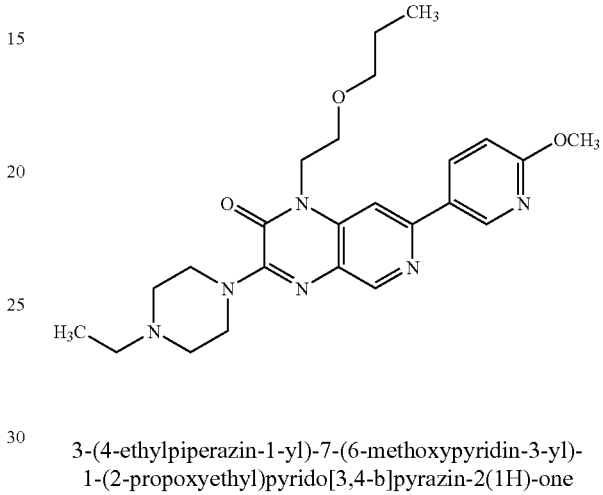

3-(4-ethylpiperazin-1-yl)-7-(6-methoxypyridin-3-yl)-1-(2-propoxyethyl)pyrido[3,4-b]pyrazin-2(1H)-one Prepared as in example 1 using 1-ethylpiperazine in step 6. LRMS m/z 453.3 (calcd for M+H, 453.5).

Example 40

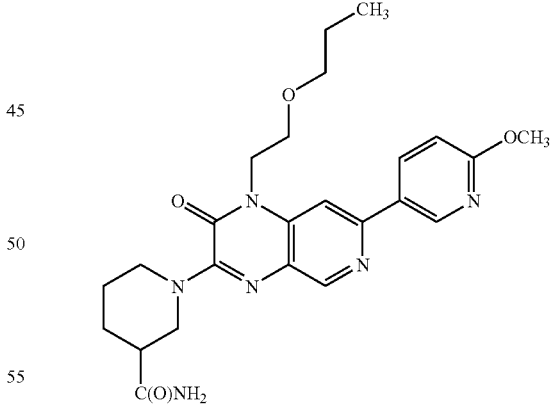

1-(1,2-dihydro-7-(6-methoxypyridin-3-yl)-2-oxo-1-(2-propoxyethyl)pyrido[3,4-b]pyrazin-3-yl)piperidine-3-carboxamide Prepared as in example 1 using piperidine-3-carboxamide in step 6. $^1$H NMR (CDCl$_3$) δ 8.82-8.78 (2H), 8.28-8.26 (1H), 7.69 (1H), 7.26 (1H), 6.88-6.85 (1H), 5.67 (1H), 4.52-4.40 (2H), 4.23-4.18 (1H), 4.02 (3H), 3.90-3.71 (4H), 3.44-3.37

(2H), 2.71-2.66 (1H), 2.31-2.25 (1H), 1.92-1.77 (3H), 1.60-0.45 (3H), 0.90-0.80 (3H); LRMS m/z 467.2 (calcd for M+H, 467.5).

Example 41

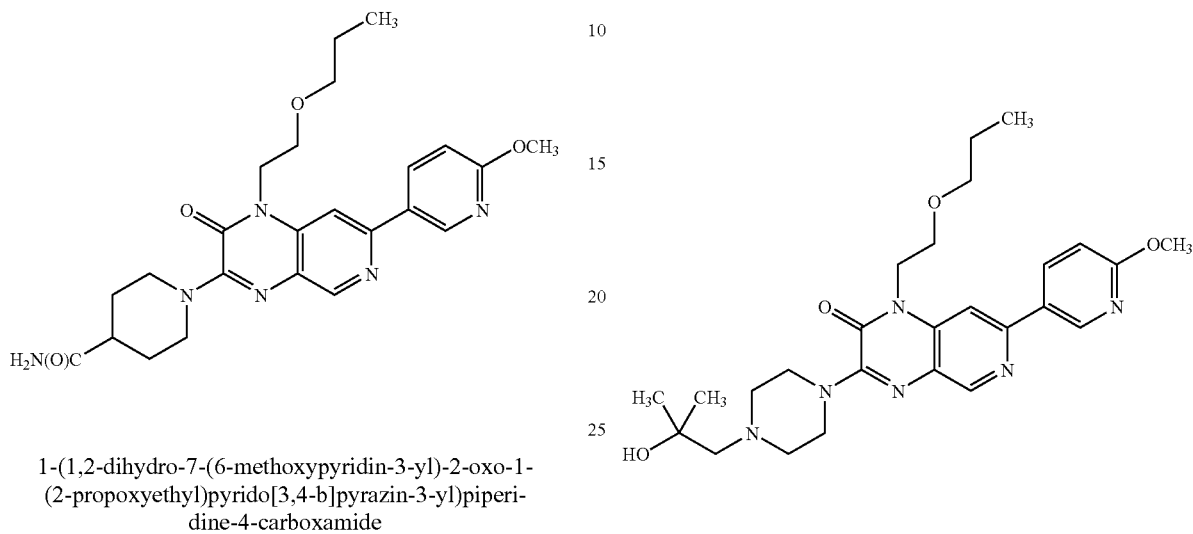

1-(1,2-dihydro-7-(6-methoxypyridin-3-yl)-2-oxo-1-(2-propoxyethyl)pyrido[3,4-b]pyrazin-3-yl)piperidine-4-carboxamide Prepared as in example 1 using piperidine-4-carboxamide in step 6. $^1$H NMR (CDCl$_3$) δ 8.78-8.74 (2H), 8.28-8.25 (1H), 7.66 (1H), 6.88-6.85 (1H), 5.58-5.53 (2H), 4.99-4.96 (2H), 4.46-4.28 (2H), 4.02 (3H), 3.84-3.79 (2H), 3.44-3.37 (2H), 3.13-3.07 (2H), 2.65 (1H), 2.06-1.86 (3H), 1.56-1.47 (3H), 0.90-0.82 (3H); LRMS m/z 467.2 (calcd for M+H, 467.5).

Example 42

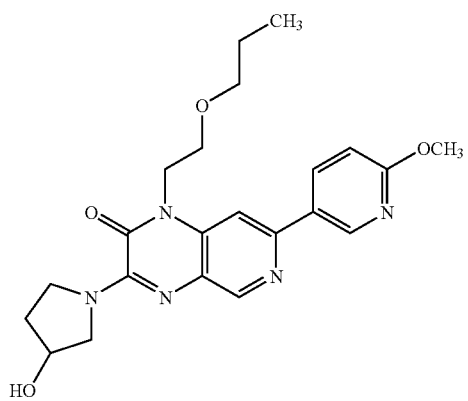

3-(3-hydroxypyrrolidin-1-yl)-7-(6-methoxypyridin-3-yl)-1-(2-Propoxyethyl)pyrido[3,4-b]pyrazin-2(1H)-one Prepared as in example 1 using pyrrolidin-3-ol in step 6. $^1$H NMR (CDCl$_3$) δ 8.74-8.71 (2H), 8.26-8.23 (1H), 7.61 (1H), 6.86-6.84 (1H), 4.73 (1H), 4.43-4.01 (9H), 3.79-3.76 (2H), 3.40-3.37 (2H), 2.08 (3H), 1.57-1.39 (2H), 0.90-0.82 (3H); LRMS m/z 426.2 (calcd for M+H, 426.5).

Example 43

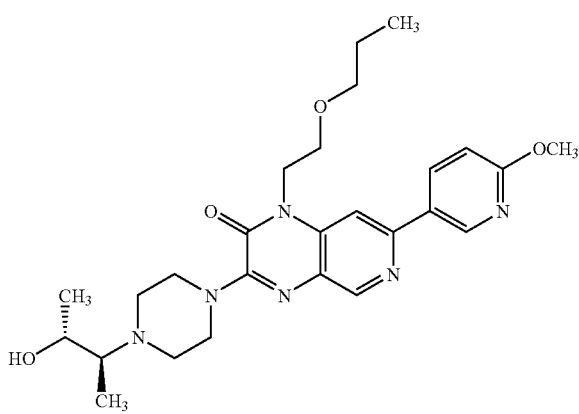

3-(4-(2-hydroxy-2-methylpropyl)piperazin-1-yl)-7-(6-methoxypyridin-3-yl)-1-(2-propoxyethyl)pyrido[3,4-b]pyrazin-2(1H)-one Prepared as in example 1 using 2-methyl-1-(piperazin-1-yl)propan-2-ol in step 6. $^1$H NMR (CDCl$_3$) δ 8.75 (2H), 8.24-8.22 (1H), 7.61 (1H), 6.84-6.82 (1H), 4.42-4.39 (2H), 3.99 (7H), 3.81-3.76 (2H), 3.38 (2H), 3.10-3.00 (1H), 2.81-2.78 (4H), 2.39 (2H), 1.53-1.46 (2H), 1.25 (6H), 0.81-0.75 (3H); LRMS m/z 497.4 (calcd for M+H, 497.6).

Example 44

3-(4-((2S,3R)-3-hydroxybutan-2-yl)piperazin-1-yl)-7-(6-methoxypyridin-3-yl)-1-(2-propoxyethyl)pyrido[3,4-b]pyrazin-2(1H)-one Prepared as in example 1 using (2R,3S)-3-(piperazin-1-yl)butan-2-ol in step 6. HRMS m/z 497.4 (calcd for M+H, 497.6).

Example 45

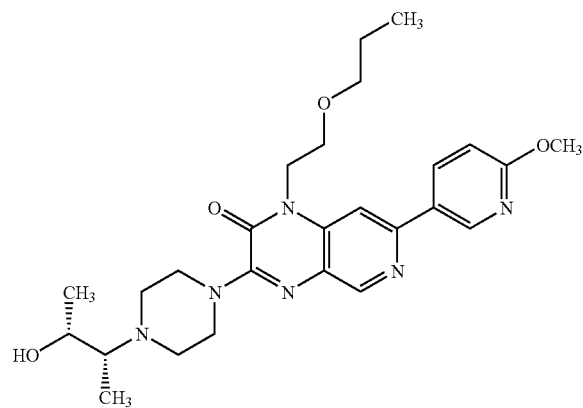

3-(4-((2R,3R)-3-hydroxybutan-2-yl)piperazin-1-yl)-7-(6-methoxypyridin-3-yl)-1-(2-propoxyethyl)pyrido[3,4-b]pyrazin-2(1H)-one Prepared as in example 1 using (2R,3R)-3-(piperazin-1-yl)butan-2-ol in step 6. HRMS m/z 497.4 (calcd for M+H, 497.6).

Example 46

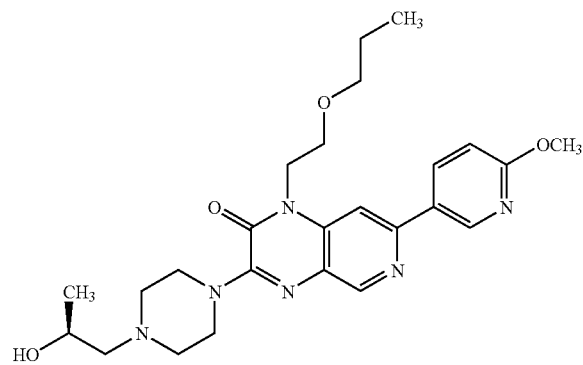

3-(4-((S)-2-hydroxypropyl)piperazin-1-yl)-7-(6-methoxypyridin-3-yl)-1-(2-propoxyethyl)pyrido[3,4-b]pyrazin-2(1H)-one Prepared as in example 1 using (S)-1-(piperazin-1-yl)propan-2-ol in step 6. $^1$H NMR (CDCl$_3$) δ 8.76 (2H), 8.25 (1H), 7.62 (1H), 6.85-6.82 (1H), 4.71 (2H), 4.43-3.91 (7H), 3.80-3.74 (2H), 3.38-3.35 (2H), 2.83-2.80 (2H), 2.57-2.54 (2H), 2.38-2.29 (2H), 1.54-1.45 (2H), 1.32-1.25 (5H), 0.96-0.79 (3H); HRMS m/z 483.3 (calcd for M+H, 483.6).

Example 47

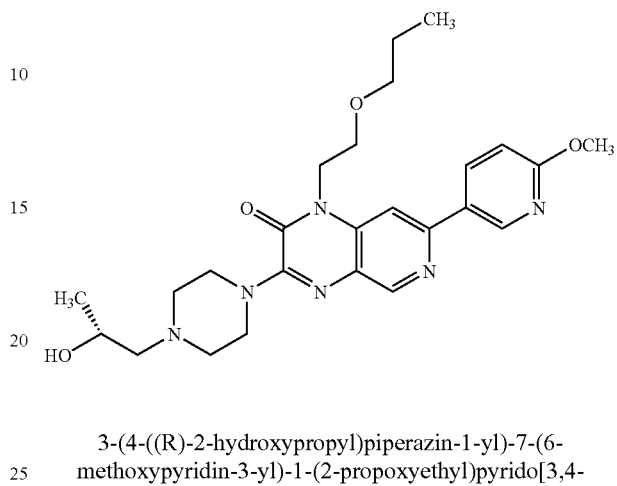

3-(4-((R)-2-hydroxypropyl)piperazin-1-yl)-7-(6-methoxypyridin-3-yl)-1-(2-propoxyethyl)pyrido[3,4-b]pyrazin-2(1H)-one Prepared as in example 1 using (R)-1-(piperazin-1-yl)propan-2-ol in step 6. HRMS m/z 483.3 (calcd for M+H, 483.6).

Example 48

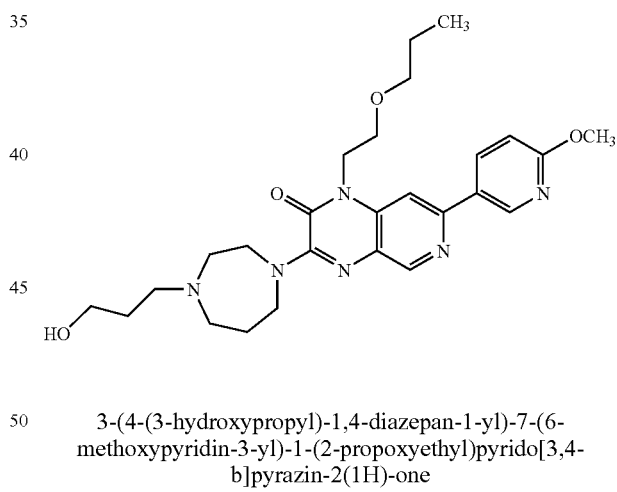

3-(4-(3-hydroxypropyl)-1,4-diazepan-1-yl)-7-(6-methoxypyridin-3-yl)-1-(2-propoxyethyl)pyrido[3,4-b]pyrazin-2(1H)-one Prepared as in example 1 using 3-(1,4-diazepan-1-yl)propan-1-ol in step 6. HRMS m/z 497.4 (calcd for M+H, 497.6).

O. In Vitro Assays

Method 1: Human Platelet PDE5 Enzyme Inhibition Scintillation Proximity Assay

The IC$_{50}$ of a test compound can be measured using an in vitro assay using PDE5 enzyme isolated from human platelets. The IC$_{50}$ is the concentration of test compound required to inhibit the hydrolysis of cGMP to GMP by the PDE5 enzyme by 50% relative to the activity of uninhibited controls. The PDE5 enzyme for use in the assay can be obtained from human platelets by appropriate modification of the method of Thompson, W J et al.; Biochemistry 18(23), 5228-5237, 1979, as described by Ballard S A et al.; J. Urology 159(6), 2164-2171, 1998. The PDE5 enzyme so obtained can be used to catalyze the hydrolysis of [$^3$H]cGMP (Amersham Biosciences) to 5' nucleotide [$^3$H]GMP. The [$^3$H]GMP binds to yttrium silicate SPA beads (Amersham Biosciences) and is detected by scintillation counting. More specifically, the effect of a test compound at different concentrations can be evaluated in the assay by contacting the compound with a fixed amount of PDE5 enzyme in the presence of substrate (cGMP or cAMP in a 3:1 ratio unlabelled to [$^3$H]-labeled). Scintillation counting can be used as described above to determine relative PDE5 enzyme activity. The inhibition of PDE5 enzyme activity is then calculated relative to total PDE5 enzyme activity of uninhibited controls.

PDE5 IC$_{50}$ Assay: 96-Well Microtiter Plate Format

Reagents

Buffer A: 20 mM Tris-HCl, 5 mM MgCl$_2$, pH 7.4
Buffer B: 2 mg/ml BSA in Buffer A (enzyme buffer)
cGMP substrate: Final concentration of 500 nM in assay
The amount of $^3$H-labeled substrate added depends upon the specific activity of [$^3$H]cGMP, and the cGMP substrate is diluted with a 10 mM stock of cold cGMP in Buffer A for a final substrate concentration of 500 nM in the assay.
PDE enzyme: Prepared in Buffer B. The dilution factor is determined by enzyme activity.
SPA beads: 20 mg/ml suspension prepared in dH2O.

| Positive Control | Negative Control | Standard/Test compound |
|---|---|---|
| 2 µl 100% DMSO | 2 µl 100% DMSO | 2 µl Standard/Test compound |
| 25 µl Buffer A | 25 µl Buffer A | 25 µl Buffer A |
| 25 µl Enzyme | 25 µl Buffer B | 25 µl Enzyme |
| 50 µl Substrate | 50 µl Substrate | 50 µl Substrate |
| 50 µl SPA to stop | 50 µl SPA to stop | 50 µl SPA to stop |

Stocks of standard and test compounds are prepared at 5 mM in 100% DMSO. The compound is serially diluted in a dilution plate using a 10-point ½ log dilution format. 2 µl of the compound dilution is added in duplicate to the wells of the assay plate. 2 µl of 100% DMSO are added to designated control wells. 25 µl of Buffer A are added to all wells. 25 µl of Buffer B are added to the negative control wells. 25 µl of enzyme are added to the remaining wells. 50 µl of substrate are added to each well. Plates are sealed and incubated for 60 minutes on a plate shaker at 30 C. 50 µl of SPA beads are added to stop the reaction. The plates are again sealed and shaken for 15 minutes to allow the beads to bind the GMP product. The beads are allowed to settle for 30 minutes and then read on a NXT TopCount scintillation counter. Data are analyzed with a curve fitting application for plate-based screening. Percent inhibition in this assay is calculated as follows:

Inhibition (%)=[(mean maximum−compound value/
(mean maximum−mean minimum)]×100.

The IC$_{50}$ value is determined from sigmoid dose-response curves of enzyme activity versus compound concentration.

Method 2: Alternative Human Platelet PDE5 Enzyme Inhibition Scintillation Proximity Assay The IC$_{50}$ of a test compound also can be measured in an alternative in vitro assay that varies from Method 1 as described below:

PDE5 IC$_{50}$ Assay: 96-Well Microtiter Plate Format

Reagents

Buffer A: 20 mM Tris-HCl, 5 mM MgCl$_2$, pH 7.4
Buffer B: 2 mg/ml BSA in Buffer A (enzyme buffer)
cGMP substrate: Final concentration of 50 nM in assay
The amount of $^3$H-labeled substrate added depends upon the specific activity of [$^3$H]cGMP, and it is diluted in Buffer A.
PDE enzyme: Prepared in Buffer B. The dilution factor is determined by enzyme activity.
SPA beads: 4 mg/ml suspension prepared in dH$_2$O.

| Positive Control | Negative Control | Standard/Test compound |
|---|---|---|
| 3 µl 100% DMSO | 3 µl 100% DMSO | 3 µl Standard/Test compound |
| 27 µl Buffer A | 27 µl Buffer A | 27 µl Buffer A |
| 30 µl Enzyme | 30 µl Buffer B | 30 µl Enzyme |
| 30 µl Substrate | 30 µl Substrate | 30 µl Substrate |
| 30 µl SPA to stop | 30 µl SPA to stop | 30 µl SPA to stop |

Stocks of standard and test compound are prepared at 2 mM in 100% DMSO. The test compound is serially diluted in a dilution plate using an 8-point ⅓ log dilution format such that the starting concentration in the assay is 2 µM for an initial IC$_{50}$ screen. 27 µl of Buffer A are added to the wells of the assay plates. From the dilution plate, 3 µl of diluted compound is delivered in duplicate or 3 µl of 100% DMSO (for positive and negative controls) are added. 30 µl of enzyme are added. For the negative control wells, Buffer B is substituted in place of the enzyme. 30 µl of labeled substrate are added to all wells.

After incubating for 60 minutes at room temperature, the reaction is stopped with the addition of 30 µl of the yttrium silicate beads. These beads are dense and require constant agitation while being added to the plate. The plates are sealed and shaken on a plate shaker for fifteen minutes to allow the beads to bind the GMP product.

After allowing the beads to settle for 30 minutes, plates are read on a NXT TopCount scintillation counter and the data are analyzed as follows. Percent inhibition values are calculated using the means of the 0% and 100% controls on each plate. The estimates of the 4-parameters of the logistic, sigmoid dose-response model are then calculated using the well-level percent inhibition value for the compound. The formula for the four-parameter logistic model may be expressed as $Y=((a-d)/(1+(X/c)^b))+d$, where Y is the response, X is the concentration, a is the lower asymptote (minimum response), d is the upper asymptote (maximum response), c is the model IC$_{50}$ (in the same units as X), and b is the slope (as described in De Lean, A., P. J. Munson, and D. Rodbard ("Simultaneous analysis of families of sigmoidal curves: application to bioassay, radioligand assay, and physiological dose-response curves." Am. J. Physiol. 235(2): E97-E102, 1978). These estimates are used to calculate the concentration that corresponds to 50% inhibition.

Compounds were tested in accordance with Method 2 above yielding the IC$_{50}$ values described in Table C.

TABLE C

| Example # | PDE5 IC50 (nM) |
|---|---|
| 1 | 3.28 |
| 2 | 2.38 |
| 3 | 1.01 |

TABLE C-continued

| Example # | PDE5 IC50 (nM) |
|---|---|
| 4 | 0.225 |
| 5 | 0.203 |
| 6 | 0.313 |
| 7 | 0.083 |
| 8 | 0.517 |
| 9 | 0.248 |
| 10 | 0.193 |
| 11 | 0.177 |
| 12 | 0.721 |
| 13 | 1.35 |
| 14 | 832 |
| 15 | 1190 |
| 16 | 3.34 |
| 17 | 7.71 |
| 18 | 29.9 |
| 19 | 102 |
| 20 | 1.59 |
| 21 | 413 |
| 22 | >2000 |
| 23 | 1790 |
| 24 | 1400 |
| 25 | 1.87 |
| 26 | 47.1 |
| 27 | 9.31 |
| 28 | 43.1 |
| 29 | 3.07 |
| 30 | 311 |
| 31 | 45.8 |
| 32 | 158 |
| 33 | 13.6 |
| 34 | 12.6 |
| 35 | 1.69 |
| 36 | 423 |
| 37 | 18.1 |
| 38 | 42.2 |
| 39 | 0.217 |
| 40 | 0.296 |
| 41 | 0.249 |
| 42 | 0.421 |
| 43 | 0.208 |
| 44 | 0.33 |
| 45 | 0.295 |
| 46 | 0.306 |
| 47 | 0.226 |
| 48 | 1.07 |

P. Ex Vivo Assays

Method 3: Aortic Ring Assay

A test compound can be tested in an ex vivo assay that measures the direct relaxation of rat aortic rings exposed to the compound. In this assay, a test compound elicits a relaxation of an aortic ring by enhancing the cGMP signal evoked by a stable exogenous nitric oxide donor, diethyltriamine NONOate (diazen-1-ium-1,2-diolate) ("DETA-NO"). An $EC_{50}$, with 95% confidence intervals, for compound-evoked relaxation is calculated as an index of potency. The $EC_{50}$ is the concentration of a test compound which produces 50% of the maximum possible effective response for a test compound.

Male ague-Dawley rats (250-350 g) are asphyxiated using $CO_2$ gas and their thoracic aortas carefully excised and placed in Krebs buffer. The aortas are then carefully dissected free of connective tissue and divided into 8 sections, each 3-4 mm in length.

Aortic rings are suspended between parallel stainless steel wires in a water jacketed (37° C.), 15 mL tissue bath under a resting tension of 1 gram. Tension is measured using isometric tension transducers and recorded using Ponemah tissue platform system. Each preparation is allowed to equilibrate for at least 60 minutes prior to compound testing. During this time, the tissues are also incubated with 200 uM NG-monomethyl L-arginine ("L-NMMA"), and the incubation media changed every 15 to 20 minutes (L-NMMA is added after each wash to maintain the final concentration at 200 uM in each tissue bath).

Following the equilibration period, baseline tensions are recorded for each tissue. The vasoconstrictor response to phenylepherine (1 uM) is assessed and when the response to phenylepherine reaches a maximum, vascular reactivity is subsequently assessed by a challenge of acetylcholine (1 uM). Following another washout period, a second baseline value is recorded after adding the vasoconstrictor noradrenaline (25 nM) to each bath and incubating the tissues for a time period (about 15 minutes) sufficient for the tissues to achieve a stable tone. An exogenous nitric oxide drive is supplied using the stable nitric oxide donor, DETA-NO. The concentration of DETA-NO is titrated (cumulatively in half-log increments) to achieve approximately 5 to 15% relaxation of the noradrenaline-evoked preconstriction. Cumulative concentration-response curves are constructed in a single ring, typically using 5 doses/ring and allowing 15 minutes between each addition.

Method 4: Alternative Aortic Ring Assay

Method 3 can be modified to provide an alternative protocol for to measuring the direct relaxation of rat aortic rings exposed to a test compound. This alternative method varies from Method 3 as described below:

For the alternative method, the endothelium is first removed by gently rubbing the lumen of the vessel together between the fingers prior to preparing the rings (denuded rings). The resting tension is set at 2 grams and the vasoconstrictor response to a maximal concentration of phenylephrine (1 μM) is assessed, followed (after a washout period) by two further exposures to 300 nM of phenylephrine. The concentration-response relationship to noradrenaline is constructed in each tissue over concentration range 0.1 to 300 nM. After another washout period, the tissues are constricted with an $EC_{90}$ concentration of noradrenaline for compound testing.

Q. Biological Protocols—In Vivo Assays

Method 5: Culex™ Assay

The effect of a test compound on systemic arterial blood pressure can be evaluated in a conscious pre-cannulated spontaneously hypertensive rat ("SHR") model. This assay is conducted using an automated blood sampler ("ABS") system. The Culex™ ABS system (Bioanalytical System, Inc., West Lafayette, Ind.) comprises a laptop computer, four control units and metabolic cages. This ABS system allows for the collection of multiple blood samples from a single rat without causing undue stress to the animal. In addition, the ABS system allows for the collection of urine samples that can be potentially used for biomarker identifications. Through this approach, efficacy and standard pharmacokinetic studies are conducted in the conscious unrestrained SHR rats simultaneously to define the relationship between plasma free drug concentration or potential biomarker(s) and pharmacological effect (reduction of mean arterial blood pressure).

SHR rats at 12 to 16 weeks of age, weighing about 300 g, undergo surgical cannulation of both jugular veins and the right carotid artery. After surgical recovery, animals are placed in the Culex™ cages and tethered to a movement-responsive arm with a sensor that controls cage movement when the animal moves to prevent the catheters from being twisted. Connections are made between the right jugular catheter and the Culex™ sterile tubing set for blood sampling, and the left jugular catheter for compound administration, and the catheter in the right carotid artery is connected to a pressure transducer for monitoring blood pressure. To keep the patency of the catheters, the right jugular cannula is maintained by the "tend" function of the Culex™ that flushes the catheter with 20 μL heparin saline (10 units/mL) every 12 minutes or between sampling events, and the left jugular cannula is filled with heparin saline (20 units/mL). The patency of the right carotid cannula is maintained by slow infusion of heparin saline either directly into the extend tubing when blood pressure is not recorded or through the pressure transducer during the blood pressure monitoring. Animals are allowed to acclimate for at least two hours before compound evaluation. A test compound may be administered intravenously or by oral gavage. Blood sampling protocols (sampling time and volume) are programmed using the Culex™ software. The total amount of blood withdrawn from each animal will not exceed 750 μL/24 hrs and 10 mL/kg within two weeks. Heart rate, blood pressure, and drug concentration are monitored. Systemic arterial blood pressure and heart rate are recorded by PONEMAH (Gould Instrument System, Valley View, Ohio), a pressure transducer through a data acquisition system for recording blood pressure and heart rate, for 6 to 24 hours based on experimental protocol. Mean arterial blood pressure (primary endpoint) is analyzed for assessing the efficacy of the compound.

Blood samples are analyzed for measuring plasma drug concentration, using the LC/MS/MS method described below, and for evaluating potential biomarkers.

LC/MS/MS Method

Sample Preparation: Plasma samples (50 μL unknown, control or blank) are mixed with 10 μL acetonitrile:water or a standard solution of a test compound and 150 μL of internal standard solution (100 ng/mL of a test compound in acetonitrile). The mixture is centrifuged at 3000 rpm for 5 min, and 125 μL of the supernatant transferred to a 96 well plate. The solvent is evaporated under a stream of nitrogen and the residue is reconstituted with 80 μL acetonitrile/0.1% aqueous formic acid (20:80 v/v).

A 20 μL volume of each prepared sample is injected onto a Phenomenex Synergi 4 μm MAX-RP 2.0×75 mm column and eluted at 0.4 mL/min using gradient elution from 0.1% aqueous formic acid (mobile phase A) to acetonitrile (mobile phase B). The gradient program consists of initial gradient of 90% mobile phase A, followed by a linear gradient to 75% mobile phase B from 0.2 to 1.15 min after injection and held at 75% mobile phase B until 2.0 min. The mobile phase was linearly changed back to 90% mobile phase A from 2.00 to 2.10 minutes, and the next injection took place at 3.00 min. Detection was performed by mass spectrometry using positive ion electrospray (ESI) with multiple reaction monitoring of the transitions m/z 454.00 (MH+a test compound)→m/z 408.00, m/z 466.24 (MH+a test compound)→409.33. The ion spray voltagea is set at 5000. A calibration curve is constructed by using peak area ratios of the analyte relative to the internal standard. Subject concentrations are determined by inverse prediction from their peak area ratios against the calibration curve.

Method 6: Implantation of Radio Transmitters and Subsequent Blood Pressure Screening by Telemetry in Spontaneously Hypertensive Rats SHR Rats are anesthetized with isoflurane gas via an isoflurane anesthesia machine that is calibrated to deliver isoflurane over a range of percentages as oxygen passes through the machine's inner chambers. The animals are placed in an induction chamber and administered isoflurane at 4-5% to reach a surgical plane of anesthesia. They are then maintained at 1-2% during the surgical procedure via a nose cone, with isoflurane delivered via a smaller isoflurane anesthesia device on the surgical table.

Following administration of anesthesia, the rats are implanted with transmitters using aseptic procedures with commercially available sterile radio-telemetry units (Data Sciences, International, Roseville, Minn. 55113-1136). Prior to surgery the surgical field is shaved, scrubbed with Dial™ brand antimicrobial solution (containing 4% chlorhexidine gluconate and 4% isopropyl alcohol) followed by an application of iodine (10%) spray solution. A 2.5 to 3.0 cm laparotomy is preformed and the radio-telemetry units implanted into the abdomen, with the catheter tip inserted into the abdominal aorta. Baby Weitlaner retractors are used to retain soft tissue. A 1 cm section of the abdominal aorta is partially dissected and that section cross-clamped briefly, punctured with a 21-gauge needle and the transmitter catheter tip introduced into the vessel and secured by a single 4.0 silk suture anchored to the adjacent psoas muscle. The transmitter body is then inserted into the abdominal cavity and simultaneously secured to the abdominal muscle wall while closing with running 4.0 silk suture. The skin layer is closed with subdermal continuous 4.0 absorbable suture. A subcutaneous (s.c.) administration of marcaine followed by a topical application of iodine is administered into and around the suture line, respectively, upon closing. All rats receive a postoperative injection of buprenorphine @ 0.05 mg/kg, s.c. before regaining consciousness. A typical dose volume for a 0.300 kg rat will be 0.050 ml. The rats must be fully recovered from their operative anesthesia before the administration of buprenorphine. They then receive the same dose once daily for 2 consecutive days, unless the animal demonstrates that it is in compromising postoperative pain.

Following surgery, the rats are returned to their cages and housed individually on solid bottom caging with paper bedding. A period of no less than 7 days is allowed for recovery before experimental procedures are initiated. It has been observed that the rats are typically hypertensive for several days following surgery and return to "normotensive" levels by approximately the $7^{th}$ day post-surgery. They are fed standard rat chow and water ad libitum throughout the experimental time line.

Test compounds are administered intragastrically (i.g.) via gavage, using of a stainless steel, 2½ inch, 18 gauge gavage needle with a balled end. For single daily dosing, the target volume is 3.33 ml/kg, i.g. The dose volume for a test compound is approximately 1 ml/rat. The vehicles in which a test compound is administered is methylcellulose (0.5%)+Tween 80 (0.1%) in 50 mM citrate buffer pH=5.0.

Blood pressure data will be obtained using Data Sciences International's data acquisition program (Version 3.0). Blood pressure samples are recorded at 1.5-3 minute intervals for a 5 second duration 24 hours per day for the entire study. This data is processed by Data Science's data analysis software into averages of a desired time intervals. All other data reduction is performed in Microsoft Excel™ spreadsheets.

All documents mentioned in this application are expressly incorporated by reference as if fully set forth at length. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

We claim:
1. A compound, or a pharmaceutically acceptable salt thereof, wherein the compound has the structure of Formula I:

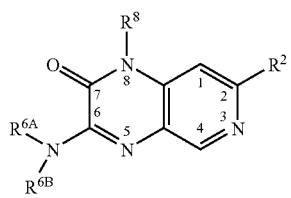

and wherein:
$R^2$ is selected from the group consisting of phenyl, thienyl and pyridinyl, wherein said $R^2$ substituents may be optionally substituted with one or more substituents independently selected from the group consisting of halogen, cyano, nitro, oxo, alkyl, alkenyl, alkynyl, cycloalkyl, —$OR^{201}$, —$C(O)R^{201}$, —$OC(O)R^{201}$, —$C(O)OR^{201}$, —$NR^{201}R^{202}$, —$N(R^{202})C(O)R^{202}$, —$C(O)NR^{201}R^{202}$, —$C(O)NR^{201}C(O)R^{202}$, —$SR^{201}$, —$S(O)R^{201}$, and —$S(O)_2R^{201}$; wherein said alkyl, alkenyl, alkynyl, and cycloalkyl substituents may be optionally substituted with one or more substituents independently selected from the group consisting of halogen, oxo, —$OR^{203}$, and —$C(O)OR^{203}$;

$R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy, alkoxy, carboxy and —$C(O)NH_2$;

$R^{6A}$ and $R^{6B}$ together with the nitrogen to which they are attached form a piperazinyl ring, wherein the piperazinyl ring may be optionally substituted with one or more substituents independently selected from the group consisting of hydrogen, halogen, oxo, alkyl, alkenyl, alkynyl, cyano, cycloalkyl, aryl, heterocyclyl, —$OR^{601}$, —$C(O)R^{601}$, —$OC(O)R^{601}$, —$C(O)OR^{601}$, —$NR^{601}R^{602}$, —$N(R^{601})C(O)R^{602}$, —$C(O)NR^{601}R^{602}$, and —$C(O)NR^{601}C(O)R^{602}$, wherein (a) said alkyl, alkenyl, alkynyl and cycloalkyl substituents may be optionally substituted with one or more substituents independently selected from the group consisting of halogen, cyano, oxo, —$OR^{603}$, —$C(O)R^{603}$, —$C(O)OR^{603}$, —$OC(O)R^{603}$, —$NR^{603}R^{604}$, —$N(R^{603})C(O)R^{604}$, —$C(O)NR^{603}R^{604}$, —$C(O)NR^{603}C(O)R^{604}$, —$SR^{603}$, —$S(O)R^{603}$, —$S(O)_2R^{603}$, —$N(R^{603})S(O)_2R^{604}$, and —$S(O)_2NR^{603}R^{604}$, $C(O)NR^{603}C(O)R^{604}$, —$SR^{603}$, —$S(O)R^{603}$, —$S(O)_2R^{603}$, —$N(R^{603})S(O)_2R^{604}$, and —$S(O)_2NR^{603}R^{604}$, and (b) said aryl and heterocyclyl substituents may be optionally substituted with one or more substituents independently selected from the group consisting of halogen, alkyl, alkenyl, alkynyl, cyano, oxo, —$OR^{601}$, —$C(O)R^{601}$, —$C(O)OR^{601}$, —$OC(O)R^{601}$, —$NR^{601}R^{602}$, —$N(R^{601})C(O)R^{602}$, —$C(O)NR^{601}R^{602}$, —$C(O)NR^{601}C(O)R^{602}$, —$SR^{601}$, —$S(O)R^{602}$, —$S(O)_2R^{602}$, —$N(R^{601})S(O)_2R^{602}$, and —$S(O)_2NR^{601}R^{602}$;

$R^{601}$, $R^{602}$, $R^{603}$ and $R^{604}$ are independently selected from the group consisting of hydrogen, alkyl, alkenyl, and alkynyl, wherein (a) said $R^{601}$ and $R^{602}$ alkyl may be optionally substituted with one or more substituents independently selected from the group consisting of halogen, cyano, hydroxy, carboxy, oxo, alkenyl, alkynyl, haloalkenyl, hydroxyalkenyl, carboxyalkenyl, haloalkynyl, hydroxyalkynyl, carboxyalkynyl, alkoxy, haloalkoxy, hydroxyalkoxy, and carboxyalkoxy, and (b) said $R^{601}$ and $R^{602}$ alkenyl and alkynyl substituents may be optionally substituted with one or more substituents independently selected from the group consisting of halogen, cyano, hydroxy, carboxy, oxo, alkoxy, haloalkoxy, hydroxyalkoxy, and carboxyalkoxy;

$R^8$ is alkyl; wherein said $R^8$ substituent may be optionally substituted with one or more substituents independently selected from the group consisting of halogen, cyano, hydroxy, carboxy, alkenyl, alkynyl, —$OR^{801}$, —$C(O)R^{801}$, —$C(O)OR^{801}$, —$OC(O)R^{801}$, —$NR^{801}R^{802}$, —$N(R^{801})C(O)R^{802}$, —$C(O)NR^{801}R^{802}$, and —$C(O)NR^{801}C(O)R^{802}$, wherein said alkenyl and alkynyl substituents may be optionally substituted with one or more substituents independently selected from the group consisting of halogen, cyano, hydroxy, carboxy, oxo, and alkoxy; and $R^{801}$ and $R^{802}$ are independently selected from the group consisting of hydrogen, alkyl, alkenyl and alkynyl, wherein (a) when said alkyl is methyl, said methyl may be optionally substituted with 1, 2, or 3 fluoro substituents, (b) when said alkyl comprises at least two carbon atoms, said alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy, and (c) said $R^{801}$ and $R^{802}$ alkenyl and alkynyl substituents may be optionally substituted with one or more substituents independently selected from the group consisting of halogen, cyano, hydroxy, carboxy, oxo, alkoxy, haloalkoxy, hydroxyalkoxy, and carboxyalkoxy.

2. The compound of claim 1 wherein $R^8$ is alkyl substituted with —$OR^{801}$.

3. The compound of claim 1 wherein $R^2$ is selected from the group consisting of phenyl and thienyl, wherein the $R^2$ phenyl and thienyl may be optionally substituted with one or more substituents independently selected from the group consisting of halogen, cyano, nitro, oxo, alkyl, alkenyl, alkynyl, cycloalkyl, —$OR^{201}$, —$C(O)R^{201}$, —$OC(O)R^{201}$, —$C(O)OR^{201}$, —$NR^{201}R^{202}$, —$N(R^{202})C(O)R^{202}$, —$C(O)NR^{201}R^{202}$, —$C(O)NR^{201}C(O)R^{202}$, —$SR^{201}$, —$S(O)R^{201}$, and —$S(O)R^{201}$; wherein said alkyl, alkenyl, alkynyl, and cycloalkyl substituents may be optionally substituted with one or more substituents independently selected from the group consisting of halogen, oxo, —$OR^{203}$, and —$C(O)OR^{203}$;

$R^{201}$, $R^{202}$ and $R^{203}$ are independently selected from the group consisting of hydrogen and alkyl, wherein said alkyl may be optionally substituted with one or more substituents independently selected from the group consisting of halogen, hydroxy, alkoxy, carboxy and —$C(O)NH_2$.

4. A compound of claim 1 wherein:
$R^2$ is selected from the group consisting of phenyl and thienyl, wherein the $R^2$ phenyl and thienyl may be optionally substituted with one or more substituents independently selected from the group consisting of halogen, cyano, nitro, oxo, alkyl, alkenyl, alkynyl, cycloalkyl, —$OR^{201}$, —$C(O)R^{201}$, —$OC(O)R^{201}$, —$C(O)OR^{201}$, —$NR^{201}R^{202}$, —$N(R^{202})C(O)R^{202}$, —$C(O)NR^{201}R^{202}$, —$C(O)NR^{201}C(O)R^{202}$, —$SR^{201}$, —S(O)R$^{201}$, and —S(O)$_2$R$^{201}$; wherein said alkyl, alkenyl, alkynyl, and cycloalkyl substituents may be optionally substituted with one or more substituents independently selected from the group consisting of halogen, oxo, —OR$^{203}$, and —C(O)OR$^{203}$;

R$^{201}$, R$^{202}$ and R$^{203}$ are independently selected from the group consisting of hydrogen and alkyl, wherein said alkyl may be optionally substituted with one or more substituents independently selected from the group consisting of halogen, hydroxy, alkoxy, carboxy and —C(O)NH$_2$; and R$^8$ is alkyl substituted with —OR$^{801}$.

5. A compound, or a pharmaceutically acceptable salt thereof, wherein the compound has the structure of Formula I:

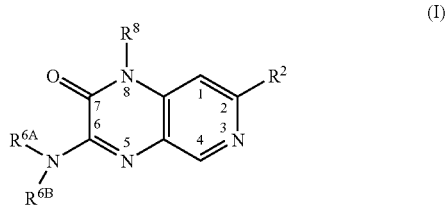

and wherein:

R$^2$ is selected from the group consisting of phenyl, thienyl, and pyridinyl, wherein the R$^2$ phenyl, thienyl, and pyridinyl may be optionally substituted with one or more substituents independently selected from the group consisting of halogen, cyano, nitro, oxo, alkyl, alkenyl, —OR$^{201}$, —C(O)R$^{201}$, —NR$^{201}$R$^{202}$, and —S(O)$_2$R$^{201}$; wherein said alkyl and alkenyl substituents may be optionally substituted with one or more substituents independently selected from the group consisting of halogen, oxo, —OR$^{203}$, and —C(O)OR$^{203}$;

R$^{201}$, R$^{202}$ and R$^{203}$ are independently selected from the group consisting of hydrogen and alkyl, wherein said alkyl may be optionally substituted with one or more substituents independently selected from the group consisting of halogen, hydroxy and alkoxy;

R$^{6A}$ and R$^{6B}$ together with the nitrogen to which they are attached form a piperazinyl optionally substituted with one or more substituents independently selected from the group consisting of hydrogen, halogen, cyano, oxo, alkyl, —OR$^{601}$, —C(O)R$^{601}$, —C(O)OR$^{601}$, —NR$^{601}$R$^{602}$, —N(R$^{601}$)C(O)R$^{602}$, and —C(O)NR$^{601}$R$^{602}$, wherein said alkyl substituent may be optionally substituted with one or more substituents selected from the group consisting of halogen, —OR$^{603}$, —C(O)R$^{603}$, —C(O)OR$^{603}$, —NR$^{603}$R$^{604}$, and —C(O)NR$^{603}$R$^{604}$;

R$^{601}$, R$^{602}$, R$^{603}$ and R$^{604}$ are independently selected from the group consisting of hydrogen and alkyl, wherein said R$^{601}$ and R$^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy;

R$^8$ is alkyl substituted with —OR$^{801}$; and

R$^{801}$ is selected from the group consisting of hydrogen and alkyl, wherein (a) when said alkyl is methyl, said methyl may be optionally substituted with 1, 2, or 3 fluoro substituents, or (b) when said alkyl comprises at least two carbon atoms, said alkyl may be optionally substituted with one or more substituents independently selected from the group consisting of halogen, hydroxy, carboxy, oxo, and alkynyl.

6. The compound of claim 5 wherein R$^8$ is C$_1$ to C$_4$ alkyl substituted with —OR$^{801}$, wherein R$^{801}$ is C$_1$ to C$_4$ alkyl optionally substituted with 1, 2, or 3 fluoro substituents.

7. The compound of claim 6 wherein:

R$^2$ is selected from the group consisting of phenyl and pyridinyl, wherein the phenyl and pyridinyl may be optionally substituted with one or more substituents independently selected from the group consisting of halogen, cyano, nitro, oxo, alkyl, alkenyl, —OR$^{201}$, —C(O)R$^{201}$, —C(O)OR$^{201}$, —NR$^{201}$R$^{202}$, and —S(O)$_2$R$^{201}$; wherein said alkyl and alkenyl substituents may be optionally substituted with one or more substituents independently selected from the group consisting of halogen, oxo, —OR$^{203}$, and —C(O)OR$^{203}$;

R$^{201}$, R$^{202}$ and R$^{203}$ are independently selected from the group consisting of hydrogen and alkyl, wherein said alkyl may be optionally substituted with one or more substituents independently selected from the group consisting of halogen, hydroxy and alkoxy.

8. The compound of claim 6 wherein:

R$^2$ is phenyl, wherein the R$^2$ phenyl may be optionally substituted with one or more substituents independently selected from the group consisting of halogen, cyano, nitro, oxo, alkyl, alkenyl, —OR$^{201}$, —C(O)R$^{201}$, —NR$^{201}$R$^{202}$, and —S(O)$_2$R$^{201}$; wherein said alkyl and alkenyl substituents may be optionally substituted with one or more substituents independently selected from the group consisting of halogen, oxo, —OR$^{203}$, and —C(O)OR$^{203}$;

R$^{201}$, R$^{202}$ and R$^{203}$ are independently selected from the group consisting of hydrogen and alkyl, wherein said alkyl may be optionally substituted with one or more substituents independently selected from the group consisting of halogen, hydroxy and alkoxy.

9. The compound of claim 6 wherein:

R$^2$ is pyridinyl, wherein the R$^2$ pyridinyl may be optionally substituted with one or more substituents independently selected from the group consisting of halogen, cyano, nitro, oxo, alkyl, alkenyl, —OR$^{201}$, —C(O)R$^{201}$, —NR$^{201}$R$^{202}$, and —S(O)$_2$R$^{201}$; wherein said alkyl and alkenyl substituents may be optionally substituted with one or more substituents independently selected from the group consisting of halogen, oxo, —OR$^{203}$, and —C(O)OR$^{203}$;

R$^{201}$, R$^{202}$ and R$^{203}$ are independently selected from the group consisting of hydrogen and alkyl, wherein said alkyl may be optionally substituted with one or more substituents independently selected from the group consisting of halogen, hydroxy and alkoxy.

10. The compound of claim 6 wherein:

the R$^2$ phenyl, thienyl, and pyridinyl may be optionally substituted with one or more substituents independently selected from the group consisting of hydroxy, halogen, alkyl, —OR$^{201}$, —C(O)R$^{201}$, —NR$^{201}$R$^{202}$, and —S(O)$_2$R$^{201}$; wherein said alkyl may be optionally substituted with one or more —OR$^{203}$, and R$^{201}$, R$^{202}$ and R203 are independently selected from the group consisting of hydrogen and alkyl.

11. The compound of claim 6 wherein the R$^2$ phenyl, thienyl, and pyridinyl may be optionally substituted with one or more substituents independently selected from the group consisting of hydroxy, chloro, fluoro, methyl, methoxy, ethoxy, hydroxymethyl, —C(O)CH$_3$, —C(O)CH(CH$_3$)$_2$, —N(CH$_3$)$_2$, and —S(O)$_2$CH$_2$ (CH$_3$).

12. The compound of claim 6 wherein:
R$^{6A}$ and R$^{6B}$ together with the nitrogen to which they are attached form a piperazinyl optionally substituted with one or more substituents independently selected from the group consisting of halogen, alkyl, —OR$^{601}$, and —C(O)NR$^{601}$R$^{602}$, wherein said alkyl substituent may be optionally substituted with one or more substituent selected from the group consisting of -OR$^{603}$, —C(O)OR$^{603}$, and —NR$^{603}$R$^{604}$; and
R$^{601}$, R$^{602}$, R$^{603}$ and R$^{604}$ are independently selected from the group consisting of hydrogen and alkyl.

13. The compound of claim 6 wherein R$^{6A}$ and R$^{6B}$ together with the nitrogen to which they are attached form a piperazinyl optionally substituted with one or more substituents independently selected from the group consisting of chloro, hydroxy, ethyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

14. The compound of claim 5 wherein:
R$^2$ is selected from the group consisting of phenyl and pyridinyl, wherein the phenyl and pyridinyl may be optionally substituted with hydroxy, halogen, alkyl, —OR$^{201}$, —C(O)R$^{201}$, NR$^{201}$R$^{202}$, and —S(O)$_2$R$^{201}$; wherein said alkyl may be optionally substituted with one or more —OR$^{203}$;
R$^{201}$, R$^{202}$ and R$^{203}$ are independently selected from the group consisting of hydrogen and alkyl;
R$^{6A}$ and R$^{6B}$ together with the nitrogen to which they are attached form a piperazinyl optionally substituted with one or more substituents selected from the group consisting of halogen, alkyl, —OR$^{601}$, and —C(O)NR$^{601}$R$^{602}$, wherein said alkyl substituent may be optionally substituted with one or more substituent selected from the group consisting of —OR$^{603}$, —C(O)OR$^{603}$, and —NR$^{603}$R$^{604}$; and
R$^{601}$, R$^{602}$, R$^{603}$ and R$^{604}$ are independently selected from the group consisting of hydrogen and alkyl.

15. The compound of claim 6 wherein:
R$^2$ is selected from the group consisting of phenyl and pyridinyl, wherein the phenyl and pyridinyl may be optionally substituted with one or more substituents selected from the group consisting of hydroxy, chloro, fluoro, methyl, methoxy, ethoxy, hydroxymethyl, —C(O)CH$_3$, —C(O)CH(CH$_3$)$_2$, —N(CH$_3$)$_2$, and —S(O)$_2$CH$_2$(CH$_3$), and
R$^{6A}$ and R$^{6B}$ together with the nitrogen to which they are attached form a piperazinyl optionally substituted with one or more substituents selected from the group consisting of chloro, hydroxy, ethyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

16. The compound of claim 15 wherein:
R$^8$ is ethyl, and
R$^{801}$ is selected from the group consisting of hydrogen, methyl, ethyl and propyl, wherein said methyl, ethyl and propyl may be optionally substituted with 1, 2, or 3 fluoro substituents.

17. The compound of claim 15 wherein:
R$^2$ is pyridinyl substituted with methoxy;
R$^{6A}$ and R$^{6B}$ together with the nitrogen to which they are attached form a piperazinyl, optionally substituted with one or more substituents selected from the group consisting of chloro, hydroxy, ethyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$; and
R$^8$ is propoxyethyl.

18. A compound, or a pharmaceutically acceptable salt thereof of the compound, wherein the compound has the structure of Formula I-12:

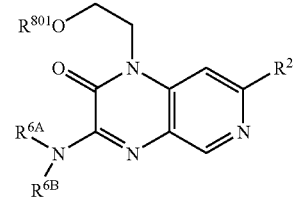

(I-12)

and wherein
R$^2$ is pyridinyl, optionally substituted with one or more substituents independently selected from the group consisting of halogen, cyano, nitro, oxo, alkyl, alkenyl, alkynyl, cycloalkyl, —OR$^{201}$, —C(O)R$^{201}$, —OC(O)R$^{201}$, —C(O)OR$^{201}$, —NR$^{201}$R$^{202}$, —N(R$^{202}$)C(O)R$^{202}$, —C(O)NR$^{201}$R$^{202}$, —C(O)NR$^{201}$C(O)R$^{202}$ and —S(O)$_2$R$^{201}$; wherein said alkyl, alkenyl, and alkynyl and cycloalkyl substituents may be optionally substituted with one or more substituents independently selected from the group consisting of halogen, oxo, —OR$^{203}$, and —C(O)OR$^{203}$;
R$^{201}$, R$^{202}$ and R$^{203}$ are independently selected from the group consisting of hydrogen and alkyl, wherein said alkyl may be optionally substituted with one or more substituents independently selected from the group consisting of halogen, hydroxy, alkoxy, carboxy and —C(O)NH$_2$;
R$^{6A}$ and R$^{6B}$ together with the nitrogen to which they are attached form a piperazinyl optionally substituted with one or more substituents independently selected from the group consisting of hydrogen, halogen, oxo, alkyl, alkenyl, alkynyl, cyano, —OR$^{601}$, —C(O)R$^{601}$, —OC(O)R$^{601}$, —C(O)OR$^{601}$, —NR$^{601}$R$^{602}$, —N(R$^{601}$)C(O)R$^{602}$, —C(O)NR$^{601}$R$^{602}$, —C(O)NR$^{601}$C(O)R$^{602}$, cycloalkyl, aryl, and heterocyclyl, wherein (a) said alkyl, alkoxy, alkylamino, alkylcarbonyl, alkenyl, alkynyl and cycloalkyl substituents may be optionally substituted with one or more substituents independently selected from the group consisting of halogen, cyano, oxo, —OR$^{603}$, —C(O)R$^{603}$, —C(O)OR$^{603}$, —OC(O)R$^{603}$, —NR$^{603}$R$^{604}$, —N(R$^{603}$)C(O)R$^{604}$, —C(O)NR$^{603}$R$^{604}$, —C(O)NR$^{603}$C(O)R$^{604}$, —SR$^{603}$, —S(O)R$^{603}$, —S(O)$_2$R$^{603}$, N(R$^{603}$)S(O)$_2$R$^{604}$, and —S(O)$_2$NR$^{603}$R$^{604}$, C(O)NR$^{603}$C(O)R$^{604}$, —SR$^{603}$, —S(O)R$^{603}$, —S(O)$_2$R$^{603}$, —N(R$^{603}$)S(O)$_2$R$^{604}$, and —S(O)$_2$NR$^{603}$R$^{604}$, and (b) said aryl and heterocyclyl substituents may be optionally substituted with one or more substituents independently selected from the group consisting of halogen, alkyl, alkenyl, alkynyl, cyano, oxo, —OR$^{601}$, —C(O)R$^{601}$, —C(O)OR$^{601}$, —OC(O)R$^{601}$, —NR$^{601}$R$^{602}$, —N(R$^{601}$)C(O)R$^{602}$, —C(O)NR$^{601}$R$^{602}$, —C(O)NR$^{601}$C(O)R$^{602}$, —SR601, —S(O)R$^{602}$, —S(O)$_2$R$^{601}$, —N(R$^{601}$)S(O)$_2$R$^{602}$, and —S(O)$_2$NR$^{601}$R$^{602}$;

$R^{601}$, $R^{602}$, $R^{603}$ and $R^{604}$ are independently selected from the group consisting of hydrogen, alkyl, alkenyl, and alkynyl, wherein (a) said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy, and (b) said $R^{601}$ and $R^{602}$ alkenyl and alkynyl substituents may be optionally substituted with one or more substituents independently selected from the group consisting of halogen, cyano, hydroxy, carboxy, oxo, alkoxy, haloalkoxy, hydroxyalkoxy, and carboxyalkoxy; and $R^{801}$ is selected from the group consisting of hydrogen, and methyl, ethyl and propyl, wherein said methyl, ethyl and propyl may be optionally substituted with 1, 2, or 3 fluoro substituents.

19. The compound of claim 18 wherein:

$R^2$ is pyridinyl, optionally substituted with one or more substituents independently selected from the group consisting of hydroxy, halogen, alkyl, —$OR^{201}$, —C(O)$R^{201}$, $NR^{201}R^{202}$, — and —S(O)$_2R^{201}$; wherein said alkyl may be optionally substituted with one or more —$OR^{203}$, and $R^{201}$, $R^{202}$ and $R^{203}$ are independently selected from the group consisting of hydrogen and alkyl.

20. The compound of claim 18 wherein $R^2$ is pyridinyl, optionally substituted with one or more substituents selected from the group consisting of hydroxy, chloro, fluoro, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$).

21. The compound of claim 18 wherein the $R^2$ pyridinyl is selected from the group consisting of

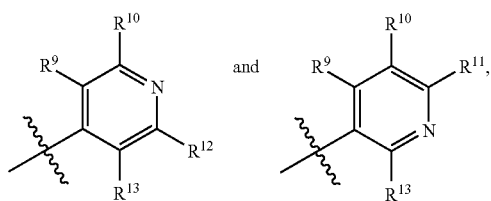

wherein $R^9$, $R^{10}$, $R^{11}$, and $R^{13}$ are independently selected from the group consisting of hydrogen, halogen, hydroxy, alkyl, hydroxyalkyl, aminoalkyl, alkoxy, alkoxyalkyl, amino, alkylamino, aminosulfonyl, and alkylsulfonyl.

22. The compound of claim 18 wherein $R^2$ has the structure

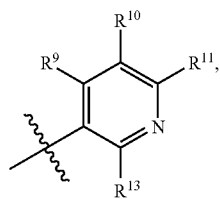

wherein $R^9$, $R^{10}$, $R^{11}$, and $R^{13}$ are independently selected from the group consisting of hydrogen, halogen, hydroxy, alkyl, hydroxyalkyl, aminoalkyl, alkoxy, alkoxyalkyl, amino, alkylamino, aminosulfonyl, and alkylsulfonyl.

23. The compound of claim 18 wherein $R^2$ is

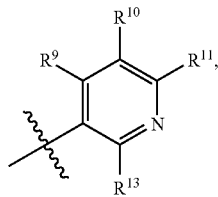

wherein $R^9$, $R^{10}$, $R^{11}$, and $R^{13}$ are independently selected from the group consisting of hydrogen, chloro, fluoro, hydroxy, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$).

24. The compound of claim 23 wherein at least one of $R^9$, $R^{10}$, $R^{11}$, and $R^{13}$ is independently selected from the group consisting of chloro, fluoro, hydroxy, methyl, methoxy, ethoxy, hydroxymethyl, —C(O)CH$_3$, —C(O)CH(CH$_3$)$_2$, —N(CH$_3$)$_2$, and —S(O)$_2$CH$_2$(CH$_3$).

25. The compound of claim 23 wherein $R^9$, $R^{10}$ and $R^{13}$ are each hydrogen, and $R^{11}$ is selected from the group consisting of hydrogen, chloro, fluoro, hydroxy, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$).

26. The compound of claim 23 wherein $R^9$, $R^{10}$ and $R^{13}$ are each hydrogen, and $R^{11}$ is selected from the group consisting of hydrogen, methyl, methoxy, and —N(CH$_3$)$_2$.

27. The compound of claim 23 wherein $R^9$, $R^{10}$ and $R^{13}$ are each hydrogen, and $R^{11}$ is methoxy.

28. The compound of claim 24 wherein:

$R^{6A}$ and $R^{6B}$ together with the nitrogen to which they are attached form a piperazinyl optionally substituted with one or more substituents independently selected from the group consisting of hydrogen, halogen, cyano, oxo, alkyl, —$OR^{601}$, —C(O)$R^{601}$, —C(O)O$R^{601}$, —$NR^{601}R^{602}$, —N($R^{601}$)C(O)$R^{602}$, and —C(O)$NR^{601}R^{602}$, wherein said alkyl substituent may be optionally substituted with one or more substituents independently selected from the group consisting of halogen, —$OR^{603}$, —C(O)$R^{603}$, —C(O)O$R^{603}$, and —$NR^{603}R^{604}$; and $R^{601}$, $R^{602}$, $R^{603}$ and $R^{604}$ are independently selected from the group consisting of hydrogen and alkyl, wherein said $R^{601}$ and $R^{602}$ alkyl may be optionally substituted with one or more substituents independently selected from the group consisting of halogen, cyano, hydroxy, carboxy, oxo, alkynyl, haloalkynyl, hydroxyalkynyl, carboxyalkynyl, alkoxy, haloalkoxy, hydroxyalkoxy, and carboxyalkoxy.

29. The compound of claim 23 wherein:

$R^{6A}$ and $R^{6B}$ together with the nitrogen to which they are attached form a piperazinyl optionally substituted with one or more substituents independently selected from the group consisting of halogen, alkyl, —$OR^{601}$, and —C(O)$NR^{601}R^{602}$, wherein said alkyl substituent may be optionally substituted with one or more substituents independently selected from the group consisting of –$OR^{603}$, —C(O)O$R^{603}$, and —$NR^{603}R^{604}$; and $R^{601}$, $R^{602}$, $R^{603}$ and $R^{604}$ are independently selected from the group consisting of hydrogen and alkyl.

30. The compound of claim 23 wherein $R^{6A}$ and $R^{6B}$ together with the nitrogen to which they are attached form a piperazinyl wherein the piperazinyl may be optionally substituted with one or more substituents independently selected from the group consisting of pyrrolidinyl, piperidinyl, piperazinyl, morpholinyl, and diazapinyl, wherein the pyrrolidinyl, piperidinyl, piperazinyl, morpholinyl, and diazapinyl may be optionally substituted with one or more substituent selected from the group consisting of chloro, hydroxy, methyl, ethyl, propyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

31. The compound of claim 19, wherein:
 R$^{6A}$ and R$^{6B}$ together with the nitrogen to which they are attached form a piperazinyl optionally substituted with one or more substituents independently selected from the group consisting of halogen, alkyl, —OR$^{601}$, and —C(O)NR$^{601}$R$^{602}$, wherein said alkyl substituent may be optionally substituted with one or more substituents independently selected from the group consisting of —OR$^{603}$, —C(O)OR$^{603}$, and —NR$^{603}$R$^{604}$; and
 R$^{601}$, R$^{602}$, R$^{603}$ and R$^{604}$ are independently selected from the group consisting of hydrogen and alkyl.

32. The compound of claim 20, wherein:
 R$^{6A}$ and R$^{6B}$ together with the nitrogen to which they are attached form a piperazinyl optionally substituted with one or more substituents independently selected from the group consisting of chloro, hydroxy, methyl, ethyl, propyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

33. The compound of claim 21, wherein:
 R$^{6A}$ and R$^{6B}$ together with the nitrogen to which they are attached form a piperazinyl optionally substituted with one or more substituents independently selected from the group consisting of chloro, hydroxy, methyl, ethyl, propyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

34. The compound of claim 23, wherein:
 R$^9$, R$^{10}$ and R$^{13}$ are each hydrogen;
 R$^{11}$ is selected from the group consisting of hydrogen, hydroxy, chloro, fluoro, methyl, ethyl, methoxy, ethoxy, hydroxymethyl, hydroxyethyl, —C(O)CH$_3$, —C(O)CH(CH$_3$)$_2$, —N(CH$_3$)$_2$, and —S(O)$_2$CH$_2$(CH$_3$);
 R$^{6A}$ and R$^{6B}$ together with the nitrogen to which they are attached form a piperazinyl optionally substituted with one or more substituents independently selected from the group consisting of chloro, hydroxy, methyl, ethyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$; and
 R$^{801}$ is propyl.

35. The compound of claim 34 wherein one of R$^9$, R$^{10}$, R$^{11}$ and R$^{13}$ is methoxy, and the remainder of R$^9$, R$^{10}$, R$^{11}$ and R$^{13}$ are hydrogen.

36. The compound of claim 35 wherein R$^{6A}$ and R$^{6B}$ together with the nitrogen to which they are attached form a piperazinyl, wherein the piperazinyl may be optionally substituted with one or more substituents independently selected from the group consisting of chloro, hydroxy, methyl, ethyl, propyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, —CH$_2$C(O)OH, and —C(O)NH$_2$.

37. The compound of claim 36 wherein the piperazinyl may be optionally substituted with one or more substituents independently selected from the group consisting of methyl, ethyl, propyl, hydroxymethyl, hydroxyethyl, hydroxypropyl, —CH$_2$C(CH$_3$)$_2$NH$_2$, —CH(CH$_3$)CH(CH$_3$)NH$_2$, —CH$_2$CH(CH$_3$)OH, —CH$_2$C(O)OC(CH$_3$)$_3$, and —CH$_2$C(O)OH.

38. A compound of claim 1, or a pharmaceutically acceptable salt thereof, selected from the group consisting of:
 7-(6-methoxypyridin-3-yl)-3-(piperazin-1-yl)-1-(2-propoxyethyl)pyrido[3,4-b]pyrazin-2(1H)-one;
 3-[4-(2-hydroxyethyl)piperazin-1-yl]-7-(6-methoxypyridin-3-yl)-1-(2-propoxyethyl)pyrido[3,4-b]pyrazin-2(1H)-one;
 3-[(3S)-4-(2-hydroxethyl)-3-methylpiperazin-1-yl]-7-(6-methoxypyridin-3-yl)-1-(2-propoxyethyl)pyrido[3,4-b]pyrazin-2(1H)-one;
 3-[4-(3-hydroxpropyl)-3,5-dimethylpiperazin-1-yl]-7-(6-methoxypyridin-3-yl)-1-(2-propoxyethyl)pyrido[3,4-b]pyrazin-2(1H)-one; and
 3-[4-(3-hydroxpropyl)piperazin-1-yl]-7-(6-methoxypyridin-3-yl)-1-(2-propoxyethyl)pyrido[3,4-b]pyrazin-2(1H)-one;
or a pharmaceutically acceptable salt salts thereof.

39. A compound of claim 1, or a pharmaceutically acceptable salt thereof, selected from the group consisting of:
 7-(4-chlorophenyl)-3-(4-(2-hydroxyethyl)piperazin-1-yl)-1-(2-propoxyethyl)pyrido[3,4-b]pyrazin-2(1H)-one;
 3-(4-(2-hydroxyethyl)piperazin-1-yl)-7-(4-hydroxyphenyl)-1-(2-propoxyethyl)pyrido[3,4-b]pyrazin-2(1H)-one;
 7-(4-(dimethylamino)-2-methylphenyl)-3-(4-(2-hydroxyethyl)piperazin-1-yl)-1-(2-propoxyethyl)pyrido[3,4-b]pyrazin-2(1H)-one;
 7-(3-chlorophenyl)-3-(4-(2-hydroxyethyl)piperazin-1-yl)-1-(2-propoxyethyl)pyrido[3,4-b]pyrazin-2(1H)-one;
 3-(4-(2-hydroxyethyl)piperazin-1-yl)-7-(4-methoxyphenyl)-1-(2-propoxyethyl)pyrido[3,4-b]pyrazin-2(1H)-one;
 7-(2,4-difluorophenyl)-3-(4-(2-hydroxyethyl)piperazin-1-yl)-1-(2-propoxyethyl)pyrido[3,4-b]pyrazin-2(1H)-one;
 7-(4-(ethylsulfonyl)phenyl)-3-(4-(2-hydroxyethyl)piperazin-1-yl)-1-(2-propoxyethyl)pyrido[3,4-b]pyrazin-2(1H)-one;
 7-(2-fluoro-3-methoxyphenyl)-3-(4-(2-hydroxyethyl)piperazin-1-yl)-1-(2-propoxyethyl)pyrido[3,4-b]pyrazin-2(1H)-one; and
 3-(4-(2-hydroxyethyl)piperazin-1-yl)-7-(4-isopropoxyphenyl)-1-(2-propoxyethyl)pyrido[3,4-b]pyrazin-2(1H)-one,
or a pharmaceutically acceptable salt salts thereof.

40. A compound of claim 1, or a pharmaceutically acceptable salt thereof, selected from the group consisting of:
 3-(4-(2-hydroxyethyl)piperazin-1-yl)-7-(isoquinolin-5-yl)-1-(2-propoxyethyl)pyrido[3,4-b]pyrazin-2(1H)-one;
 3-(4-(2-hydroxyethyl)piperazin-1-yl)-7-(4-(hydroxymethyl)phenyl)-1-(2-propoxyethyl)pyrido[3,4-b]pyrazin-2(1H)-one;
 7-(4-ethoxphenyl)-3-(4-(2-hydroxyethyl)piperazin-1-yl)-1-(2-propoxyethyl)pyrido[3,4-b]pyrazin-2(1H)-one;
 7-(4-fluoro-3-methylphenyl)-3-(4-(2-hydroxyethyl)piperazin-1-yl)-1-(2-propoxyethyl)pyrido[3,4-b]pyrazin-2(1H)-one;
 7-(2,3-difluorophenyl)-3-(4-(2-hydroxyethyl)piperazin-1-yl)-1-(2-propoxyethyl)pyrido[3,4-b]pyrazin-2(1H)-one;

3-(4-(2-hydroxyethyl)piperazin-1-yl)-1-(2-propoxyethyl)-7-p-tolylpyrido[3,4-b]pyrazin-2(1H)-one;

7-(5-acetylthiophen-2-yl)-3-(4-(2-hydroxyethyl)piperazin-1-yl)-1-(2-propoxyethyl)pyrido[3,4-b]pyrazin-2(1H)-one;

3-(4-(2-hydroxyethyl)piperazin-1-yl)-7-(3-methoxyphenyl)-1-(2-propoxyethyl)pyrido[3,4-b]pyrazin-2(1H)-one;

3-(4-(2-hydroxyethyl)piperazin-1-yl)-7-(3-(hydroxymethyl)phenyl)-1-(2-propoxyethyl)pyrido[3,4-b]pyrazin-2(1H)-one; and 3-(4-(2-hydroxyethyl)piperazin-1-yl)-1-(2-propoxyethyl)-7-(pyridin-3-yl)pyrido[3,4-b]pyrazin-2(1H)-one, or a pharmaceutically acceptable salt salts thereof.

41. A compound of claim 1, or a pharmaceutically acceptable salt thereof, selected from the group consisting of:

7-(3-ethoxyphenyl)-3-(4-(2-hydroxyethyl)piperazin-1-yl)-1-(2-propoxyethyl)pyrido[3,4-b]pyrazin-2(1H)-one;

7-(3-fluoro-4-methoxyphenyl)-3-(4-(2-hydroxyethyl)piperazin-1-yl)-1-(2-propoxyethyl)pyrido[3,4-b]pyrazin-2(1H)-one;

7-(5-chloro-2-fluorophenyl)-3-(4-(2-hydroxyethyl)piperazin-1-yl)-1-(2-propoxyethyl)pyrido[3,4-b]pyrazin-2(1H)-one;

3-(4-(2-hydroxyethyl)piperazin-1-yl)-7-(4-methoxy-3-methylphenyl)-1-(2-propoxyethyl)pyrido[3,4-b]pyrazin-2(1H)-one;

3-(4-(2-hydroxyethyl)piperazin-1-yl)-1-(2-propoxyethyl)-7-m-tolylpyrido[3,4-b]pyrazin-2(1H)-one;

3-(4-(2-hydroxyethyl)piperazin-1-yl)-7-(2-hydroxyphenyl)-1-(2-propoxyethyl)pyrido[3,4-b]pyrazin-2(1H)-one;

7-(2-fluorophenyl)-3-(4-(2-hydroxyethyl)piperazin-1-yl)-1-(2-propoxyethyl)pyrido[3,4-b]pyrazin-2(1H)-one; and 3-(4-ethylpiperazin-1-yl)-7-(6-methoxypyridin-3-yl)-1-(2-propoxyethyl)pyrido[3,4-b]pyrazin-2(1H)-one;

or a pharmaceutically acceptable salt salts thereof.

42. A compound of claim 1, or a pharmaceutically acceptable salt thereof, selected from the group consisting of:

3-(4-(2-hydroxy-2-methylpropyl)piperazin-1-yl)-7-(6-methoxypyridin-3-yl)-1-(2-propoxyethyl)pyrido[3,4-b]pyrazin-2(1H)-one;

3-(4-((2S,3R)-3-hydroxybutan-2-yl)piperazin-1-yl)-7-(6-methoxypyridin-3-yl)-1-(2-propoxyethyl)pyrido[3,4-b]pyrazin-2(1H)-one;

3-(4-((2R,3R)-3-hydroxybutan-2-yl)piperazin-1-yl)-7-(6-methoxypyridin-3-yl)-1-(2-propoxyethyl)pyrido[3,4-b]pyrazin-2(1H)-one;

3-(4-((S)-2-hydroxypropyl)piperazin-1-yl)-7-(6-methoxypyridin-3-yl)-1-(2-propoxyethyl)pyrido[3,4-b]pyrazin-2(1H)-one;

3-(4-((R)-2-hydroxypropyl)piperazin-1-yl)-7-(6-methoxypyridin-3-yl)-1-(2-propoxyethyl)pyrido[3,4-b]pyrazin-2(1H)-one; and or a pharmaceutically acceptable salt salts thereof.

43. A pharmaceutical composition comprising a compound of claim 1, or a pharmaceutically acceptable salt thereof, and a pharmaceutically acceptable carrier.

44. 3-[4-(2-hydroxyethyl)piperazin-1-yl]-7-(6-methoxypyridin-3H)-1-(2-propoxyethyl)pyrido[3,4-b]pyrazin-2(1H)-one or a pharmaceutically acceptable salt thereof.

45. A method of treating pulmonary arterial hypertension in a mammal in need thereof, said method comprising administering to said mammal a therapeutically effective amount of a compound of claim 1 or a pharmaceutically acceptable salt thereof.

* * * * *